US010245332B2

(12) United States Patent
Robinson et al.

(10) Patent No.: US 10,245,332 B2
(45) Date of Patent: Apr. 2, 2019

(54) CONTRAST AGENTS FOR APPLICATIONS INCLUDING PERFUSION IMAGING

(71) Applicant: Lantheus Medical Imaging, Inc., North Billerica, MA (US)

(72) Inventors: Simon P. Robinson, Stow, MA (US); David S. Casebier, Carlisle, MA (US); Ming Yu, Chelmsford, MA (US); Mikhail Kagan, North Chelmsford, MA (US); Joel Lazewatsky, Auburndale, MA (US)

(73) Assignee: Lantheus Medical Imaging, Inc., North Billerica, MA (US)

( * ) Notice: Subject to any disclaimer, the term of this patent is extended or adjusted under 35 U.S.C. 154(b) by 260 days.

(21) Appl. No.: 15/153,502

(22) Filed: May 12, 2016

(65) Prior Publication Data

US 2016/0361448 A1    Dec. 15, 2016
US 2018/0133347 A9    May 17, 2018

Related U.S. Application Data

(63) Continuation of application No. 12/919,600, filed as application No. PCT/US2009/001247 on Feb. 27, 2009, now Pat. No. 9,408,927.

(60) Provisional application No. 61/067,593, filed on Feb. 29, 2008.

(51) Int. Cl.
*A61K 51/04* (2006.01)

(52) U.S. Cl.
CPC ................................ *A61K 51/0459* (2013.01)

(58) Field of Classification Search
CPC .................................................. A61K 51/0459
See application file for complete search history.

(56) References Cited

U.S. PATENT DOCUMENTS

| | | | |
|---|---|---|---|
| 3,359,103 A | 12/1967 | Becker et al. | |
| 4,783,462 A | 11/1988 | Mutsukado et al. | |
| 4,874,861 A | 10/1989 | Ogura et al. | |
| 4,910,201 A | 3/1990 | Kawamura et al. | |
| 5,087,440 A | 2/1992 | Cacheris et al. | |
| 5,088,499 A | 2/1992 | Unger | |
| 5,093,105 A | 3/1992 | Flanagan et al. | |
| 5,098,900 A | 3/1992 | Mutsukado et al. | |
| 5,155,215 A | 10/1992 | Ranney | |
| 5,169,848 A | 12/1992 | Bettarini et al. | |
| 5,169,942 A | 12/1992 | Johnson | |
| 5,228,446 A | 7/1993 | Unger et al. | |
| 5,281,704 A | 1/1994 | Love et al. | |
| 5,306,482 A | 4/1994 | Tartaglia et al. | |
| 5,377,681 A | 1/1995 | Drane | |
| 5,384,113 A | 1/1995 | Deutsch et al. | |
| 5,393,512 A | 2/1995 | Vanderheyden et al. | |
| 5,412,148 A | 5/1995 | Keana | |
| 5,417,959 A | 5/1995 | Wallace | |
| 5,436,325 A | 7/1995 | Johnson et al. | |
| 5,520,904 A | 5/1996 | Nosco et al. | |
| 5,547,656 A | 8/1996 | Unger | |
| 5,567,411 A | 10/1996 | Keana et al. | |
| 5,585,112 A | 12/1996 | Unger et al. | |
| 5,587,491 A | 12/1996 | Hoye et al. | |
| 5,679,810 A | 10/1997 | Love et al. | |
| 5,760,191 A | 6/1998 | Snow et al. | |
| 5,801,228 A | 9/1998 | Hollister et al. | |
| 5,804,161 A | 9/1998 | Long et al. | |
| 5,811,073 A | 9/1998 | Kassis et al. | |
| 5,827,073 A | 10/1998 | Leuscher et al. | |
| 5,846,517 A | 12/1998 | Unger | |
| 5,961,955 A | 10/1999 | Shochat et al. | |
| 6,056,939 A | 5/2000 | Desreux et al. | |
| 6,066,309 A | 5/2000 | Zamora et al. | |
| 6,241,964 B1 | 6/2001 | Burns et al. | |
| 6,565,889 B2 | 5/2003 | Zasadzinski et al. | |
| 7,112,318 B2 | 9/2006 | Madar et al. | |
| 7,344,702 B2 | 3/2008 | Casebier et al. | |
| 7,410,998 B2 | 8/2008 | Nicolaou et al. | |
| 7,485,283 B2 | 2/2009 | Radeke et al. | |
| 7,824,659 B2 | 11/2010 | Casebier et al. | |
| 7,847,092 B2 | 12/2010 | Moon et al. | |
| 7,871,623 B2 | 1/2011 | Biswal et al. | |
| 7,927,616 B2 | 4/2011 | Yamashita | |
| 8,226,929 B2 | 7/2012 | Casebier et al. | |
| 8,263,042 B2 | 9/2012 | Radeke et al. | |
| 8,936,777 B2 | 1/2015 | Cesati et al. | |
| 9,029,295 B2 | 5/2015 | Kuragano et al. | |
| 9,161,997 B2 | 10/2015 | Casebier et al. | |

(Continued)

FOREIGN PATENT DOCUMENTS

| | | |
|---|---|---|
| CN | 1925878 A | 3/2007 |
| CN | 101555232 A | 10/2009 |

(Continued)

OTHER PUBLICATIONS

Esposti Biochimica et Biophysica Acta 1364, 1998, p. 222.*
Rowlands Pharmacology and Toxicology, 1998, p. 214.*
Supplementary European Search Report for EP05756378.5, dated Jul. 17, 2009.
Extended European Search Report for EP10176056.9, dated Apr. 8, 2013.
International Search Report and Written Opinion for PCT/US05/014459, dated Oct. 21, 2005.
International Preliminary Report on Patentability for PCT/US05/014459, dated Nov. 1, 2006.
Supplementary Extended European Search Report for EP05723066.6, dated Dec. 5, 2008.
International Search Report and Written Opinion for PCT/US05/004687, dated Nov. 17, 2005.

(Continued)

*Primary Examiner* — David J Blanchard
*Assistant Examiner* — Thurman Wheeler
(74) *Attorney, Agent, or Firm* — Wolf, Greenfield & Sacks, P.C.

(57) ABSTRACT

The present invention is directed, in part, to compounds and methods for imaging the central nervous system or cancer, comprising administering to a subject a contrast agent which comprises a compound that binds MC-1, and an imaging moiety, and scanning the subject using diagnostic imaging.

20 Claims, 4 Drawing Sheets

(56) References Cited

U.S. PATENT DOCUMENTS

| | | | |
|---|---|---|---|
| 9,408,927 | B2 | 8/2016 | Robinson et al. |
| 9,550,000 | B2 | 1/2017 | Robinson et al. |
| 9,603,951 | B2 | 3/2017 | Lazewatsky et al. |
| 9,713,651 | B2 | 7/2017 | Robinson et al. |
| 9,718,786 | B2 | 8/2017 | Casebier et al. |
| 2003/0044354 | A1 | 3/2003 | Carpenter et al. |
| 2003/0124054 | A1 | 7/2003 | Toyohara et al. |
| 2004/0033197 | A1 | 2/2004 | Madar et al. |
| 2004/0034239 | A1 | 2/2004 | Nicolaou et al. |
| 2004/0142872 | A1 | 7/2004 | Poduslo et al. |
| 2004/0142972 | A1 | 7/2004 | Edgar et al. |
| 2005/0020594 | A1 | 1/2005 | Hepperle et al. |
| 2005/0129612 | A1 | 6/2005 | Zaczek et al. |
| 2005/0191238 | A1* | 9/2005 | Casebier ............ A61K 49/0002 424/1.11 |
| 2005/0244332 | A1 | 11/2005 | Radeke et al. |
| 2006/0083681 | A1 | 4/2006 | Purohit et al. |
| 2007/0036716 | A1 | 2/2007 | Casebier et al. |
| 2007/0082879 | A1 | 4/2007 | Goodman |
| 2007/0258887 | A1 | 11/2007 | Tamagnan et al. |
| 2009/0104118 | A1 | 4/2009 | Radeke et al. |
| 2009/0297442 | A1 | 12/2009 | Hemstad |
| 2010/0236958 | A1 | 9/2010 | Veggeland et al. |
| 2010/0322855 | A1 | 12/2010 | Chong et al. |
| 2011/0091374 | A1 | 4/2011 | Robinson et al. |
| 2012/0237445 | A1 | 9/2012 | Castner et al. |
| 2012/0276006 | A1 | 11/2012 | Casebier et al. |
| 2013/0028837 | A1 | 1/2013 | Radeke et al. |
| 2013/0064769 | A1 | 3/2013 | Cesati, III et al. |
| 2013/0101508 | A9 | 4/2013 | Castner et al. |
| 2014/0328756 | A1 | 11/2014 | Cesati, III et al. |
| 2015/0165074 | A1 | 6/2015 | Lazewatsky et al. |
| 2015/0196672 | A1 | 7/2015 | Cesati et al. |
| 2016/0130235 | A1 | 5/2016 | Casebier et al. |

FOREIGN PATENT DOCUMENTS

| | | |
|---|---|---|
| EP | 0 169 375 A2 | 1/1986 |
| EP | 0 186 817 A1 | 7/1986 |
| EP | 0 111 415 B1 | 4/1990 |
| EP | 0 393 641 A2 | 10/1990 |
| EP | 0 627 424 A1 | 12/1994 |
| EP | 0 665 223 A1 | 8/1995 |
| EP | 0 727 225 A2 | 8/1996 |
| EP | 1 741 703 A1 | 1/2007 |
| JP | S60-004173 A | 1/1985 |
| JP | S61-017570 A | 1/1986 |
| JP | S61-130275 A | 6/1986 |
| JP | S61-260018 A | 11/1986 |
| JP | S61-267560 A | 11/1986 |
| JP | S62-5967 A | 1/1987 |
| JP | S62-123176 A | 6/1987 |
| JP | S63-159372 A | 7/1988 |
| JP | S63-159373 A | 7/1988 |
| JP | S63-159374 A | 7/1988 |
| JP | H02-088507 A | 9/1990 |
| JP | H02-279676 A | 11/1990 |
| JP | H03-220177 A | 9/1991 |
| JP | H04-235975 A | 8/1992 |
| JP | H07-252236 A | 10/1995 |
| JP | 2007-112725 A | 5/2007 |
| JP | 2012-149044 A | 8/2012 |
| WO | WO 91/14460 A1 | 10/1991 |
| WO | WO 92/17215 A1 | 10/1992 |
| WO | WO 94/12479 A1 | 6/1994 |
| WO | WO 94/22496 A1 | 10/1994 |
| WO | WO 95/11901 A1 | 5/1995 |
| WO | WO 95/33757 A1 | 12/1995 |
| WO | WO 00/078283 A1 | 12/2000 |
| WO | WO 02/20008 A1 | 3/2002 |
| WO | WO 03/002157 A1 | 1/2003 |
| WO | WO 03/065882 A2 | 8/2003 |
| WO | WO 03/082350 A2 | 10/2003 |
| WO | WO 03/086476 A1 | 10/2003 |
| WO | WO 04/056400 A1 | 7/2004 |
| WO | WO 2005/009393 A2 | 2/2005 |
| WO | WO 2005/012319 A1 | 2/2005 |
| WO | WO 2005/079391 A2 | 9/2005 |
| WO | WO 2005/082425 A1 | 9/2005 |
| WO | WO 2005/103265 A1 | 11/2005 |
| WO | WO 2005/105159 A2 | 11/2005 |
| WO | WO 2007/021858 A2 | 2/2007 |
| WO | WO 2008/022979 A1 | 2/2008 |
| WO | WO 2008/081852 A1 | 7/2008 |
| WO | WO 2009/054653 A2 | 4/2009 |
| WO | WO 2009/086041 A1 | 7/2009 |
| WO | WO 2009/103478 A1 | 8/2009 |
| WO | WO 2009/108376 A2 | 9/2009 |
| WO | WO 2009/110984 A2 | 9/2009 |
| WO | WO 2009/127544 A1 | 10/2009 |
| WO | WO 2010/104818 A1 | 9/2010 |
| WO | WO 2010/120368 A2 | 10/2010 |
| WO | WO 2011/006610 A1 | 1/2011 |
| WO | WO 2011/097649 A2 | 8/2011 |
| WO | WO 2013/058774 A2 | 4/2013 |
| WO | WO 2014/026079 A2 | 2/2014 |

OTHER PUBLICATIONS

International Preliminary Report on Patentability for PCT/US05/004687, dated Aug. 14, 2006.
International Search Report and Written Opinion for PCT/US2006/031231, dated Mar. 15, 2007.
International Preliminary Report on Patentability for PCT/US2006/031231, dated Feb. 21, 2008.
Extended European Search Report for EP09716528.6, dated Mar. 14, 2013.
International Search Report and Written Opinion for PCT/US2009/001247, dated Oct. 21, 2009.
International Preliminary Report on Patentability for PCT/US2009/001247, dated Sep. 10, 2010.
International Search Report and Written Opinion for PCT/US2009/001296, dated Sep. 30, 2009.
International Preliminary Report on Patentability for PCT/US2009/001296, dated Sep. 10, 2010.
International Search Report and Written Opinion for PCT/US2010/001120, dated Dec. 28, 2010.
International Preliminary Report on Patentablitiy for PCT/US2010/001120, dated Oct. 27, 2011.
Extended European Search Report for EP11740546.4, dated Jun. 25, 2013.
International Search Report and Written Opinion for PCT/US2011/024109, dated Oct. 24, 2011.
International Preliminary Report on Patentability for PCT/US2011/024109, dated Aug. 23, 2012.
International Search Report and Written Opinion for PCT/US2011/057358, dated May 9, 2012.
International Preliminary Report on Patentability for PCT/US2011/057358 dated May 1, 2014.
International Search Report and Written Opinion for PCT/US2013/054268, dated Apr. 1, 2014.
International Preliminary Report on Patentability for PCT/US2013/054268 dated Feb. 19, 2015.
Bateman et al., Diagnostic accuracy of rest/stress ECG-gated Rb-82 myocardial perfusion PET: comparison with ECG-gated Tc-99m sestamibi SPECT. J Nucl Cardiol. Jan.-Feb. 2006;13(1):24-33.
Batra et al., Derivatives of 5,6-diphenylpyridazin-3-one: synthetic antimitotic agents which interact with plant and mammalian tubulin at a new drug-binding site. Cancer Res. Apr. 1986;46(4 Pt 2):1889-93.
Beckmann et al., Three-dimensional imaging of nerve tissue by x-ray phase-contrast microtomography. Biophys J. Jan. 1999;76(1 Pt 1):98-102.
Bergmann et al., Noninvasive quantitation of myocardial blood flow in human subjects with oxygen-15-labeled water and positron emission tomography. J Am Coll Cardiol. Sep. 1989;14(3):639-52.

(56) References Cited

OTHER PUBLICATIONS

Berman D.S., Germano.G, Slomka, P.J., (2012). Improvement in PET myocardial perfusion image quality and quantification with Flurpiridaz F 18. Journal of Nuclear Cardiology 19(1): S38-45.
Berman et al., (2010) Comparison of 18F-BMS747158 and 82Rb PET vs SPECT for detection of myocardial ischemia. Journal of Nuclear Cardiology 17(4): 743. Abstract #31.17.
Bousquet, J.-C. et al., "Gd-DOTA: Characterization of a New Paramagnetic Complex," Radiology, vol. 166, No. 3, pp. 693-698 (1988).
Brown, M. et al., "Delineation of myocardial oxygen utilization with carbon -11-labeled acetate," Circulation, vol. 76, No. 3, pp. 687-696 (1987).
Cao et al., Synthesis and antifeedant activity of new oxadiazolyl 3(2H)-pyridazinones. J Agric Food Chem. Jan. 1, 2003;51(1):152-5.
Case et al., Automatic registration of F-18 labeled BMS-747158 stress and rest myocardial perfusion images using 6D cross-correlation optimization. Journal of Nuclear Medicine. 2010; 51(Supplement 2): 1687.
Case et al., Imaging properties of F-18 labeled myocardial perfusion PET agent, BMS747158: dosage, acquisition time and scanner type. Journal of Nuclear Medicine. 2009;50 (Supplement 2): 418. 2 pages.
Case et al., Impact of image filtering, BMI, and gender on optimal dosage acquisition time product using a novel PET myocardial perfusion tracer: F-18 labeled Flurpiridaz. Journal of Nuclear Cardiology. 2011;18(4): 769-770. Asbtract #14.32.
Case et al., Independence of myocardial functional parameters (LVEF, EDV, and ESV) across a large range of acquisition times and measured from a novel F-18 radiotracer, Flurpiridaz F-18. Journal of Nuclear Cardiology. 2010;17(4 Supplement 1): 725-726. Abstract #9.15.
Case et al., Iterative technique for optimizing injected tracer dosage and acquisition time for F-18 labeled myocardial perfusion tracer Flurpiridaz F-18. Journal of Nuclear Cardiology. 2010;17(4): 726. Abstract # 9.17.
Chary et al., Reductive cleavage of acetals/ketals. Synthetic Communications. 1999;29(8):1257-1261.
Cherednichenko et al., NADH oxidase activity of rat cardiac sarcoplasmic reticulum regulates calcium-induced calcium release. Biophys J. Jan. 2004;86(1-Part 2of 2, suppl):241a.
Clark et al., The present role of nuclear cardiology in clinical practice. Q J Nucl Med Mol Imaging. Mar. 2005;49(1):43-58.
Clark, Fluoride ion as a base in organic synthesis. Chem. Rev. 1980; 80(5):429-52.
Crane et al., Use of a tritiated (3H) analog of flurpiridaz F18 to characterize the pharmacokinetics, metabolism and excretion in normal human subjects. AAAPS. (2011) Abstract.
Di Carli et al., Cardiac PET/CT for the evaluation of known or suspected coronary artery disease. Radiographics. Sep.-Oct. 2011;31(5):1239-54. doi: 10.1148/rg.315115056.
Di Carli et al., Cardiac PET-CT. J Thorac Imaging. Feb. 2007;22(1):101-6.
Di Carli et al., Clinical myocardial perfusion PET/CT. J Nucl Med. May 2007;48(5):783-93.
Garcia et al., What should we expect from cardiac PET? J Nucl Med. Jun. 1993;34(6):978-80.
Garrison et al., Reaction mechanisms in the radiolysis of peptides, polypeptides, and proteins. Chem Rev. 1987;87:381-98.
Ghesani et al., Role of F-18 FDG positron emission tomography (PET) in the assessment of myocardial viability. Echocardiography. Feb. 2005;22(2):165-77.
Glover et al., Journey to find the ideal PET flow tracer for clinical use: are we there yet? J Nucl Cardiol. Nov.-Dec. 2007;14(6):765-8.
Glover et al., Comparison between 201Tl and 99mTc sestamibi uptake during adenosine-induced vasodilation as a function of coronary stenosis severity. Circulation. Feb. 1, 1995;91(3):813-20.
Glover et al., Myocardial 99mTc-tetrofosmin uptake during adenosine-induced vasodilatation with either a critical or mild coronary stenosis: comparison with 201Tl and regional myocardial blood flow. Circulation. Oct. 7, 1997;96(7):2332-8.
Glover et al., Myocardial kinetics of Tc-MIBI in canine myocardium after dipyridamole. Circulation. Feb. 1990;81(2):628-37.
Gout et al., Sulfasalazine, a potent suppressor of lymphoma growth by inhibition of the xc cystine transporter: a new action for an old drug. Leukemia, vol. 15, pp. 1633-1640 (2001).
Han et al., Total Synthesis of 34-hydroxyasimicin and Its Photoactive Derivative for Affinity Labeling of the Mitochondrial Complex I. Chemistry—A European Journal, vol. 10, No. 9, pp. 2149-2158 (2004).
Higgins et al., [3H]dihydrorotenone binding to NADH: ubiquinone reductase (complex I) of the electron transport chain: an autoradiographic study. J Neurosci. Jun. 15, 1996;16(12):3807-16.
Higuchi et al., A new 18F-labeled myocardial PET tracer: myocardial uptake after permanent and transient coronary occlusion in rats. J Nucl Med. Oct. 2008;49(10):1715-22. Epub Sep. 15, 2008.
Higuchi et al., A Novel [F-18] labeled PET Tracer for the Characterization of Coronary Artery Disease: Preliminary Evaluation in a Coronary Occlusion Rat Model Circulation. 2007;116:II_658 Abstract #2947.
Hsu et al., Cardiac phantom simulation of dose injection parameters for one-day rest/stress myocardial perfusion tracer. Journal of Nuclear Medicine. 2010;51(Supplement 2): 320.
Hsu et al., Remote camera qualification (RCQ) of PET and PET/CT scanners for BMS747158 F18 myocardial perfusion phase 3 clinical trial using a standardized phantom procedure. J Nucl Med. 2011;52 (Supplement 1):54.
Huang et al., Evaluation of absolute mbf at rest and stress with Flurpiridaz F-18 injection PET in normal subjects and patients with coronary artery disease (CAD) and in two types of scanners. Journal of Nuclear Cardiology. 2011;18(4): 783-784. Abstract #26.19.
Huang et al., Rabbit myocardial 82Rb kinetics and a compartmental model for blood flow estimation. Am J Physiol. Apr. 1989;256(4 Pt 2):H1156-64.
Huang et al., Streamlined quantification of absolute MBF at rest and stress with flurpiridaz F-18 injection PET in normal subjects and patients with coronary artery disease (CAD). J Nucl Med. 2011;52 (Supplement 1):1114.
Huisman et al., First Preclinical Study of a New F-18 Labeled PET Tracer for Myocardial Perfusion Imaging Circulation. 2007;116:II_718 Abstract # 3193.
Huisman et al., Initial characterization of an 18F-labeled myocardial perfusion tracer. J Nucl Med. Apr. 2008;49(4):630-6. Epub Mar. 14, 2008.
Igarashi et al., Summary of toxicology studies with Pyridaben. J Peticide Sci. 1994;19:Technical Information.
Jiang et al., Mimicry of annonaceous acetogenins: Enantioselective syntheiss of a (4R)-hydroxy analogue having potent antitumor activity. J. Org. Chem., vol. 67, No. 10, pp. 3404-3408 (2002).
Kagan et al., Comparison of flurpiridaz F 18 and FDG for assessment of left ventricular tissue mass following myocardial infarction in rats. Journal of Nuclear Medicine;2011:52( Supp.1):1097.
Kann et al., Mitochondria and neuronal activity. Am J Physiol Cell Physiol. Feb. 2007;292(2):C641-57. Epub Nov. 8, 2006.
Knapp et al., Availability of rhenium-188 from the alumina-based tungsten-188/rhenium-188 generator for preparation of rhenium-188-labeled radiopharmaceuticals for cancer treatment. Anticancer Res. May-Jun. 1997;17(3B):1783-95.
Krivokapich et al., 13N Ammonia Myocardial Imaging at Rest and With Exercise in Normal Volunteers, Quantification of Absolute Myocardial Perfusion With Dynamic Positron Emission Tomography. Circulation, vol. 80, No. 5, pp. 1328-1337 (1989).
Kroemer, Mitochondria in cancer. Oncogene. Aug. 7, 2006;25(34):4630-2.
Latli et al., Photoaffinity radioligand for NADH:ubiquinone oxidoreductase: [S—C3H2](trifluoromethyediazirinyl-pyridaben. J. Labelled Compounds Radiopharm. 1998;41(3):191-9.
Lazewatsky et al., Development of a method for the determination of dose ratio and minimum inter-injection interval for a one-day rest-stress protocol with BMS747158 PET myocardial perfusion agent. Journal of Nuclear Medicine. 2010;51(Supplement 2):600.

(56) References Cited

OTHER PUBLICATIONS

Lazewatsky et al., Dosimetry of BMS747158, a novel 18F labeled tracer for myocardial perfusion imaging, in nonhuman primates at rest. J Nucl Med. 2008;49(Supplement 1):15p.

Lazewatsky et al., Relative defect radioactivity and perceived defect severity are proportional with flurpiridaz F18 PET myocardial perfusion imaging. J Nucl Med. 2011;52 (Supplement 1):1115.

Lee et al., Potential and practical adrenomedullary PET radiopharmaceuticals as an alternative to m-iodobenzylguanidine: m-(omega-[18F]fluoroalkyl)benzylguanidines. Bioconjug Chem. Jan.-Feb. 2004;15(1):104-11.

Lindell et al., The design and synthesis of novel inhibitors of NADH: ubiquinone oxidoreductase. Bioorganic & Medicinal Chemistry Letters, vol. 14, pp. 511-514 (2004).

Liu et al., Integrin avb3 directed radiopharmaceuticals for tumor imaging. Drugs of the Future, vol. 28, No. 6, pp. 551-564 (2003).

Maddahi et al., Comparison of F-18 labeled BMS747158 PET and Tc-99m labeled spect myocardial perfusion imaging for detection and evaluation of coronary artery disease. Journal of the American College of Cardiology. 2010;55(10A): E616.

Maddahi et al., Comparison of flurpiridaz F 18 PET injection and Tc-99m labeled SPECT myocardial perfusion imaging for identifying severity and extent of stress induced myocardial ischemia in phase 2 clinical trials. J Nucl Med. 2011;52 (Supplement 1):444.

Maddahi et al., F-18 labeled BMS747158 Pet myocardial perfusion imaging identifies more severe and extensive stress induced myocardial ischemia than Tc-99m Sestamibi SPECT. Journal of Nuclear Medicine. 2010;51(Supplement 2): 1739.

Maddahi et al., First human study of of BMS747158, a novel F-18 labeled tracer for myocardial perfusion imaging. J Nucl Med. 2008;49:70P.

Maddahi et al., Human safety, dosimetry, biodistribution, and rest-stress myocardial imaging characteristics of the new F-18 labeled BMS747158 myocardial perfusion PET tracer. European Heart Journal. 2009;11(Supplement): S89. Abstract #432.

Maddahi et al., Phase 1 Human safety, dosimetry, Biodistribution and rest/stress myocardial imaging characteristics of F18 Labeled BMS 747158. (2009) Journal of the American College of Cardiology 53(10): A297. Abstract #1054-263.

Maddahi et al., Phase 2 clinical comparison of flurpiridaz F 18 injection PET and SPECT myocardial perfusion imaging for diagnosis of coronary artery disease. J Nucl Med. 2011;52 (Supplement 1):59.

Maddahi et al., Phase 2 safety and clinical comparison of flurpiridaz F18 injection PET and SPECT myocardial perfusion imaging for diagnosis of coronary artery disease. European Heart Journal Supplements. 2011;13( Supplement A ): A45. Abstract # 197.

Maddahi et al., Phase I, First-in-Human Study of BMS747158, a Novel 18F-Labeled Tracer for Myocardial Perfusion PET: Dosimetry, Biodistribution, Safety, and Imaging Characteristics After a Single Injection at Rest. J Nucl Med. 2011;52: 1490-9.

Maddahi et al., Preliminary results of absolute quantification of rest and stress myocardial blood flow with Flurpridaz F-18 PET in normal and coronary artery disease patients in a single-center study. Journal of Nuclear Cardiology. 2010;17(4): 743. Abstract # 31.18.

Maddahi et al., Protocols for same day rest-stress PET imaging with the new F-18 labeled BMS747158 myocardial perfusion tracer. European Heart Journal. 2009;11(Supp B): S89. Abstract #433.

Maddahi et al., Same day rest-stress protocols for PET imaging with the new F-18 labeled BMS747158 myocardial perfusion tracer. Journal of Nuclear Medicine. 2009;50(Supplement 2): 1173.

Maddahi, Properties of an ideal PET perfusion tracer: New PET tracer cases and data. Journal of Nuclear Cardiology. 2012;19(Supplement 1): S30-37.

Magerstadt et al., Gd(DOTA): An Alternative to Gd(DTPA) as a T1,2 Relaxation Agent for NMR Imaging of Spectroscopy. Magnetic Resonance in Medicine, vol. 3, pp. 808-812 (1986).

Marshall et al., Kinetic Analysis of a 125I-iodorotenone as a deposited myocardial flow tracer: Comparison with 99mTc-sestamibi. Journal of Nuclear Medicine, vol. 42, No. 2, pp. 272-281 (2001).

Marshall et al., Kinetic Analysis of a 18F-fluorodihydrorotenone as a deposited myocardial flow tracer: Comparison with 291T1. Journal of Nuclear Medicine, vol. 45, No. 11, pp. 1950-1959 (2004).

Martarello et al., Synthesis and evaluation of a new fluorine-18 labeled rotenoid as a potential pet probe of mitochondrial complex I activity. Journal of Labelled Compounds and Radiopharmaceuticals, vol. 42, No. 11, pp. 1039-1051 (1999).

Miller et al., Synthesis of 11C, 18F, 15O, and 13N radiolabels for positron emission tomography. Angew Chem Int Ed Engl. 2008;47(47):8998-9033.

Mistry et al., Toxicological evaluation of BMS-747158, a PET myocardial perfusion imaging agent. The Toxicologist. 2008;102:476.

Miyoshi et al., Essential structural factors of annonaceous acetogenenins as potent inhibitors of mitochondrial complex I. Biochimica et Biophysica Acta, vol. 1365, No. 3, pp. 443-452 (1998).

Miyoshi, Structure-activity relationships of some complex I inhibitors. Biochim Biophys Acta. May 6, 1998;1364(2):236-44.

Mou et al., Preparation and biodistribution of [18F]FP2OP as myocardial perfusion imaging agent for positron emission tomography. Bioorg Med Chem. Feb. 2010;18(3):1312-20. Epub Dec. 26, 2009.

Mou et al., Synthesis and preliminary evaluation of 18F-labeled pyridaben analogues for myocardial perfusion imaging with PET. J Nucl Med. Mar. 2012;53(3):472-9. doi: 10.2967/jnumed.111.088096. Epub Feb. 2, 2012.

Mukherjee, Fluorinated benzamide neuroleptics-2. Synthesis and radiosynthesis of (S)—N-[(1-ethyl-2-pyrrolidinyl)methyl]-5-(3-[18F]fluoropropyl)-3-substituted-2-methoxybenzamides. Int J Rad Appl Instrum A. 1991;42(8):713-21. Abstract Only.

Nakanishi et al., Acetogenins as selective inhibitors of the human ovarian 1A9 tumor cell line. Journal of Medicinal Chemistry, vol. 46, No. 15, pp. 3185-3188 (2003).

Nekolla et al., Assessment of imaging properties of a new F-18 labelled flow tracer in a pig model. J Am Coll Cardiol. 2008;51:A170.

Nekolla et al., Evaluation of a new myocardial PET tracer 18F-BMS-747158-02 (18F-BMS): Comparison to 13N ammonia and validation with microspheres. J Nucl Med. 2008; 49 (Supplement 1):29P.

Nekolla et al., Evaluation of the novel myocardial perfusion positron-emission tomography tracer 18F-BMS-747158-02: comparison to 13N-ammonia and validation with microspheres in a pig model. Circulation. May 5, 2009;119(17):2333-42. Epub Apr. 20, 2009.

Nekolla et al., Novel F-18 Labeled PET Myocardial Perfusion Tracers: Bench to Bedside. Current Cardiology Reports. 2011;13: 145-150.

Nicolaou et al., Combinatorial synthesis of novel and potent inhibitors of NADH: ubiquinone oxidoreductase. Chem Biol. Dec. 2000;7(12):979-92.

Okun et al., Three classes of inhibitors share a common binding domain in mitochondrial complex I (NADH:ubiquinone oxidoreductase). J Biol Chem. Jan. 29, 1999;274(5):2625-30.

Pauwels et al., Fluorine-18-radiolabeled pharmaceuticals for imaging with positron emission tomography, excluding [18F]-fluorodeoxyglucose. Drugs of the Future. 2002;27:655-67.

Pike, PET radiotracers: crossing the blood-brain barrier and surviving metabolism. Trends Pharmacol Sci. Aug. 2009;30(8):431-40. doi: 10.1016/j.tips.2009.05.005. Epub Jul. 16, 2009.

Purohit et al., Quinazoline derivatives as MC-I inhibitors: evaluation of myocardial uptake using Positron Emission Tomography in rat and non-human primate. Bioorg Med Chem Lett. Sep. 1, 2007;17(17):4882-5. Epub Jun. 14, 2007.

Purohit et al., Synthesis and biological evaluation of pyridazinone analogues as potential cardiac positron emission tomography tracers. J Med Chem. May 22, 2008;51(10):2954-70. Epub Apr. 19, 2008.

Radeke et al., Synthesis and biological evaluation of the mitochondrial complex 1 inhibitor 2-[4-(4-fluorobutyl)benzylsulfanyl]-3-

(56) References Cited

OTHER PUBLICATIONS methylchromene-4-one as a potential cardiac positron emission tomography tracer. J Med Chem. Sep. 6, 2007;50(18):4304-15. Epub Aug. 15, 2007.

Ramsay et al., Interaction of 1-methyl-4-phenylpyridinium ion (MPP+) and its analogs with the rotenone/piericidin binding site of NADH dehydrogenase. J Neurochem. Apr. 1991;56(4):1184-90.

Ravert et al., Radiosynthesis of 3-[18F]fluoropropyl and 4-[18F]fluorobenzyl triarylphosphonium ions. J Lab Comp Radiopharm. 2004;47(8):469-76.

Ritchie et al., Guidelines for clinical use of cardiac radionuclide imaging. Report of the American College of Cardiology/American Heart Association Task Force on Assessment of Diagnostic and Therapeutic Cardiovascular Procedures (Committee on Radionuclide Imaging), developed in collaboration with the American Society of Nuclear Cardiology. J Am Coll Cardiol. Feb. 1995;25(2):521-47.

Rubin et al., The cell biology of the blood-brain barrier. Annu Rev Neurosci. 1999;22:11-28.

Runge et al., MR Imaging of Rat Brain Glioma: Gd-DTPA versus Gd-DOTA. Radiology, vol. 166, No. 3, pp. 835-838 (1988).

Santi et al., Toxicology of rotenone. Farmaco Sci. Apr. 1965;20:270-9.

Schelbert et al., N-13 ammonia as an indicator of myocardial blood flow. Circulation. Jun. 1981;63(6):1259-72.

Schuler et al., Functional coupling of PSST and ND1 subunits in NADH: ubiquinone oxidoreductase established by photoaffinity labeling. Biochimica et Biophysica Acta, vol. 1506, pp. 79-87 (2001).

Schuler et al., The insecticide target in the PSST subunit of complex I. Pest Manag Sci. Oct. 2001;57(10):932-40.

Schyler, PET tracers and radiochemistry. Ann Acad Med Singapore. Mar. 2004;33(2):146-54.

Sherif et al., Evaluation of a novel (18)F-labeled positron-emission tomography perfusion tracer for the assessment of myocardial infarct size in rats. Circulation: Cardiovascular Imaging. Mar. 2009;2(2):77-84.

Sherif et al., Evaluation of the novel PET perfusion tracer 18F BMS747158-02 for measurement of myocardial infarct size in a rat model. J Nucl Med. 2008; 49 (Supplement 1):186P.

Sherif et al., Reply: Simplified Quantification of Myocardial Flow Reserve with 18F-Flurpiridaz: Validation with Microspheres in a Pig Model. Journal of Nuclear Medicine. 2011;52(11): 1835-1836.

Sherif et al., Simplified quantification of myocardial flow reserve with flurpiridaz F-18: Validation with Microspheres in a pig model. Journal of Nuclear Medicine. 2011;52: 617-624.

Singh et al., A versatile route to 2-alkyl-/aryl-amino-3-formyl and heter-annelated-chromosones, through a facile nucleophilic substitution at C2 in 2-(N-methylanilino)-3-formylchromones. Tetrahedron. 2002;58(12):2471-80.

Sirion et al., An efficient F-18 labeling method for PET study: Huisgen 1,3-dipolar cycloaddition of bioactive substances and F-18-labeled compounds. Tetrahedron Letters. Jun. 4, 2007;48(23):3953-7.

Slomka et al., Multicenter development of normal perfusion and function limits for stress and rest flurpiridaz F-18 Cardiac Pet. Journal of Nuclear Cardiology. 2010;17(4): 725. Abstract #9.14.

Soderquist et al., Reductive cleavage of acetals and ketals with 9-borabicyclo[3.3.1]nonane†. Org Process Res Dev. 2006;10(5):1076-9.

Strauss et al., Society of Nuclear Medicine Procedure Guideline for Myocardial Perfusion Imaging. Soc. Nucl Med Pro Guide Man. Jun. 2002:9-17.

Talpade et al., In vivo labeling of mitochondrial complex I (NADH:ubiquinone oxidoreductase) in rat brain using [(3)H]dihydrorotenone. J Neurochem. Dec. 2000;75(6):2611-21.

Tamarappoo et al., Comparison of myocardial stress perfusion defect assessment using 99mTc Sestamibi SPECT vs 18F-BMS747158 PET. Journal of Nuclear Cardiology. 2010;17(4): 742. Abstract #31.14.

Tang et al., Automated commercial synthesis system for preparation of O-(2-[18F]fluoroethyl)-L-tyrosine by direct nucleophilic displacement on a resin column. J. Label Compd Radiopharm 2003; 46:661-668.

Ueno et al., Comparison of the inhibitory action of natural rotenone and its stereoisomers with various NADH-ubiquinone reductases. Eur J Biochem. Oct. 1, 1994;225(1):411-7.

Ueno et al., Structural factors of rotenone required for inhibition of various NADH-ubiquinone oxidoreductases. Biochim Biophys Acta. Sep. 30, 1996;1276(3):195-202.

Unger, Pesticide synthesis handbook. Technology and Engineering. 1996:523-4. Google books result.

Vanbrocklin et al., (F-18)fluorodihydrorotenone: Synthesis and evaluation of a mitochondrial electron transport chain (ETC) complex I probe for PET. Journal of Nuclear Medicine, vol. 35, No. 5 Suppl., p. 73P (1994).

Vanbrocklin et al., Fluorine-18 labeled dihydrorotenone analogs: preparation and evaluation of PET mitochondrial probes. Journal of Labelled Compounds and Radiopharmaceuticals, Symposium abstracts (continue in part IV). 1994; 35:217-19.

Vanbrocklin et al., Mitochondrial avid radioprobes. Preparation and evaluation of 7'(Z)-[125I]iodorotenone and 7'(Z)-[125I]iodorotenol. Nucl Med Biol. Jan. 2007;34(1):109-16. Epub Nov. 28, 2006.

Walker, The NADH: ubiquinone oxidoreductase (complex I) of respiratory chains. Quarterly Review of Biophysics, vol. 25, No. 3, pp. 253-324 (1992).

Wallace, A mitochondrial paradigm of metabolic and degenerative diseases, aging, and cancer: a dawn for evolutionary medicine. Annu Rev Genet. 2005;39:359-407.

Wang et al., Insights into amyloid-beta-induced mitochondrial dysfunction in Alzheimer disease. Free Radic Biol Med. Dec. 15, 2007;43(12):1569-73. Epub Sep. 21, 2007.

Woo et al., Automatic 3D registration of dynamic stress and rest (82)Rb and flurpiridaz F 18 myocardial perfusion PET data for patient motion detection and correction. Medical Physics. 2011;38(11): 6313-26.

Wood et al., Fenazaquin Acaricide Specific Binding Sites in NADH: Ubiquinone Oxidoreductase and Apparently the ATP Synthase Stalk. Pest Biochem Phys. Feb. 1996;54(2):135-45.

Yalamanchili et al., Mechanism of uptake and retention of F-18 BMS-747158-02 in cardiomyocytes: a novel PET myocardial imaging agent. J Nucl Cardiol. Nov.-Dec. 2007;14(6):782-8. Epub Oct. 22, 2007.

Yang et al., A new device for measuring density of jaw bones. Dentomaxillofac Radiol. Sep. 2002;31(5):313-6.

Yu et al., [18F]-RP1012: A Novel Myocardial Perfusion Imaging Agent for use with positron emission tomography (PET). Circulation Supplmement 2, 112(17), II-761, Abstract #3546, 2005.

Yu et al., A novel cardiac PET imaging agent. International Hospital Equipment and Solutions. 2009; 35(4):14-5.

Yu et al., Assessment of 18F-labeled mitochondrial complex I inhibitors as PET myocardial perfusion imaging agents in rats, rabbits, and primates. Eur J Nucl Med Mol Imaging. Jan. 2009;36(1):63-72. Epub Aug. 21, 2008.

Yu et al., BMS-747158-02: a novel PET myocardial perfusion imaging agent. Journal of Nuclear Cardiology, vol. 14. No. 6, pp. 789-98 (2007).

Yu et al., Cardiac imaging and safety evaluation of BMS747158, a novel PET myocardial perfusion imaging agent, in chronic myocardial compromised rabbits. J Nuclear Cardiology. 2010;17(4):631-6.

Yu et al., Cardiac imaging and uptake of BMS747158-02 under various experimental conditions. J Nucl Med. 2008; 49 (Supplement 1):187P.

Yu et al., Effects of Food Intake and Anesthetic on Cardiac Imaging and Uptake of BMS-747158-02 in Comparison with FDG. Journal Nuclear Cardiology. Sep.-Oct. 2009;16(5):763-8.

Yu et al., Evaluation of LMI1195, a Novel 18F-Labeled Cardiac Neuronal PET Imaging Agent, in Cells and Animal Models. Circulation: Cardiovascular Imaging 2011 4: 435-443.

Yu et al., In-vivo Assessment of Mitochondrial Complex-1 Inhibitors as Myocardial Perfusion Imaging Agents (MPIA). Circulation Supplement 2, 112 (17), II-474, Abstract #2283, 2005.

(56) References Cited

OTHER PUBLICATIONS

Yu et al., Myocardial Perfusion Imaging with 18F-Chromone Based MC-1 Inhibitors. Molecular Imaging. 2006;5(3):372-3. Abstract ID: 642 Poster board space:105.

Yu et al., The next generation of cardiac positron emission tomography imaging agents: discovery of flurpiridaz f-18 for detection of coronary disease. Seminars Nucl Med. Jul. 2011;41(4):305-13.

* cited by examiner

CONTRAST AGENTS FOR APPLICATIONS INCLUDING PERFUSION IMAGING

RELATED APPLICATIONS

This application is a continuation and claims priority to co-pending U.S. application Ser. No. 12/919,600, filed on Dec. 21, 2010, which is a national stage filing under 37 U.S.C. § 371 of international application, PCT/US2009/001247, filed Feb. 27, 2009, which claims priority under 35 U.S.C. § 119(e) to U.S. Provisional Application Ser. No. 61/067,593, filed Feb. 29, 2008, the contents of each of which are incorporated herein by reference.

FIELD OF THE INVENTION

The present invention relates to compounds comprising imaging moieties, and their use in imaging and/or diagnosing certain disorders in a subject.

BACKGROUND OF THE INVENTION

Mitochondria are membrane-enclosed organelles distributed through the cytosol of most eukaryotic cells. Mitochondria levels are elevated in tissues that require greater energy to function. Examples of such tissue include brain, central nervous system, and cancerous tissues.

Complex 1 ("MC-1") is a membrane-bound protein complex of 46 dissimilar subunits. This enzyme complex is one of three energy-transducing complexes that constitute the respiratory chain in mammalian mitochondria. This NADH-ubiquinone oxidoreductase is the point of entry for the majority of electrons that traverse the respiratory chain, eventually resulting in the reduction of oxygen to water (*Q. Rev. Biophys.* 1992, 25, 253-324).

Known inhibitors of MC-1 include deguelin, piericidin A, ubicidin-3, rolliniastatin-1, rolliniastatin-2 (bullatacin), capsaicin, pyridaben, fenpyroximate, amytal, MPP+, quinolines, and quinolones (*BBA* 1998, 1364, 222-235).

Previous work has shown that $^{18}$F-fluorodeoxyglucose (FDG) may be useful in imaging cancer in a subject. For example elevated demand by tissues for energy can preferentially retain $^{18}$F-fluorodeoxyglucose in cancer cells. However, due to the mechanism of uptake for $^{18}$F-fluorodeoxyglucose, not all cancers are "PET active," in the use of FDG.

SUMMARY OF THE INVENTION

The present invention relates to the recognition that interrupting the normal function of mitochondria may advantageously concentrate certain compounds in the mitochondria, and, hence, in mitochondria-rich tissue. As described herein, such compounds may be labeled with at least one imaging moiety, such that mitochondrial build-up may be determined, thereby providing valuable diagnostic markers for brain and cancer imaging. For purposes of this specification, a compound is referred to as "labeled" when an imaging moiety is attached to (e.g. bound to) the compound.

In some embodiments, the present invention provides methods of imaging at least a portion of the brain (e.g., brain tissue), central nervous system, or a cancer, comprising administering to a subject a contrast agent which comprises an imaging moiety and a compound bound to the imaging moiety, the compound selected from pyridaben, fenazaquin, a pyridaben analog, a pyridimifen analog, a tebufenpyrad analog, and an fenazaquin analog; and scanning the subject using diagnostic imaging to produce an image of at least a portion of the brain, central nervous system (CNS), or a cancer (e.g., a non-CNS cancer). The image may be used in the diagnosis of a subject, or to determine the stage of a disease.

In some embodiments, the present invention provides a contrast agent comprising an imaging moiety and a compound bound to the imaging moiety, the compound selected from pyridaben, fenazaquin, a pyridaben analog, a pyridimifen analog, a tebufenpyrad analog, and a fenazaquin analog. In some embodiments, the present invention provides a contrast agent comprising an imaging moiety and a compound bound to the imaging moiety, the compound selected from pyridaben, fenazaquin, a pyridaben analog, and a fenazaquin analog. In some embodiments, the imaging moiety is a radioisotope for nuclear medicine imaging.

In some embodiments, the radioisotope for nuclear medicine imaging is $^{11}$C, $^{13}$N, $^{18}$F, $^{123}$I, $^{125}$I. In one set of embodiments, the imaging moiety is $^{18}$F.

In some embodiments, the contrast agent comprises an imaging moiety and a compound bound to the imaging moiety, the compound selected from pyridaben, fenazaquin, a deguelin analog, a pyridaben analog, a pyridimifen analog, a tebufenpyrad analog, and a fenazaquin analog wherein the contrast agent has a structure as in Formula (I),

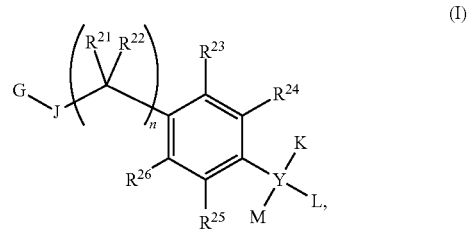

(I)

wherein:

G is

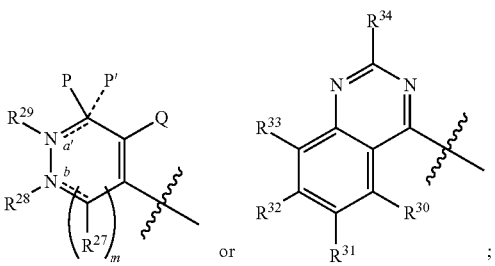

m is 0 or 1;

$\underline{a}$ and $\underline{b}$ each independently represent a single or a double bond;

$R^{27}$, $R^{30}$, $R^{31}$, $R^{32}$, $R^{33}$, and $R^{34}$ are independently selected from hydrogen, alkyl, optionally substituted, and an imaging moiety;

$R^{28}$, when present, is selected from hydrogen and alkyl, optionally substituted, provided that when $\underline{b}$ is a double bond, $R^{28}$ is absent;

$R^{29}$, when present, is alkyl, optionally substituted, provided that when $\underline{a}$ is a double bond, $R^{29}$ is absent;

P is

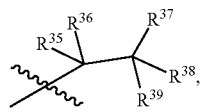

wherein $R^{35}$, $R^{36}$, $R^{37}$, $R^{38}$, and $R^{39}$ are independently selected from hydrogen, alkyl, optionally substituted, and an imaging moiety;

P', when present, is hydrogen, provided that when ⁝a⁝ is a double bond, P' is absent;

or, P and P' together form an oxo group;

Q is halo or haloalkyl;

J is selected from $N(R^{27})$, S, O, C(=O), C(=O)O, $NHCH_2CH_2O$, a bond, and $C(=O)N(R^{27})$;

K and L, when present, are independently selected from hydrogen, alkoxyalkyl, alkyloxy, aryl, alkyl, heteroaryl, and an imaging moiety, each of which is optionally substituted;

M is selected from hydrogen, alkoxyalkyl, alkyloxy, aryl, alkyl, heteroaryl, and an imaging moiety, each of which is optionally substituted, or L and M, together with the atom to which they are attached, form a ring, optionally substituted;

n is 0, 1, 2, or 3;

$R^{21}$, $R^{22}$, $R^{23}$, $R^{24}$, $R^{25}$, and $R^{26}$ are independently selected from hydrogen, alkyl, optionally substituted, and an imaging moiety, each of which is optionally substituted; and Y is selected from a bond, carbon, and oxygen; provided that when Y is a bond, K and L are absent and M is selected from aryl and heteroaryl, each of which is optionally substituted; and provided that when Y is oxygen, K and L are absent and M is selected from hydrogen, alkoxyalkyl, aryl, alkyl, and heteroaryl, each of which is optionally substituted, wherein at least one imaging moiety is present in Formula (I).

In one set of embodiments, K and L, when present, are independently selected from hydrogen, alkoxyalkyl, alkyloxy, aryl, heteroaryl, and an imaging moiety, each of which is optionally substituted. In one set of embodiments, M is selected from hydrogen, alkoxyalkyl, alkyloxy, aryl, heteroaryl, and an imaging moiety, each of which is optionally substituted. In one set of embodiments, L and M, together with the atom to which they are attached, form a three- or four-membered carbocyclic ring, optionally substituted.

In one set of embodiments, J is selected from $N(R^{27})$, S, O, C(=O), C(=O)O, $NHCH_2CH_2O$, a bond, and $C(=O)N(R^{27})$, provided that, when J is C(=O)O, the carbon atom of J is attached to G and the oxygen atom of J is attached to the carbon substituted with $R^{21}$ and $R^{22}$; when J is $NHCH_2CH_2O$, the nitrogen atom of J is attached to G and the oxygen atom of J is attached to the carbon substituted with $R^{21}$ and $R^{22}$; and, when J is $C(=O)N(R^{27})$, the carbon atom of J is attached to G and the nitrogen atom of J is attached to the carbon substituted with $R^{21}$ and $R^{22}$.

In one set of embodiments, $R^{29}$ is $C_1$-$C_6$ alkyl. For example, $C_1$-$C_6$ alkyl may be tert-butyl.

In one set of embodiments, $R^{28}$ is $C_1$-$C_6$ alkyl. For example, $C_1$-$C_6$ alkyl may be methyl.

In any of the foregoing embodiments, any group may be optionally substituted with an imaging moiety. In some embodiments, K, L, or M are independently alkoxyalkyl, alkyloxy, aryl, or heteroaryl, optionally substituted with an imaging moiety. In one set of embodiments, K, L, or M are independently alkoxyalkyl, optionally substituted with an imaging moiety.

In one set of embodiments, M is alkoxyalkyl, optionally substituted with an imaging moiety.

In some embodiments, the contrast agent comprises an imaging moiety and a compound bound to the imaging moiety, the compound selected from deguelin, pyridaben, pyridimifen, tebufenpyrad, fenazaquin, a deguelin analog, a pyridaben analog, a pyridimifen analog, a tebufenpyrad analog, and an fenazaquin analog wherein the contrast agent has a structure as in Formula (II),

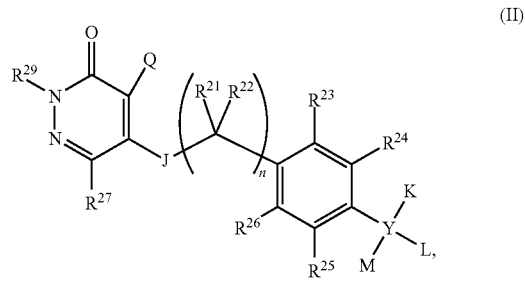

wherein:

J is selected from $N(R^{27})$, S, O, C(=O), C(=O)O, $NHCH_2CH_2O$, a bond, or $C(=O)N(R^{27})$;

K and L, when present, are independently selected from hydrogen, alkoxyalkyl, alkyloxy, aryl, alkyl, heteroaryl, and an imaging moiety, each of which is optionally substituted;

M is selected from hydrogen, alkoxyalkyl, alkyloxy, aryl, alkyl, heteroaryl, and an imaging moiety, each of which is optionally substituted, or L and M, together with the atom to which they are attached, form a ring, optionally substituted;

Q is halo or haloalkyl;

n is 0, 1, 2, or 3;

$R^{21}$, $R^{22}$, $R^{23}$, $R^{24}$, $R^{25}$, $R^{26}$, and $R^{27}$ are independently selected from hydrogen, alkyl, optionally substituted, and an imaging moiety;

$R^{29}$ is alkyl, optionally substituted; and

Y is selected from a bond, carbon, and oxygen; provided that when Y is a bond, K and L are absent and M is selected from aryl and heteroaryl, each of which is optionally substituted; and provided that when Y is oxygen, K and L are absent and M is selected from hydrogen, alkoxyalkyl, aryl, alkyl, and heteroaryl, each of which is optionally substituted, wherein at least one imaging moiety is present in Formula (II).

In one set of embodiments, K and L, when present, are independently selected from hydrogen, alkoxyalkyl, alkyloxy, aryl, heteroaryl, and an imaging moiety, each of which is optionally substituted. In one set of embodiments, M is selected from hydrogen, alkoxyalkyl, alkyloxy, aryl, heteroaryl, and an imaging moiety, each of which is optionally substituted. In one set of embodiments, L and M, together with the atom to which they are attached, form a three- or four-membered carbocyclic ring, optionally substituted.

In one set of embodiments, J is selected from $N(R^{27})$, S, O, C(=O), C(=O)O, $NHCH_2CH_2O$, a bond, and C(=O) $N(R^{27})$, provided that, when J is C(=O)O, the carbon atom of J is attached to G and the oxygen atom of J is attached to the carbon substituted with $R^{21}$ and $R^{22}$; when J is $NHCH_2CH_2O$, the nitrogen atom of J is attached to G and the oxygen atom of J is attached to the carbon substituted with $R^{21}$ and $R^{22}$; and, when J is $C(=O)N(R^{27})$, the carbon atom of J is attached to G and the nitrogen atom of J is attached to the carbon substituted with $R^{21}$ and $R^{22}$.

In one set of embodiments, J is O and $R^{29}$ is $C_1$-$C_6$ alkyl. For example, $C_1$-$C_6$ alkyl may be tert-butyl.

In any of the foregoing embodiments, any group may be optionally substituted with an imaging moiety. In some embodiments, K, L, or M are independently alkoxyalkyl, alkyloxy, aryl, or heteroaryl, optionally substituted with an imaging moiety. In one set of embodiments, K, L, or M are independently alkoxyalkyl, optionally substituted with an imaging moiety.

In one set of embodiments, M is alkoxyalkyl, optionally substituted with an imaging moiety.

In one set of embodiments, the contrast agent is selected from the following group:

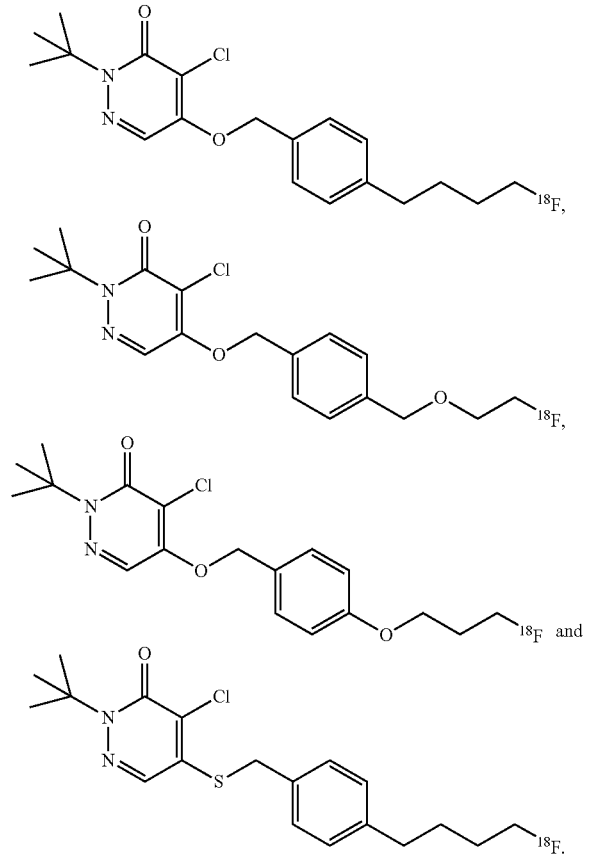

In a particular embodiment, the contrast agent is

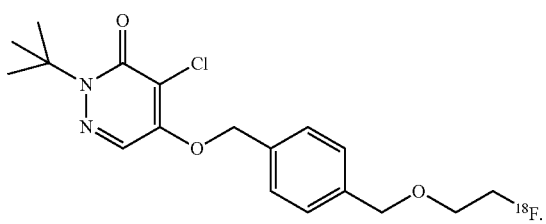

In some embodiments, the contrast agent comprises an imaging moiety and a compound bound to the imaging moiety, the compound selected from deguelin, pyridaben, pyridimifen, tebufenpyrad, fenazaquin a deguelin analog, a pyridaben analog, a pyridimifen analog, a tebufenpyrad analog, and an fenazaquin analog wherein the contrast agent has a structure as in Formula (III),

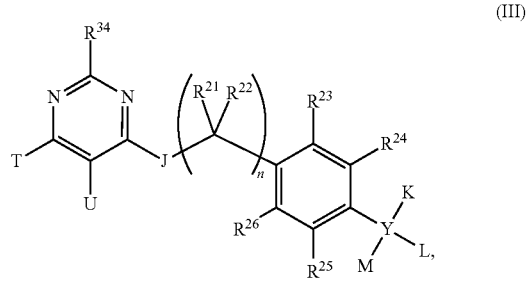

wherein:

J is selected from $N(R^{27})$, S, O, $C(=O)$, $C(=O)O$, $NHCH_2CH_2O$, a bond, and $C(=O)N(R^{27})$;

K is selected from hydrogen, alkoxyalkyl, alkyloxy, aryl, alkyl, heteroaryl, and an imaging moiety, each of which is optionally substituted;

L, when present, is selected from hydrogen, alkoxyalkyl, alkyloxy, aryl, alkyl, heteroaryl, and an imaging moiety, each of which is optionally substituted;

M, when present, is selected from hydrogen, alkoxyalkyl, alkyloxy, aryl, alkyl, heteroaryl, and an imaging moiety, each of which is optionally substituted, or L and M, together with the atom to which they are attached, form a ring, optionally substituted;

T and U are independently selected from hydrogen, alkoxy, alkoxyalkyl, alkyl, halo, and an imaging moiety, each of which is optionally substituted or, T and U, together with the carbon atoms to which they are attached, form a five- to six-membered aromatic or non-aromatic ring containing zero to two heterotoms selected from oxygen, nitrogen, and sulfur, wherein said ring is optionally substituted with one, two, or three substituents independently selected from alkyl, optionally substituted, and an imaging moiety;

n is 0, 1, 2, or 3; and $R^{21}$, $R^{22}$, $R^{23}$, $R^{24}$, $R^{25}$, $R^{26}$, $R^{27}$, and $R^{34}$ are independently selected from hydrogen, alkyl, optionally substituted, and an imaging moiety; and Y is selected from a bond, carbon, and oxygen, provided that when Y is a bond, K and L are absent and M is selected from aryl and heteroaryl, each of which is optionally substituted; and provided that when Y is oxygen, K and L are absent and M is selected from hydrogen, alkoxyalkyl, aryl, alkyl, and heteroaryl, each of which is optionally substituted, wherein at least one imaging moiety is present in Formula (III).

In one set of embodiments, K and L, when present, are independently selected from hydrogen, alkoxyalkyl, alkyloxy, aryl, heteroaryl, and an imaging moiety, each of which is optionally substituted. In one set of embodiments, M is selected from hydrogen, alkoxyalkyl, alkyloxy, aryl, heteroaryl, and an imaging moiety, each of which is optionally substituted. In one set of embodiments, L and M, together with the atom to which they are attached, form a three- or four-membered carbocyclic ring, optionally substituted.

In one set of embodiments, J is selected from $N(R^{27})$, S, O, $C(=O)$, $C(=O)O$, $NHCH_2CH_2O$, a bond, and $C(=O)$ N(R$^{27}$), provided that, when J is C(=O)O, the carbon atom of J is attached to G and the oxygen atom of J is attached to the carbon substituted with R$^{21}$ and R$^{22}$; when J is NHCH$_2$CH$_2$O, the nitrogen atom of J is attached to G and the oxygen atom of J is attached to the carbon substituted with R$^{21}$ and R$^{22}$; and, when J is C(=O)N(R$^{27}$), the carbon atom of J is attached to G and the nitrogen atom of J is attached to the carbon substituted with R$^{21}$ and R$^{22}$.

In one set of embodiments, J is O.

In any of the foregoing embodiments, any group may be optionally substituted with an imaging moiety. In some embodiments, K, L, or M are independently alkoxyalkyl, alkyloxy, aryl, or heteroaryl, optionally substituted with an imaging moiety. In one set of embodiments, K, L, or M are independently alkoxyalkyl, optionally substituted with an imaging moiety.

In one set of embodiments, M is alkoxyalkyl, optionally substituted with an imaging moiety.

In some embodiments, the contrast agent is selected from the following group:

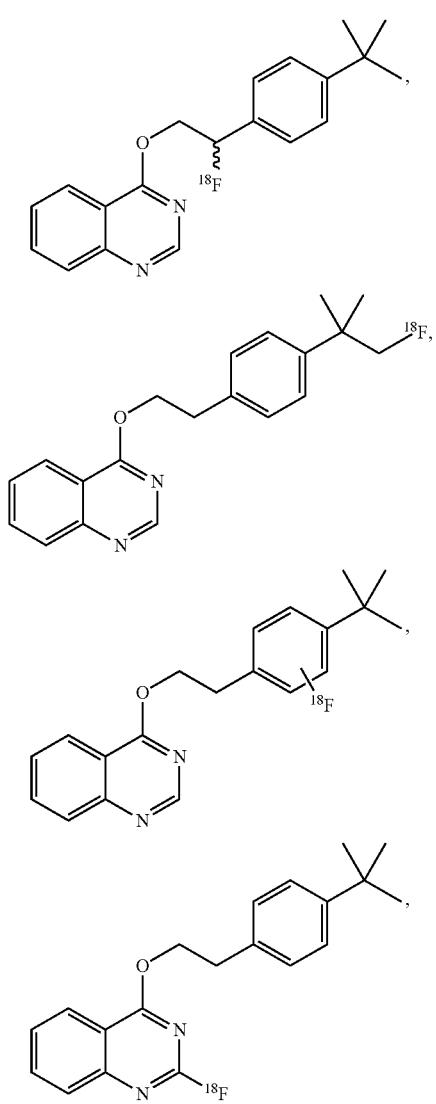

-continued

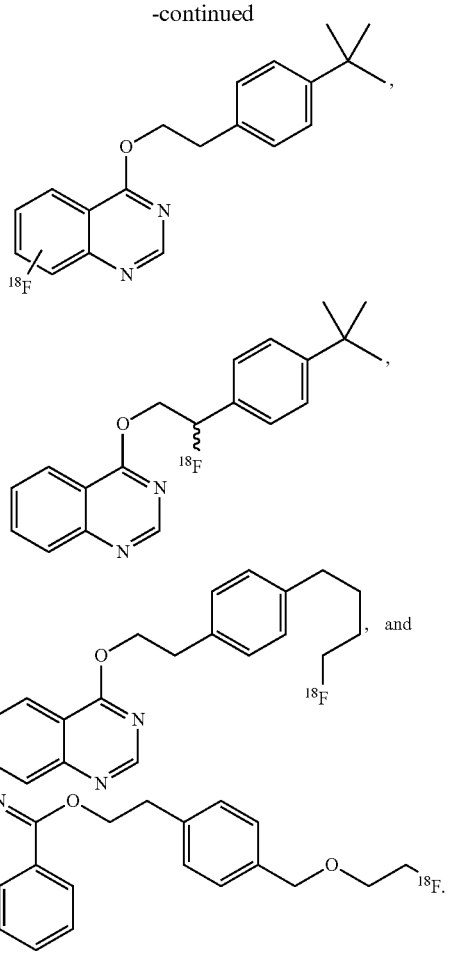

In any of the foregoing aspects and embodiments, an alkyl group may be C$_{1-20}$ alkyl, C$_{1-10}$ alkyl, or C$_{1-6}$ alkyl, optionally substituted. In some embodiments, the alkyl group is C$_{1-6}$ alkyl, optionally substituted. In some embodiments, the alkyl group is C$_{1-6}$ alkyl, optionally substituted with an imaging moiety.

In any of the forgoing aspects and embodiments, the contrast agent may be provided in the presence of a pharmaceutically acceptable salt, as disclosed herein.

In any of the forgoing aspects and embodiments, the contrast agent may be provided in the presence of a counterion, or, in the absence of a counterion (e.g., as a free base).

In some embodiments, the present invention provides methods for synthesizing any of the foregoing contrast agents according to the methods described herein. In some embodiments, the method may comprise reacting a compound with an imaging moiety precursor to form a contrast agent. In another embodiment, the method may comprise reacting an intermediate molecule to produce a contrast agent of the invention. In some embodiments, the method may further comprise isolating and/or purifying the intermediate molecule and/or contrast agent. The method may also comprise characterization of the intermediate molecule and/or contrast agent.

In some embodiments, the present invention also provides methods for medical imaging; intravenous use in imaging; imaging at least a portion of the brain, central nervous system, or a cancer of a subject; infusion or injection; delivering an imaging agent to the brain or a tumor; imaging perfusion in a body region or structure (e.g., brain, CNS, tumor); determining the level of mitochondria and/or mitochondrial density in a subject or portion of a subject; diagnosing a disease in a subject, including diagnosing the onset, progression, and/or regression of a disease; determining the stage of a disease in a subject; passing a contrast agent of the invention through the blood brain barrier of a subject; monitoring the accumulation of a contrast agent of the invention in the brain of a subject; or treating a tumor, such as a solid tumor. In some embodiments, methods of the invention can be used to assess efficacy of a treatment, for example, the brain, CNS, or a cancer can be visualized using contrast agents of the invention before, during, and/or after treatment of a condition affecting the brain, CNS, or cancer of a subject. The method may comprise administering a contrast agent as described herein to a subject. In some embodiments, the method comprises passing a contrast agent of the invention through the blood brain barrier of a subject. In some embodiments, the method comprises monitoring the accumulation of a contrast agent of the invention in the brain of a subject. All features disclosed in the specification may be used in combination with such methods.

In some embodiments, the present invention provides pharmaceutical compositions for medical imaging; intravenous use in imaging; imaging at least a portion of the brain, central nervous system, or a cancer of a subject; infusion or injection; delivering an imaging agent to the brain or a tumor; imaging perfusion in a body region or structure (e.g., brain, CNS, tumor); determining the level of mitochondria and/or mitochondrial density in a subject or portion of a subject; diagnosing a disease in a subject, including diagnosing the onset, progression, and/or regression of a disease; determining the stage of a disease in a subject; passing a contrast agent of the invention through the blood brain barrier of a subject; monitoring the accumulation of a contrast agent of the invention in the brain of a subject; or treating a tumor, such as a solid tumor. In some embodiments, the pharmaceutical composition comprises a contrast agents as described herein, and one or more pharmaceutically acceptable carriers, additives, and/or diluents. All features disclosed in the specification may be used in combination with such pharmaceutical compositions.

In some embodiments, the present invention relates to the use of any of the contrast agents described herein in the preparation of a medicament for medical imaging; intravenous use in imaging; imaging at least a portion of the brain, central nervous system, or a cancer of a subject; infusion or injection; delivering an imaging agent to the brain or a tumor; imaging perfusion in a body region or structure (e.g., brain, CNS, tumor); determining the level of mitochondria and/or mitochondrial density in a subject or portion of a subject; diagnosing a disease in a subject, including diagnosing the onset, progression, and/or regression of a disease; determining the stage of a disease in a subject; passing a contrast agent of the invention through the blood brain barrier of a subject; monitoring the accumulation of a contrast agent of the invention in the brain of a subject; or treating a tumor, such as a solid tumor. Any of the uses described herein may comprise the use of a contrast agent of the present invention. All features disclosed in the specification may be used in combination with such uses. In some embodiments, the present invention provides methods of treating a patient. The method may comprise the steps of administering to the patient a contrast agent as in any foregoing embodiments; and acquiring an image of a site of concentration of the contrast agent in the patient by a diagnostic imaging technique.

The present invention also provides method for acquiring an image, or constructing an image, of at least a portion of the brain, central nervous system, or a cancer of a subject.

Any of the foregoing aspects and embodiments may comprise contacting at least a portion of the brain, central nervous system, or a cancer of a subject with a contrast agent of the invention. In certain embodiments, the contacting may occur via administration of the contrast agent to the subject. In one set of embodiments, the contacting may occur via intravenous administration of the contrast agent to the subject.

In any of the foregoing aspects and embodiments, the disease may be a CNS disorder or condition, as described herein.

In any of the foregoing aspect and embodiments, the subject can be otherwise free of indications for perfusion imaging, such as myocardial perfusion imaging, for example.

Other aspects of the invention may include suitable combinations of embodiments and aspects disclosed herein.

DETAILED DESCRIPTION

Figure 1A:
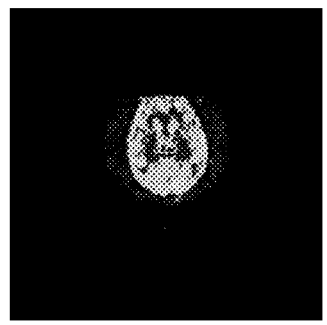
FIG. 1A shows representative images of the transverse plane of a nonhuman primate brain, with 2-tert-butyl-4-chloro-5-[4-(2-[$^{18}$F]fluoro-ethoxymethyl)-benzyloy]-2H-pyridazin-3-one in a normal NHP, where the whiter portions indicate localization of the contrast agent.

The present invention generally relates to methods for using contrast agents in imaging including perfusion imaging. In some embodiments, methods of the invention may be useful in imaging a location within a subject (e.g., mammal), including the brain, central nervous system, cancer, or portions thereof. Some embodiments of the invention may provide contrast agents, and related methods, that are selective for high energy demand tissues within a subject, in addition to a broad uptake mechanism. In some cases, contrast agents and methods described herein advantageously exhibit high avidity for an intracellular target with a relatively low off rate, which may be useful in targeting processes associated with mitochondria.

Imaging Moieties

Examples of nuclear medicine contrast agents suitable for use in the present invention include, but are not limited to, $^{11}$C, $^{13}$N, $^{18}$F, $^{123}$I, and $^{125}$I. In some cases, $^{11}$C-Palmitate may be used to probe fatty acid oxidation and $^{11}$C-acetate may be used to assess oxidative metabolism in the myocardium (*Circulation* 1987, 76, 687-696). Agents based on $^{18}$F may, in some cases, be useful as imaging agents for hypoxia and cancer (*Drugs of the Future* 2002, 27, 655-667). In one set of embodiments, the imaging moiety employed in contrast agents of the present invention is $^{18}$F. In some embodiments, imaging moieties of the present invention may comprise one or more X-ray absorbing or "heavy" atoms having an atomic number of 20 or greater. In some cases, the contrast agent may further comprise an optional linking moiety, L, positioned between the parent molecular moiety and one or more X-ray absorbing atoms. A non-limiting example of a heavy atom used as X-ray contrast agents is iodine.

Some embodiments of the invention may be useful in imaging a cancer present within a subject. Many malignant cancers may be characterized by rapid undifferentiated cell growth. The energy to facilitate this growth is high, but therapeutic interruption of energy consumption may be fatal to the subject. Some embodiments of the invention may provide the ability to image such energy consumption on a tracer level to provide a tomography of high-energy demand tissues. Additionally, methods of the invention allow for the imaging of primary tumors as well as metastatic neoplasia.

In some cases, methods for imaging central nervous system tissue, which consumes a disproportionate amount of energy, are provided. The blood-brain barrier (BBB) is a physical entity that can prevent the indiscriminate passage of agents into the brain. Current agents that can image mitochondrial density are lipophilic monocations, and are typically excluded by the BBB from CNS uptake. In some cases, methods described herein provide agents that are capable of selectively imaging brain tissue and crossing the blood brain barrier. Such methods may be useful in imaging the topography and blood flow to the brain, as well as perfusion imaging in the brain.

Generally, the contrast agents described herein are capable of imaging and mapping mitochondrial density and function in tissues. Mitochondrial function has been indicated as causative or correlative in Alzheimer' Disease (AD; Wang, et al. *Free Radical Biology and Medicine,* 2007, 43, 1569-1573, incorporated herein by reference in its entirety), Parkinson's Disease (Higgin and Greenamyre, *Journal of Neuroscience,* 1996, 16(12), 3807-3816, incorporated herein by reference in its entirety), as well as neuronal dysfunction and temporal lobe epilepsy (Kann and Kovacs, *Am. J. Physiol. Cell Physiol.* 2007, 292, C641-C657, incorporated herein by reference in its entirety). Agents such as those described herein can be used for the imaging of disease diagnosis, including, but not limited to, onset, progression, regression, and staging.

In some embodiments, the contrast agent comprises an imaging moiety and a compound bound to the imaging moiety. The imaging agent may be bound to the compound via a bond, such as a covalent bond, an ionic bond, a hydrogen bond, a dative bond (e.g. complexation or chelation between metal ions and monodentate or multidentate ligands), or the like. In this non-limiting example, the imaging agent may be a $^{18}$F atom covalently bound to a compound. The compound can be selected from, for example, pyridaben, fenazaquin, a pyridaben analog, a pyridimifen analog, a tebufenpyrad analog, and an fenazaquin analog.

Methods of Synthesizing Contrast Agents

Typically, contrast agents described herein may be synthesized by reacting at least a first component and a second component, such that a bond is formed therebetween. For example, $^{18}$F labeled compounds may be synthesized by reacting two components via $S_n2$ displacement of an appropriate leaving group associated with at least one component. Examples of such leaving groups include sulfonic acid esters such as toluenesulfonate (tosylate, TsO—), methanesulfonate (mesylate, MsO—), or trifluoromethanesulfonate (triflate, TfO—). The leaving group may also be a halide, a phosphineoxide (via Mitsunobu reaction), or an internal leaving group (such as an epoxide or cyclic sulfate). In some embodiments, such compounds can be synthesized from highly activated, dry $K^{18}F$, that is made more reactive by the addition of potassium sequestering cryptands such as krytofix[2.2.2]. Purification is generally performed via salt removal by reverse-phase chromatography (SepPak™).

Representative methods of making the contrast agents are described in the following examples. The foregoing chemical transformations may be conducted using techniques which would be readily apparent to one of ordinary skill in the art, in combination with the teachings described herein. In some cases, methods of synthesizing the contrast agents may include the use of one or more reaction solvents. Representative reaction solvents include, for example, DMF, NMP, DMSO, THF, ethyl acetate, dichloromethane, and chloroform. The reaction solution may be kept neutral or basic by the addition of an amine such as triethylamine or DIEA. In some cases, the chemical transformations (e.g., reactions) may be carried out at ambient temperatures and protected from oxygen and water with a nitrogen, argon or helium atmosphere.

In some embodiments, temporary protecting groups may be used to prevent other reactive functionality, such as amines, thiols, alcohols, phenols, and carboxylic acids, from participating or interfering in the reaction. Representative amine protecting groups include, for example, tert-butoxycarbonyl and trityl (removed under mild acidic conditions), Fmoc (removed by the use of secondary amines such as piperidine), and benzyloxycarbonyl (removed by strong acid or by catalytic hydrogenolysis). The trityl group may also used for the protection of thiols, phenols, and alcohols. In certain embodiments the carboxylic acid protecting groups include, for example, tert-butyl ester (removed by mild acid), benzyl ester (usually removed by catalytic hydrogenolysis), and alkyl esters such as methyl or ethyl (usually removed by mild base). All protecting groups may be removed at the conclusion of synthesis using the conditions described above for the individual protecting groups, and the final product may be purified by techniques which would be readily apparent to one of ordinary skill in the art, in combination with the teachings described herein.

Use of Contrast Agents

The contrast agents of the present invention may be used in methods of imaging, including methods of imaging in a subject. For example, the method may comprise administering the contrast agent to the subject by injection (e.g., intravenous injection), infusion, or any other known method, and imaging the area of the subject wherein an event of interest is located.

The useful dosage to be administered and the particular mode of administration will vary depending upon such factors as age, weight, and particular region to be imaged, as well as the particular contrast agent used, the diagnostic use contemplated, and the form of the formulation, for example, suspension, emulsion, microsphere, liposome, or the like, as will be readily apparent to those of ordinary skill in the art.

Typically, dosage is administered at lower levels and increased until the desirable diagnostic effect (e.g., production of an image) is achieved. In one embodiment, the above-described contrast agents may be administered by intravenous injection, usually in saline solution, at a dose of about 0.1 to about 100 mCi per 70 kg body weight (and all combinations and subcombinations of dosage ranges and specific dosages therein), or, in some embodiments, at a dose of about 0.5 to about 50 mCi. Imaging is performed using techniques well known to the ordinarily skilled artisan.

In some cases, for use as nuclear medicine contrast agents, the compositions of the present invention, dosages, administered by intravenous injection, may be in the range from about 0.5 µmol/kg to about 1.5 mmol/kg (and all combinations and subcombinations of dosage ranges and specific dosages therein), and, in some embodiments, about 0.8 µmol/kg to about 1.2 mmol/kg.

Another aspect of the present invention provides diagnostic kits for the preparation of diagnostic agents for determining (e.g., detecting), imaging, and/or monitoring at least a portion of the brain, central nervous system, or cancer. Diagnostic kits of the present invention may comprise one or more vials containing a sterile, non-pyrogenic, formulation comprising a predetermined amount of a reagent (e.g., contrast agent precursor) of the present invention, and optionally other components such as chelating agents, solvents, buffers, neutralization aids, lyophilization aids, stabilization aids, solubilization aids and bacteriostats, as described more fully below.

Some non-limiting examples of buffers useful in the preparation of contrast agents and kits include, for example, phosphate, citrate, sulfosalicylate, and acetate buffers. A more complete list can be found in the United States Pharmacopoeia.

Some non-limiting examples of lyophilization aids useful in the preparation of contrast agents and kits include, for example, mannitol, lactose, sorbitol, dextran, FICOLL® polymer, and polyvinylpyrrolidine (PVP).

Some non-limiting examples of stabilization aids useful in the preparation of contrast agents and kits include, for example, ethanol, ascorbic acid, ethanol, cysteine, monothioglycerol, sodium bisulfite, sodium metabisulfite, gentisic acid, and inositol.

Some non-limiting examples of solubilization aids useful in the preparation of contrast agents and kits include, for example, ethanol, glycerin, polyethylene glycol, propylene glycol, polyoxyethylene sorbitan monooleate, sorbitan monoloeate, polysorbates, poly(oxyethylene)-poly(oxypropylene)-poly(oxyethylene) block copolymers ("Pluronics®") and lecithin.

Some non-limiting examples of bacteriostats useful in the preparation of contrast agents and kits include, for example, benzyl alcohol, benzalkonium chloride, chlorobutanol, and methyl, propyl, or butyl paraben.

A component in a diagnostic kit of the invention can also serve more than one function. For example, a solubilization aid may serve as a stabilizer.

Many geometric isomers of olefins, C=N double bonds, and the like can be present in the compounds described herein, and all such stable isomers are contemplated in the present invention.

For the sake of simplicity, connection points ("—") are not depicted. When an atom or compound is described to define a variable, it is understood that it is intended to replace the variable in a manner to satisfy the valency of the atom or compound. For example, if a variable "A" was identified as "$C(R^{80})=C(R^{80})$," both carbon atoms would form a part of the chain in order to satisfy their respective valences.

When any variable occurs more than one time in any substituent or in any formula, its definition in each occurrence is independent of its definition at every other occurrence. Thus, for example, if a group, or plurality of groups, is shown to be substituted with 0-2 $R^{80}$, then said group(s) may optionally be substituted with up to two $R^{80}$, and $R^{80}$ at each occurrence in each group is selected independently from the defined list of possible $R^{80}$. Also, by way of example, for the group $—N(R^{81})_2$, each of the two $R^{81}$ substituents on N is independently selected from the defined list of possible $R^{81}$. Combinations of substituents and/or variables are permissible only if such combinations result in stable compounds. When a bond to a substituent is shown to cross the bond connecting two atoms in a ring, then such substituent may be bonded to any atom on the ring.

Imaging Methods for Detecting Cancer and CNS Disorders and Conditions

Imaging methods of the invention can be used to diagnose and assess cancer and CNS disorders or conditions based on the determination of levels and/or density of mitochondria in tissues, tissue regions, and subjects through in vivo imaging. Determination of levels or mitochondria and/or mitochondrial density in tissues in a subject permits the diagnosis and assessment of disorders associated with altered levels of mitochondria or mitochondrial density. Differences in levels of mitochondria and/or mitochondrial density in tissues of a subject compared to levels of mitochondrial and/or mitochondrial density in normal tissues (e.g. non-diseased) tissues can be used to diagnose or to aid in the diagnosis in the subject of disorders or conditions that exhibit (e.g., are associated with) altered levels of mitochondria and/or mitochondrial density. Particular types of disorders and conditions that can be assessed using imaging methods of the invention include cancer and CNS disorders and conditions. Imaging methods of the invention may be used in diagnostic methods alone or in conjunction with other diagnostic methods known in the art. One aspect of the present invention relates to the use of contrast agent comprising an imaging moiety and a compound selected from pyridaben, fenazaquin, a pyridaben analog, a pyridimifen analog, a tebufenpyrad analog, or a fenazaquin analog for detecting mitochondrial levels in a subject. This method involves administering to a subject a contrast agent that localizes in mitochondria, thus permitting detection in the subject of regions or tissues with altered or abnormal levels of mitochondria.

Methods of the invention can be used to assess or screen patients for diseases associated with the presence of increased or decreased levels of mitochondrial density in tissues. As used herein, the term "increased" means higher, for example higher versus a control level. As used herein, the term "decreased" means lower, for example decreased versus a control level. Methods of the invention may be used to identify the status of disorders associated with abnormal levels of mitochondria in tissues or regions. The amount of mitochondria in a tissue or region, as compared to a control, can be used to determine the presence or absence of a particular CNS disorder or cancer. Methods of the invention can be used to obtain useful prognostic information by providing an indicator of a CNS disorder or cancer in a subject, which can be used to select a therapy for the subject.

Imaging methods of the invention can be used to detect levels of mitochondria and/or mitochondrial density in subjects already diagnosed as having cancer or a CNS disorder or condition. In other instances, methods of the invention can be used to obtain measurements that provide a diagnosis or aid in providing a diagnosis of a cancer or a CNS disorder or condition. In some instances, a subject may be already be undergoing drug therapy for cancer or for a CNS disorder or condition, while in other instances a subject may be without present cancer therapy or therapy for a CNS disorder or condition. In some embodiments, the method can be used to assess efficacy of a treatment. For example, the brain, CNS, or a cancer can be visualized using contrast agents of the invention before, during, and/or after treatment of a condition affecting the brain, CNS, or cancer of a subject.

According to the present invention, some subjects may be free of symptoms otherwise calling for treatment with a particular therapy, and imaging methods of the invention may identify the subject as needing treatment. This means that absent the use of the imaging methods of the invention to assess levels of mitochondria and/or mitochondrial density, the subject would not according to convention as of the date of the filing of the present application have symptoms calling for treatment with a particular therapy. As a result of measuring the level of mitochondria and/or mitochondrial density of tissues or body regions of the subject using methods of the invention, the subject becomes a candidate for treatment with a particular therapy. Thus, for example, a subject determined using imaging methods of the invention, to have an above-normal level of mitochondria and/or mitochondrial density in a tissue or body region may be determined to have cancer and these results may be used to selected or aid in the selection of a treatment for the cancer.

As will be understood by those of ordinary skill in the art, imaging using methods of the invention may include full body imaging of a subject, or imaging of a specific body region or tissue of interest. For example, if a subject is known or suspected of having a solid tumor in the lung, methods of the invention may be used to image the tumor and lung. In some embodiments, imaging may be limited to the CNS and/or to a specific region of the CNS. For example, in a subject with temporal lobe epilepsy, the temporal lobes may be imaged using methods of the invention and for a subject for whom stroke or cerebral infarction is suspected or confirmed, imaging may include imaging of the entire brain.

In some aspects of the invention, imaging methods may include imaging of a specific tissue, region, or structure (e.g., a tumor) and in some aspects may include imaging of perfusion of a body region or structure. For example, methods of the invention may be used to image a tumor or cancer in a subject, and may also be used to image perfusion of the brain, or part of the brain, e.g., one or more brain structures. Perfusion of the brain will be understood by those of ordinary skill in the art to reflect the blood flow through the brain. Perfusion of the brain using methods of the invention may be useful to image regions of damage to the brain or regions of recovery of a previously damaged brain. Non-limiting examples of the use of perfusion methods of the invention include its use to image brain regions with reduced or obstructed blood flow resulting from an occlusion of blood vessels in the brain and also include its use to image brain regions with excessive blood flow, for example, resulting from a hemorrhagic event.

Some aspects of the invention include methods of administering to a subject an amount of a contrast agent effective to image a cancer in the subject. Some aspects of the invention include methods of administering to a subject an amount of a contrast agent effective to image a specific CNS region in the subject. Contrast agents of the invention, when administered to a subject, preferentially localize to mitochondria. The localization of contrast agents to mitochondria permits determination of relative levels of mitochondria in tissues and regions in the subject. An increased amount of contrast agent of the invention localizes to tissues and/or regions with higher levels of mitochondria and/or higher mitochondrial density versus the amount of contrast agent that localizes in tissues or regions having a lower level of mitochondria and/or lower mitochondrial density in the tissue or region. The level or intensity of an imaging signal localized to a tissue or body region of a subject following administration of a contrast agent in a method of the invention, indicates the level of mitochondria and/or mitochondrial density in that tissue or body region. Similarly, a decreased amount of contrast agent of the invention localizes to tissues and/or regions with lower levels of mitochondria or mitochondrial density versus the amount of contrast agent that localizes to tissues or regions having a higher level of mitochondria and/or mitochondrial density. The level or intensity of an imaging signal localized to a tissue or body region of a subject following administration of a contrast agent in a method of the invention, indicates the level of mitochondria and/or mitochondrial density in that tissue or body region. This ability to quantify the uptake of the agent into tissue of interest is inherent in the physics of PET, which allows for relatively precise and accurate calculations of uptake into tissues compared to the injected dose of imaging agent. Comparison of this uptake versus levels that are expected from normal tissues allows for assessment and diagnosis of the subject.

Information on mitochondria levels in tissues or body regions that is obtained using imaging methods of the invention may be used for diagnosis of or to aid in the diagnosis of CNS disorders or conditions. Such information may also be used for diagnosis of or to aid in the diagnosis of cancer in a subject. In disorders characterized by increased levels or density of mitochondria in tissues compared to healthy tissues, an increase in imaging intensity in the tissues when using an imaging method of the invention may indicate the presence of the disorder. Similarly, in disorders characterized by decreased levels or density of mitochondria in tissues compared to healthy tissues, a decrease in imaging intensity in the tissues when using an imaging method of the invention may indicate the presence of the disorder. Those of ordinary skill in the art will recognize that disorders characterized by increased mitochondria density and disorders characterized by decreased mitochondrial density can both be assessed using methods of the invention.

Imaging methods of the invention may be used to assess cancer or a CNS disorder or condition and to select an appropriate treatment for a subject. In addition, imaging methods set forth herein are also useful to monitor changes in a subject with respect to cancer or a CNS disorder or condition over time; for example, to assess the onset, progression, or regression of a cancer or a CNS disorder or condition in a subject over a period of time. The mitochondrial level in a tissue of a subject with a CNS disorder or a cancer may be determined using imaging methods of the invention at one, two, three, four, or more separate times. The level of mitochondria in a specific CNS region or cancer in the subject at the different times may be compared and changes in the mitochondrial levels over time may be used to assess the status and stage of the cancer or CNS disorder or condition in the subject and/or the effect of a treatment strategy on the cancer or CNS disorder or condition in the subject. Imaging methods of the invention can also be used to evaluate a treatment for a cancer or a CNS disorder or condition in a subject. An increase or decrease in the level of mitochondria or mitochondrial density in a tissue resulting from a treatment may be used to evaluate the efficacy of the treatment.

In some aspects of the invention, changes in a cancer or CNS disorder or a condition in a subject resulting from treatment of a CNS disorder or cancer in a subject can be determined using methods of the invention to provide a determination of the efficacy of a treatment or therapeutic protocol in the subject. For example, a level of mitochondria and/or mitochondrial density in a region of the CNS can be obtained using imaging methods of the invention prior to the start of a therapeutic regimen (either prophylactic or as a treatment of the CNS disorder or condition); during the treatment regimen; and/or after a treatment regimen, thus providing information on changes in the status of the CNS disorder or condition over the course of the treatment. Similarly, determinations made using imaging methods of the invention at two or more time points before, during, and/or after treatment for a cancer may be useful to assess the efficacy of the therapeutic regimen for the cancer.

It will be understood that a therapeutic regimen may be either prophylactic or a treatment of a cancer or CNS disorder or condition in a subject. Thus, methods of the invention may be used to monitor a subject's response to prophylactic therapy and/or treatment provided to a patient having or at risk of having a CNS disorder or a cancer.

Methods of the invention may also be used in a variety of assays based upon detecting levels of mitochondria in tissues or regions. Non-limiting examples of assays include (1) evaluating a treatment of a CNS disorder or cancer in a subject; (2) selecting a treatment for a CNS disorder or a cancer based at least in part on the imaging of mitochondrial levels in a tissue or body region of the subject; and (3) determining the status of a CNS disorder or cancer in the subject. Thus, subjects can be characterized, treatment regimens can be monitored, treatments can be selected and diseases status can be better understood using methods of the present invention.

Methods described herein include the use of contrast agents of the invention and may involve determining levels of mitochondria or mitochondrial density in tissues and/or regions of a subject. Levels of mitochondria and mitochondrial density in a tissue or region in a subject can be determined in a number of ways when carrying out the various methods of the invention. In one particularly important measurement, a level of mitochondria and/or mitochondrial density is measured in relation to a control level of mitochondria and/or mitochondrial density in a tissue or region of a subject. One possible measurement of the level of mitochondria and/or mitochondrial density is a measurement of absolute levels of mitochondria and/or mitochondrial density. This could be expressed, for example, in mitochondria and/or mitochondrial density unit of cells or tissue. Another measurement of the level of mitochondria and/or mitochondrial density is a measurement of the change in the level of mitochondria and/or mitochondrial density over time. This may be expressed in an absolute amount or may be expressed in terms of a percentage increase or decrease over time.

Controls

Importantly, levels of mitochondria and/or mitochondrial density can be determined using imaging methods of the invention and are advantageously compared to controls according to the invention. A control may be a predetermined value, which can take a variety of forms. It can be a single cut-off value, such as a median or mean. It can be established based upon comparative groups, such as in groups having normal levels of mitochondria and/or mitochondrial density and groups having abnormal levels of mitochondria and/or mitochondrial density. Another example of comparative groups may be groups having cancer or cancer symptoms and groups without cancer or cancer symptoms or groups having symptoms of a CNS disorder or condition and groups not having symptoms of a CNS disorder or condition. Another comparative group may be a group with a family history of cancer or a CNS disorder or condition and a group without such a family history. A predetermined value can be arranged, for example, where a tested population is divided equally (or unequally) into groups, such as a low-risk group, a medium-risk group and a high-risk group or into quadrants or quintiles, the lowest quadrant or quintile being individuals with the lowest risk (e.g. of cancer or of a CNS disorder or condition) and lowest levels of mitochondria and/or mitochondrial density and the highest quadrant or quintile being individuals with the highest risk (e.g. of cancer or of a CNS disorder or condition) and highest levels of mitochondria and/or mitochondrial density. It will be understood by those of ordinary skill in the art that some CNS disorders or conditions are associated with a higher level of mitochondria and/or mitochondrial density and other CNS disorders or conditions are associated with a lower level of mitochondria and/or mitochondrial density. One of ordinary skill in the art will be able to assign the population and risk groupings based on the specific CNS disorder or condition of interest.

The predetermined value, of course, will depend upon the particular population selected. For example, an apparently healthy population will have a different 'normal' range than will a population that is known to have a condition related to abnormal mitochondria and/or mitochondrial density. Accordingly, the predetermined value selected may take into account the category in which an individual or tissue falls. Appropriate ranges and categories can be selected with no more than routine experimentation by those of ordinary skill in the art. As used herein, "abnormal" means not normal as compared to a control. By abnormally high it is meant high relative to a selected control. By abnormally low it is meant low relative to a selected control. Typically a control will be based on apparently healthy tissue or individuals in an appropriate age bracket or apparently healthy tissues. It will be understood that controls according to the invention may be, in addition to predetermined values, subjects imaged under the substantially similar conditions with the test subject. In some aspects of the invention, a control image for a subject may be a prior image from the same subject.

As mentioned above, it is also possible to use the imaging methods of the invention to characterize mitochondria and/or mitochondrial density levels by monitoring changes in the amount of mitochondria and/or mitochondrial density over time. For example, it is expected that in some disorders or conditions a decrease in mitochondria and/or mitochondrial density correlates with improvement of the disorder or condition and in other disorders or conditions an increase in mitochondria and/or mitochondrial density correlates with improvement of the disorder or condition. Accordingly one can monitor levels of mitochondria and/or mitochondrial density over time to determine if there is a change in the subject's disorder or condition status. Changes in levels of mitochondria and/or mitochondrial density greater than 0.1% may indicate an abnormality. Preferably, the change (in some disorders an increase and in other disorders a decrease) in mitochondria and/or mitochondrial density, which indicates an abnormality, is a change greater than 0.2%, greater than 0.5%, greater than 1.0%, 2.0%, 3.0%, 4.0%, 5.0%, 7.0%, 10%, 15%, 20%, 25%, 30%, 40%, 50%, or more. Changes in the amount of mitochondria and/or mitochondrial density over time may indicate a change in the status of the disorder or condition in the subject.

Imaging methods of the invention may also be used in diagnostic methods to determine the effectiveness of treatments for cancer or a CNS disorder or condition. "Evaluation of treatment" as used herein, means the comparison of a subject's levels of mitochondria and/or mitochondrial density measured in a subject at different imaging times, preferably at least one day apart. In some embodiments, the time at which the subject is administered a contrast agent and imaged using a method of the invention and is at least 1, 2, 3, 4, 5, 6, 7, 8, 9, 10, 11, 12, 13, 14, 15, 16, 17, 18, 19, 20, 21, 22, 23, 24, 36, 48, 72, 96, 120, or more hours (including all times between) after obtaining the first sample from the subject. In some embodiments, the time at which the subject is administered a contrast agent and imaged using a method of the invention is at least 5, 10, 15, 20, 30, 50, 80, 100, 200, 500, 1000, or more days after the previous image (including all times between).

Imaging methods of the invention may be used to allow the comparison of levels of mitochondria and/or mitochondrial density in two or more samples, taken at different times, which may be used to detect the status of a cancer or a CNS disorder or condition in a subject and allows evaluation of a cancer treatment or treatment of the CNS disorder or condition. The comparison of a subject's levels of mitochondria and/or mitochondrial density determined using methods of the invention at different times and/or on different days provides a measure of the status of the cancer or CNS disorder or condition that can be used to determine the effectiveness of any treatment of the cancer or CNS disorder or condition in a subject.

Kits

In some aspects of the invention, kits are provided. Kits containing contrast and imaging agents of the invention can be prepared for in vivo diagnosis, prognosis and/or monitoring the level of mitochondria and/or mitochondrial density in tissues, and/or subjects using methods described herein. Components of the kits can be packaged as pure solid or liquids, in aqueous medium, in organic solutions or in lyophilized form. When the contrast agent of the invention are used in the kits in the form of conjugates in which an imaging moiety is attached, such as a radioactive element, the components of such conjugates can be supplied either in fully conjugated form, in the form of intermediates or as separate moieties to be conjugated by the user or the kit.

A kit may comprise a carrier being compartmentalized to receive in close confinement therein one or more container means or series of container means such as test tubes, vials, flasks, bottles, syringes, or the like. A first of said container means or series of container means may contain a contrast agent precursor. A second container may contain adjuvents for facilitating the conversion of the contrast agent precursor to the contrast agent and its subsequent manipulation into a suitable dosage form.

A kit of the invention may also include instructions. Instructions typically will be in written form and will provide guidance for carrying-out the synthesis of the imaging agent by the kit and for formulating a suitable dose from the results of said synthesis.

Definitions

For convenience, certain terms employed in the specification, examples, and appended claims are listed here.

The number of carbon atoms in any particular group is denoted before the recitation of the group. For example, the term "$C_6$-$C_{10}$aryl" denotes an aryl group containing from six to ten carbon atoms, and the term "$C_6$-$C_{10}$aryl-$C_1$-$C_{10}$alkyl," refers to an aryl group of six to ten carbon atoms attached to the parent molecular moiety through an alkyl group of one to ten carbon atoms.

The term "alkenyl," as used herein, refers to a straight or branched chain hydrocarbon containing at least one carbon-carbon double bond.

The term "alkoxy," as used herein, refers to a $C_1$-$C_6$ alkyl group attached to the parent molecular moiety through an oxygen atom.

The term "alkoxyalkyl," as used herein, refers to a $C_1$-$C_6$ alkyl group substituted with one, two, or three alkoxy groups.

The term "alkyl," as used herein, refers to a group derived from a straight or branched chain saturated hydrocarbon.

The term "alkylaryl," as used herein, refers to an alkyl group attached to the parent molecular moiety through an aryl group.

The term "alkylene," as used herein, refers to a divalent group derived from a straight or branched chain saturated hydrocarbon.

The term "alkyloxy," as used herein, refers to a $C_1$-$C_6$ alkyl group attached to the parent molecular moiety through an oxygen atom.

The term "analog moiety," as used herein, refers to the compounds of the present invention excluding the imaging moiety or moieties.

The term "aryl," as used herein, refers to a phenyl group, or a bicyclic fused ring system wherein one or more of the rings is a phenyl group. Bicyclic fused ring systems consist of a phenyl group fused to a monocyclic cycloalkenyl group, a monocyclic cycloalkyl group, or another phenyl group. The aryl groups of the present invention can be attached to the parent molecular moiety through any substitutable carbon atom in the group. Representative examples of aryl groups include, but are not limited to, anthracenyl, azulenyl, fluorenyl, indanyl, indenyl, naphthyl, phenyl, and tetrahydronaphthyl.

The term "arylalkyl," as used herein, refers to an alkyl group substituted with one, two, or three aryl groups.

The term "arylalkylene," as used herein, refers to a divalent arylalkyl group, where one point of attachment to the parent molecular moiety is on the aryl portion and the other is on the alkyl portion.

The term "arylene," as used herein, refers to a divalent aryl group.

A "bacteriostat" is a component that inhibits the growth of bacteria in a formulation either during its storage before use of after a diagnostic kit is used to synthesize a radiopharmaceutical.

The terms "brain" and "central nervous system" as used herein are intended to be interchangeable and are not to be construed as mutually exclusive.

The term "cancer" as used herein refers to neoplasia, oncologic growths, malignant tumors, benign tumors, metastases, or undifferentiated cellular growths.

The term "contrast agent," as used herein, refers to an agent used to highlight specific areas so that organs, blood vessels, and/or tissues are more visible using methods such as . By increasing the visibility of the surfaces being studied, the presence and extent of disease and/or injury can be determined.

The term "cycloalkenyl," as used herein, refers to a non-aromatic, partially unsaturated monocyclic, bicyclic, or tricyclic ring system having three to fourteen carbon atoms and zero heteroatoms. Representative examples of cycloalkenyl groups include, but are not limited to, cyclohexenyl, octahydronaphthalenyl, and norbornylenyl.

The term "cycloalkyl," as used herein, refers to a saturated monocyclic, bicyclic, or tricyclic hydrocarbon ring system having three to fourteen carbon atoms and zero heteroatoms. Representative examples of cycloalkyl groups include, but are not limited to, cyclopropyl, cyclopentyl, bicyclo[3.1.1]heptyl, and adamantyl.

The term "$C_3$-$C_{10}$ cycloalkylene," as used herein, refers to a divalent cycloalkyl group containing from three to ten carbon atoms.

The term "determining" or "determination," as used herein, generally refers to the analysis of a species or signal (e.g., image), for example, quantitatively or qualitatively, and/or the detection of the presence or absence of the species or signals. "Determining" may also refer to the analysis of an interaction between two or more species or signals, for example, quantitatively or qualitatively, and/or by detecting the presence or absence of the interaction.

The term "diagnostic imaging," as used herein, refers to a procedure used to detect a contrast agent.

A "diagnostic kit" or "kit" comprises a collection of components, termed the formulation, in one or more vials which are used by the practicing end user in a clinical or pharmacy setting to synthesize diagnostic radiopharmaceuticals. In some embodiments, the kit may provide all the requisite components to synthesize and use the diagnostic pharmaceutical except those that are commonly available to the practicing end user, such as water or saline for injection, a solution of the radionuclide, equipment for processing the kit during the synthesis and manipulation of the radiopharmaceutical, if required, equipment necessary for administering the radiopharmaceutical to the subject such as syringes, shielding, imaging equipment, and the like. In some embodiments, contrast agents may be provided to the end user in their final form in a formulation contained typically in one vial or syringe, as either a lyophilized solid or an aqueous solution.

The terms "halo" and "halogen," as used herein, refer to F, Cl, Br, or I.

The term "haloalkyl," as used herein, refers to a $C_1$-$C_6$ alkyl group substituted by one, two, three, or four halogen atoms.

The term "heteroaryl," as used herein, refers to an aromatic five- or six-membered ring where at least one atom is selected from N, O, and S, and the remaining atoms are carbon. The term "heteroaryl" also includes bicyclic systems where a heteroaryl ring is fused to a four- to six-membered aromatic or non-aromatic ring containing zero, one, or two additional heteroatoms selected from N, O, and S. The heteroaryl groups are attached to the parent molecular moiety through any substitutable carbon or nitrogen atom in the group. Representative examples of heteroaryl groups include, but are not limited to, benzoxadiazolyl, benzoxazolyl, benzofuranyl, benzothienyl, furanyl, imidazolyl, indazolyl, indolyl, isoxazolyl, isoquinolinyl, isothiazolyl, naphthyridinyl, oxadiazolyl, oxazolyl, pyridinyl, pyridazinyl, pyrimidinyl, pyrazinyl, pyrazolyl, pyrrolyl, quinolinyl, thiazolyl, thienopyridinyl, thienyl, triazolyl, thiadiazolyl, and triazinyl.

The term "heterocyclyl," as used herein, refers to a five-, six-, or seven-membered ring containing one, two, or three heteroatoms independently selected from the group consisting of nitrogen, oxygen, and sulfur. The five-membered ring has zero to two double bonds and the six- and seven-membered rings have zero to three double bonds. The term "heterocyclyl" also includes bicyclic groups in which the heterocyclyl ring is fused to a phenyl group, a monocyclic cycloalkenyl group, a monocyclic cycloalkyl group, or another monocyclic heterocyclyl group. The heterocyclyl groups of the present invention can be attached to the parent molecular moiety through a carbon atom or a nitrogen atom in the group. Examples of heterocyclyl groups include, but are not limited to, benzothienyl, furyl, imidazolyl, indolinyl, indolyl, isothiazolyl, isoxazolyl, morpholinyl, oxazolyl, piperazinyl, piperidinyl, pyrazolyl, pyridinyl, pyrrolidinyl, pyrrolopyridinyl, pyrrolyl, thiazolyl, thienyl, and thiomorpholinyl.

The term "heterocyclylalkyl," as used herein, refers to an alkyl group substituted with one, two, or three heterocyclyl groups.

The term "heterocyclylalkylene," as used herein, refers to a divalent heterocyclylalkyl group, where one point of attachment to the parent molecular moiety is on the heterocyclyl portion and the other is on the alkyl portion.

The term "heterocyclylene," as used herein, refers to a divalent heterocyclyl group.

The term "hydroxy," as used herein, refers to —OH.

The term "imaging moiety," as used herein, refer to a portion or portions of a molecule that allow for the detection, imaging, and/or monitoring of the presence and/or progression of a condition(s), pathological disorder(s), and/or disease(s).

The term "linking group," as used herein, refers to a portion of a molecule that serves as a spacer between two other portions of the molecule. Linking groups may also serve other functions as described herein. Examples of linking groups include linear, branched, or cyclic alkyl, aryl, ether, polyhydroxy, polyether, polyamine, heterocyclic, aromatic, hydrazide, peptide, peptoid, or other physiologically compatible covalent linkages or combinations thereof.

A "lyophilization aid" is a component that has favorable physical properties for lyophilization, such as the glass transition temperature, and is generally added to the formulation to improve the physical properties of the combination of all the components of the formulation for lyophilization.

The term "oxo," as used herein, refers to =O.

Any of the contrast agents described herein may be optionally substituted with one or more of the following: alkyl, alkenyl, cycloalkyl, alkylaryl, alkylcarbonyl, aryl, arylalkyl, alkylarylalkyl, alkoxy, alkoxyalkyl, alkoxycarbonyl, heteroalkyl, heterocyclyl, heterocyclylalkyl, amino, thiol, —OH, phosphate, —CO$_2$H, =O, halo, trifluoromethyl, nitro, cyano, ester, aldehyde, amide, keto, azide, sulfhydryl, imino, phosphonate, phosphinate, carbonyl, carboxyl, silyl, ether, alkylthio, sulfonyl, or sulfonamido, each of which may be optionally substituted. In some embodiments, the contrast agent may be substituted with an imaging agent.

The term "pyridaben" is given its ordinary meaning in the art and refers to a compound having the structure,

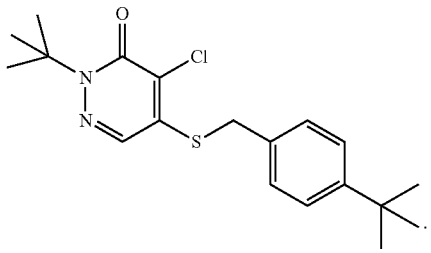 [SMILES: CC(C)(C)c1ccc(CSc2cnn(C(C)(C)C)c(=O)c2Cl)cc1]

The term "pyridaben analog" refers to analogs of pyridaben, including, but not limited to, the contrast agents of Formula (II), as described herein.

The term "fenazaquin" is given its ordinary meaning in the art and refers to a compound having the structure,

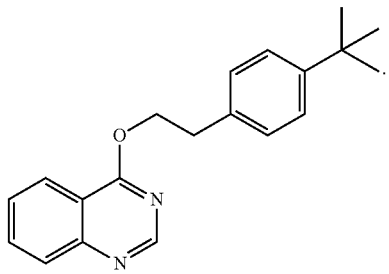 [SMILES: CC(C)(C)c1ccc(CCOc2ncnc3ccccc23)cc1]

The term "fenazaquin analog" refers to analogs of fenazaquin, including, but not limited to, the contrast agents of Formula (III), as described herein.

As used herein, the phrase "pharmaceutically acceptable" refers to those compounds, materials, compositions, and/or dosage forms that are, within the scope of sound medical judgment, suitable for use in contact with the tissues of human beings and animals without excessive toxicity, irritation, allergic response, or other problem or complication, commensurate with a reasonable benefit/risk ratio.

The term "pharmaceutically acceptable salt," as used herein, represents salts or zwitterionic forms of the compounds of the present invention which are water or oil-soluble or dispersible, which are, within the scope of sound medical judgment, suitable for use in contact with the tissues of subjects without excessive toxicity, irritation, allergic response, or other problem or complication commensurate with a reasonable benefit/risk ratio, and are effective for their intended use The salts can be prepared during the final isolation and purification of the compounds or separately by reacting a suitable nitrogen atom with a suitable acid. Representative acid addition salts include acetate, adipate, alginate, citrate, aspartate, benzoate, benzenesulfonate, bisulfate, butyrate, camphorate, camphorsulfonate; digluconate, glycerophosphate, hemisulfate, heptanoate, hexanoate, formate, fumarate, hydrochloride, hydrobromide, hydroiodide, 2-hydroxyethanesulfonate, lactate, maleate, mesitylenesulfonate, methanesulfonate, naphthylenesulfonate, nicotinate, 2-naphthalenesulfonate, oxalate, palmoate, pectinate, persulfate, 3-phenylpropionate, picrate, pivalate, propionate, succinate, tartrate, trichloroacetate, trifluoroacetate, phosphate, glutamate, bicarbonate, para-toluenesulfonate, and undecanoate. Examples of acids which can be employed to form pharmaceutically acceptable addition salts include inorganic acids such as hydrochloric, hydrobromic, sulfuric, and phosphoric, and organic acids such as oxalic, maleic, succinic, and citric.

As used herein, a "portion of a brain" refers to a particular region of the brain, location in the brain, or structure of the brain.

As used herein, a "portion of the CNS" refers to a particular region of the CNS, location in the CNS, or structure of the CNS.

As used herein, a "portion of a subject" refers to a particular region of a subject, location in the subject, or structure of the subject. For example, a portion of a subject may be the brain of a subject.

The phrase "protecting group" as used herein refers to temporary substituents which protect a potentially reactive functional group from undesired chemical transformations. Examples of such protecting groups include esters of carboxylic acids, silyl ethers of alcohols, and acetals and ketals of aldehydes and ketones, respectively. The field of protecting group chemistry has been reviewed (Greene, T. W.; Wuts, P. G. M. *Protective Groups in Organic Synthesis*, 2$^{nd}$ ed.; Wiley: New York, 1991).

By "reagent" is meant a compound of this disclosure capable of direct transformation into a metallopharmaceutical of this disclosure. Reagents may be utilized directly for the preparation of the metallopharmaceuticals of this disclosure or may be a component in a kit of this disclosure.

As used herein, the term "react" or "reacting" refers to the formation of a bond between two or more components to produce a stable, isolable compound. For example, a first component and a second component may react to form one reaction product (e.g., contrast agent) comprising substantial portions of or the entirety of the first component and the second component joined by a covalent bond. That is, the term "reacting" does not refer to the interaction of solvents, catalysts, bases, ligands, or other materials which may serve to promote the occurrence of the reaction with the component(s).

A "stable, isolable compound" refers to isolated reaction products and does not refer to unstable intermediates or transition states.

A "stabilization aid" is a component that is typically added to the metallopharmaceutical or to the diagnostic kit either to stabilize the metallopharmaceutical or to prolong the shelf-life of the kit before it must be used. Stabilization aids can be antioxidants, reducing agents or radical scavengers and can provide improved stability by reacting preferentially with species that degrade other components or the metallopharmaceuticals.

By "stable compound" or "stable structure" is meant herein a compound that is sufficiently robust to survive isolation to a useful degree of purity from a reaction mixture, and formulation into an efficacious pharmaceutical agent.

A "solubilization aid" is a component that improves the solubility of one or more other components in the medium required for the formulation.

The term "thiol protecting group," as used herein, refers to a group intended to protect a thiol group against undesirable reactions during synthetic procedures. Any thiol protecting group known in the art may be used. Examples of thiol protecting groups include, but are not limited to, the following: acetamidomethyl, benzamidomethyl, 1-ethoxyethyl, benzoyl, and triphenylmethyl.

As used herein, the term "subject" refers to a human or non-human mammal or animal. Non-human mammals include livestock animals, companion animals, laboratory animals, and non-human primates. Non-human subjects also specifically include, without limitation, horses, cows, pigs, goats, dogs, cats, mice, rats, guinea pigs, gerbils, hamsters, mink, and rabbits. As used herein, the term "patient" refers to a subject who is under the care of a physician or other health care worker, including, but not limited to, someone who has consulted with, received advice from or received a prescription or other recommendation from a physician or other health care worker. A patient is typically a subject having or at risk of having cancer or a CNS disorder or condition.

Some subjects to which the present invention can be applied are subjects with CNS disorders or conditions or subjects with cancer. The terms "subject with cancer" or "subject with a CNS disorder or condition" as used herein, means an individual who, at the time the imaging, has been diagnosed as having cancer or a CNS disorder or condition respectively. Methods of the invention may also be used to detect abnormal levels or density of mitochondria in tissues or regions in subjects that are not yet diagnosed with cancer or a CNS disorder or condition and thus are useful for initial or confirmatory diagnosis of cancer or of a CNS disorder or condition in a subject.

As used herein, the term "CNS disorder or condition" includes, but is not limited to, epilepsy, aging, stress disorder, schizophrenia, Huntington's disease, Alzheimer's disease, Parkinson's disease, cerebral hypoxia, cerebral infarction and/or neural cell injury associated with a stroke, Guillian Bane, arachnoiditis, brain abscess, CNS infection, cerebral palsy, corticobasal ganglionic degeneration (CBGD), Creutzfeldt-Jakob syndrome, Dandy-Walker syndrome, dementia, encephalitis, Herpes Simplex, encephalomyelitis, essential tremor, Friedreich Ataxia, Gerstmann-Straussler-Scheinker disease, hydrocephalus, Fatal Familial Insomnia, Kuru, Landau-Kleffner Syndrome, Lewy Body disease, Machado-Joseph disease, Meige Syndrome, meningitis (viral or bacterial), migraine disorders, movement disorders, Multiple System Atrophy, myelitis, Olivopontocerebellar atrophies, pantothenate kinase-associated neurodegeneration, poliomyelitis, postpoliomyelitis syndrome, prion diseases, pseudotumor cerebri, Shy-Drager syndrome, spinal cord diseases, Supranuclear Palsy, Syringomyelia, thalamic diseases, tic disorders, Tourette syndrome, Uveomeningoencephalitic syndrome.

Examples of categories of CNS disorders or conditions include, but are not limited to lesions of either the central (including spinal cord, brain) or peripheral nervous systems such as: (1) ischemic lesions, in which a lack of oxygen in a portion of the nervous system results in neuronal injury or death, including cerebral infarction or ischemia, or spinal cord infarction or ischemia; (2) traumatic lesions, including lesions caused by physical injury or associated with surgery, for example, lesions which sever a portion of the nervous system, or compression injuries; (3) malignant lesions, in which a portion of the nervous system is destroyed or injured by malignant tissue which is either a nervous system associated malignancy or a malignancy derived from non-nervous system tissue; (4) infectious lesions, in which a portion of the nervous system is destroyed or injured as a result of infection, for example, by an abscess or associated with infection by human immunodeficiency virus, herpes zoster, or herpes simplex virus or with Lyme disease, tuberculosis, syphilis; (5) degenerative lesions, in which a portion of the nervous system is destroyed or injured as a result of a degenerative process including but not limited to degeneration associated with Parkinson's disease, Alzheimer's disease, Huntington's chorea, or amyotrophic lateral sclerosis (ALS); (6) lesions associated with nutritional diseases, disorders, and/or conditions, in which a portion of the nervous system is destroyed or injured by a nutritional disorder or disorder of metabolism including but not limited to, vitamin B12 deficiency, folic acid deficiency, Wernicke disease, tobacco-alcohol amblyopia, Marchiafava-Bignami disease (primary degeneration of the corpus callosum), and alcoholic cerebellar degeneration; (7) neurological lesions associated with systemic diseases including, but not limited to, diabetes (diabetic neuropathy, Bell's palsy), systemic lupus erythematosus, carcinoma, or sarcoidosis; (8) lesions caused by toxic substances including alcohol, lead, or particular neurotoxins; and (9) demyelinated lesions in which a portion of the nervous system is destroyed or injured by a demyelinating disease including, but not limited to, multiple sclerosis, human immunodeficiency virus-associated myelopathy, transverse myelopathy or various etiologies, progressive multifocal leukoencephalopathy, and central pontine myelinolysis.

As used herein, the term "cancer" refers to an uncontrolled growth of cells that may interfere with the normal functioning of the bodily organs and systems, and includes both primary and metastatic tumors. Primary tumors or cancers that migrate from their original location and seed vital organs can eventually lead to the death of the subject through the functional deterioration of the affected organs. A metastasis is a cancer cell or group of cancer cells, distinct from the primary tumor location, resulting from the dissemination of cancer cells from the primary tumor to other parts of the body. Metastases may eventually result in death of a subject. Imaging methods of the invention may also be used to assess the status of precancerous conditions, (e.g., conditions if left untreated are likely to lead to cancer in a subject)

As used herein, the term "cancer" includes, but is not limited to, the following types of cancer: breast cancer (including carcinoma in situ), biliary tract cancer; bladder cancer; brain cancer including glioblastomas and medulloblastomas; cervical cancer; choriocarcinoma; colon cancer; endometrial cancer; esophageal cancer; gastric cancer; hematological neoplasms including acute lymphocytic and myelogenous leukemia; T-cell acute lymphoblastic leukemia/lymphoma; hairy cell leukemia; chromic myelogenous leukemia, multiple myeloma; AIDS-associated leukemias and adult T-cell leukemia lymphoma; intraepithelial neoplasms including Bowen's disease and Paget's disease; liver cancer; lung cancer; lymphomas including Hodgkin's disease and lymphocytic lymphomas; mesothelioma, neuroblastomas; oral cancer including squamous cell carcinoma; ovarian cancer including those arising from epithelial cells, stromal cells, germ cells and mesenchymal cells; pancreatic cancer; prostate cancer; rectal cancer; sarcomas including leiomyosarcoma, rhabdomyosarcoma, liposarcoma, fibrosarcoma, and osteosarcoma; skin cancer including melanoma, Merkel cell carcinoma, Kaposi's sarcoma, basal cell carcinoma, and squamous cell cancer; cancers of the head and neck, testicular cancer including germinal tumors such as seminoma, non-seminoma (teratomas, choriocarcinomas), stromal tumors, and germ cell tumors; thyroid cancer including thyroid adenocarcinoma and medullar carcinoma; and renal cancer including adenocarcinoma and Wilms tumor. Non-limiting examples of precancerous conditions include dysplasia, premalignant lesions, adenomatous colon polyp, and carcinoma in-situ such as Ductal carcinoma in-situ (DCIS), etc. Other cancers that can be imaged with methods of the invention will be known to those of ordinary skill in the art.

EXAMPLES

The present invention will now be described in connection with certain embodiments which are not intended to limit its scope. On the contrary, the present invention covers all alternatives, modifications, and equivalents as can be included within the scope of the claims. Thus, the following examples will illustrate one practice of the present invention, it being understood that the examples are for the purposes of illustration of certain embodiments and are presented to provide what is believed to be the most useful and readily understood description of its procedures and conceptual aspects.

Example 1

Synthesis of Fenazaquin Analog

Example 1A

Synthesis of 4-[4-(2-Hydroxyethyl)phenyl]-4-oxobutyric acid methyl ester

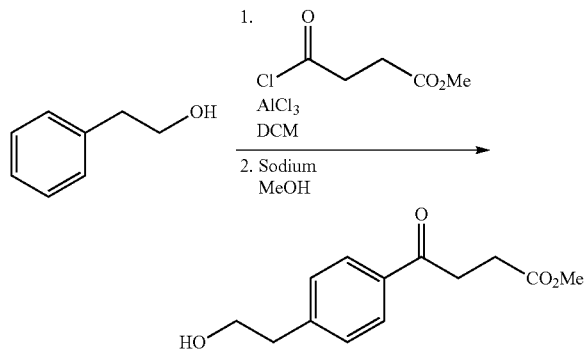

To a dry 250 mL flask under a nitrogen atmosphere was added phenethyl alcohol (2.50 g, 0.02 mol), anhydrous dichloromethane (150 mL), and methyl-4-chloro-4-oxobutyrate (6.02 g, 0.04 mol). The contents of the flask were cooled to 0° C. with an ice bath. To the solution was added aluminum chloride (25 g, 0.2 mol) in portions being careful to avoid a violent exotherm. The resulting yellowish mixture was stirred for 3 hours. At this point the reaction was quenched with ice water. The mixture was diluted with dichloromethane and transferred to a separatory funnel. The organic layer was washed with a saturated solution of sodium bicarbonate, brine and then dried over magnesium sulfate. Filtration and concentration of the filtrate under reduced pressure provided a crude yellow oil. The oil was suspended in anhydrous methanol (100 mL) and sodium metal was added to the mixture until a pH of 9 was obtained. The mixture was stirred for 3 hours. The volume was reduced and then diluted with ethyl acetate. The solution was transferred to a separatory funnel and washed with aqueous 0.05 N hydrochloric acid, brine and dried over magnesium sulfate. The solution was concentrated under reduced pressure to give a crude yellow oil with a mass of 5.88 g. Column chromatography [silica gel; eluent hexanes-ethyl acetate (3:2)] provided the desired product (2.69 g, 57%). $^1$H (CDCl$_3$) δ (ppm): 2.65 (t, 2H); 2.81 (t, 2H); 3.19 (t, 2H); 3.6 (s, 3H); 3.75 (t, 2H); 7.22 (d, 2H); 7.81 (d, 2H). $^{13}$C (CDCl$_3$) δ (ppm): 27.76, 33.03, 38.66, 51.52, 62.68, 127.97, 128.99, 134.47, 144.78, 173.21,197.64.

Example 1B

Synthesis of 4-[4-(2-hydroxyethyl)phenyl]butyric acid methyl ester

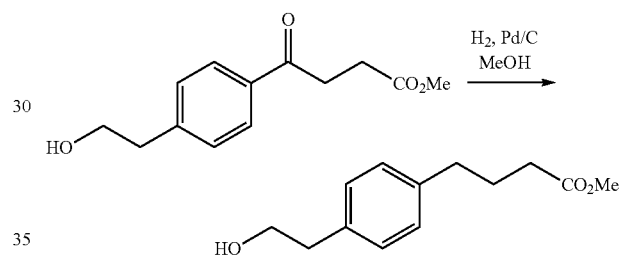

A mixture of Example 1A (2.50 g, 11 mmol), 10% Pd/C (0.25 g, 0.23 mmol of Pd metal) in anhydrous methanol (25 mL) was first degassed to remove air (two vacuum/H$_2$ cycles) after which it was capped and a balloon filled with H$_2$ was applied to it for 12 hours. After this time the reaction mixture was filtered through diatomaceous earth (Celite®) and the filtrate was concentrated under reduced pressure to give 2.32 g of crude material. Column chromatography [silica gel; eluent hexanes-ethyl acetate (2:1)] provided the desired product (0.92 g, 39%). $^1$H (CDCl$_3$) δ (ppm): 1.91-1.96 (m, 2H); 2.32 (t, 2H); 2.62 (t, 2H); 2.83 (t, 2H); 3.66 (s, 3H); 3.85 (t, 2H); 7.11-7.15 (m, 4H).

Example 1C

Synthesis of 4-{4-[2-(quinazolin-4-yloxy)ethyl]phenyl}butyric acid methyl ester

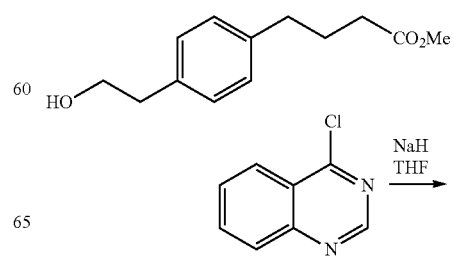

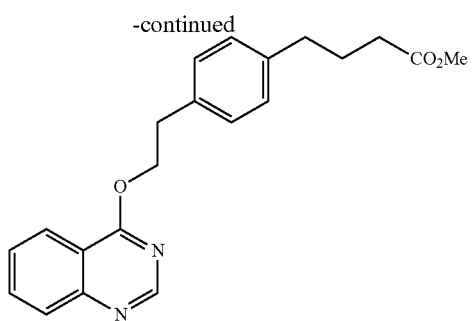

A dry 50 mL flask was fitted with an addition funnel. To the flask were added 4-chloroquinazoline (592 mg, 3.6 mmol), anhydrous tetrahydrofuran (10 mL), and 60 wt % sodium hydride (187 mg, 4.7 mmol). A solution of Example 1B (800 mg, 3.6 mmol) in anhydrous tetrahydrofuran (10 mL) was added dropwise using the addition funnel. The reaction was stirred for 3.5 hours. The reaction was diluted with ethyl acetate and quenched by the addition of aqueous 0.1 N hydrochloric acid. The mixture was transferred to a separatory funnel and washed with brine. The organic layer was dried over magnesium sulfate, filtered, and concentrated. Column chromatography [silica gel; eluent hexanes-ethyl acetate (4:1)] provided the desired product (538 mg, 43%). $^1$H(CDCl$_3$) δ (ppm): 1.92-1.98 (m, 2H); 2.33 (t, 2H); 2.64 (t, 2H); 3.19 (t, 2H); 3.66 (s, 3H); 4.79 (t, 2H); 7.15 (d, 2H); 7.27 (d, 2H); 7.57 (t, 1H); 7.83 (t, 1H); 7.94 (d, 1H); 8.15 (d, 1H); 8.80 (s, 1H). 26.68, 33.59, 34.93, 35.03, 51.67, 67.89, 116.48, 123.72, 127.23, 127.82, 128.87, 129.24, 133.74, 135.76, 139.90, 151.08, 154.56, 166.89, 174.10.

Example 1D

Synthesis of 4-{4-[2-(Quinazolin-4-yloxy)ethyl]phenyl}butan-1-ol

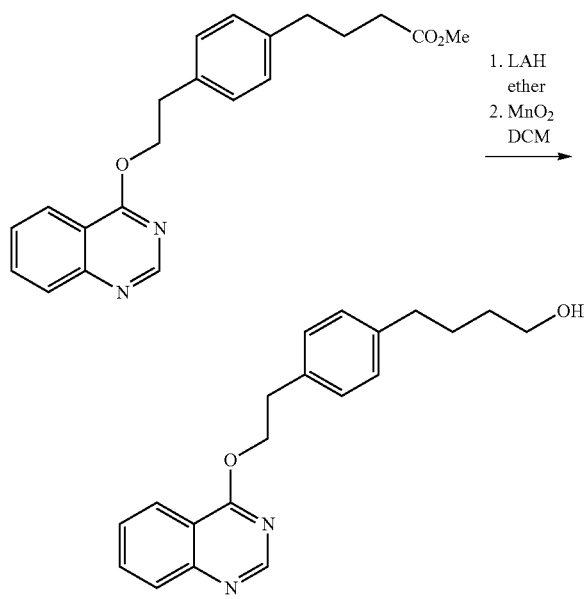

To a dry 15 mL flask was added lithium aluminum hydride (233 mg, 6.0 mmol) and anhydrous diethyl ether (3 mL). The mixture was cooled with an ice bath. A solution of Example 1C (538 mg, 1.54 mmol) in anhydrous diethyl ether (3 mL) was slowly added with vigorous stirring. The bath was removed and the slurry was stirred for 15 minutes. The reaction was quenched with water (0.233 mL), aqueous 15% sodium hydroxide (0.233 mL) and water (0.699 mL). The white solid was filtered and the filtrate was dried over magnesium sulfate, filtered, and concentrated under reduced pressure to give a clear oil. The oil was then dissolved in anhydrous dichloromethane (10 mL) and manganese(IV) oxide (500 mg, 5.8 mmol) was added to the solution. The mixture was stirred for 12 hours. Filtration through diatomaceous earth (Celite®) followed by concentration of the filtrate under reduced pressure afforded 395 mg of crude product. Column chromatography [silica gel; eluent pentane-ethyl acetate (2:3)] provided the desired product (225 mg, 49%). $^1$H (CDCl$_3$) δ (ppm): 1.55-1.61 (m, 2H); 1.65-1.68 (m, 2H); 2.61 (t, 2H); 3.17 (t, 2H); 3.64 (t, 2H); 4.79 (t, 2H); 7.12 (d, 2H); 7.23 (d, 2H); 7.56 (t, 1H); 7.82 (t, 1H); 7.93 (d, 1H); 8.14 (d, 1H); 8.77 (s, 1H). $^{13}$C (CDCl$_3$) δ (ppm): 27.52, 32.31, 34.89, 35.21, 62.81, 67.74, 116.67, 123.54, 127.08, 127.49, 128.63, 128.98, 133.61, 135.23, 140.64, 150.68, 154.29, 166.79.

Example 1E

Synthesis of Toluene-4-sulfonic acid 4-{4-[2-(quinazolin-4-yloxyethyl]phenyl}butyl ester

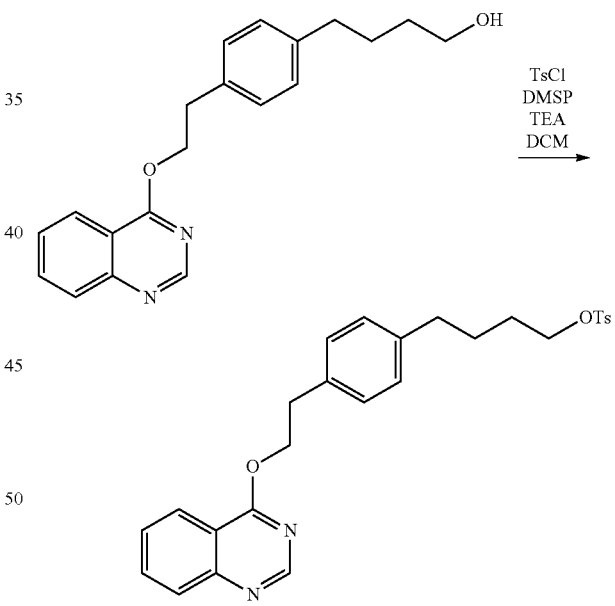

To a dry 10 mL flask was added p-toluenesulfonyl chloride (32.5 mg, 0.17 mmol), 4-(dimethylamino)pyridine (20.7 mg, 0.17 mmol), Example 1D (50.0 mg, 0.16 mmol), anhydrous dichloromethane (1 mL) and triethylamine (17.2 mg, 0.17 mmol). The resulting solution was stirred for 2 hours, concentrated under reduced pressure, and purified by column chromatography [silica gel; eluent pentane-ethyl acetate (1.86:1)] to provide the desired product (52 mg, 70%). $^1$H(CDCl$_3$) δ (ppm): 1.64-1.68 (m, 4H); 2.44 (s, 3H); 2.56 (t, 2H); 3.19 (t, 2H); 4.04 (t, 2H); 4.78 (t, 2H); 7.08 (d, 2H); 7.26 (d, 2H); 7.57 (t, 1H); 7.78 (d, 2H); 7.84 (t, 1H), 8.14 (d, 1H); 8.80 (s, 1H).

Example 1F

Synthesis of 4-{2-[4-(4-Fluorobutyl)phenyl]ethoxy}quinazoline

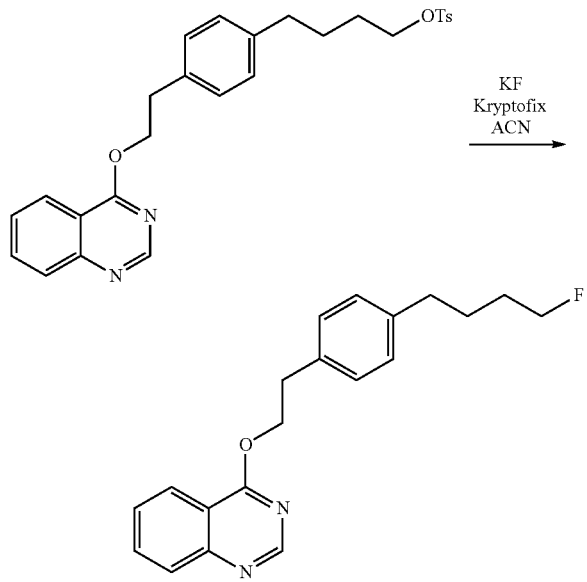

A dry 5 mL flask was fitted with a reflux condenser. To the flask was added potassium fluoride (6.1 mg, 0.1 mmol), kryptofix (40 mg, 0.1 mmol) and anhydrous acetonitrile (0.5 mL). To the resulting solution was added a solution of Example 1E (25 mg, 0.05 mmol) in anhydrous acetonitrile (1 mL). The flask was placed in a 90° C. oil bath. The solution was stirred for 1 hour. After cooling the reaction mixture was diluted with diethyl ether, transferred to a separatory funnel, and washed with aqueous 0.1 N hydrochloric acid, saturated aqueous solution of sodium bicarbonate, and then brine. The organic layer was dried with magnesium sulfate, filtered, and concentrated under reduced pressure. Column chromatography [silica gel; eluent hexanes-ethyl acetate (3:1)] provided the desired product (10.7 mg, 63%). $^1$H(CDCl$_3$) δ (ppm): 1.65-1.73 (m, 4H); 2.63 (t, 2H); 3.17 (t, 2H); 4.40 (t, 1H); 4.48 (t, 1H); 4.77 (t, 2H); 7.13 (d, 2H); 7.24 (d, 2H); 7.55 (1H); 7.82 (t, 1H); 7.92 (d, 1H); 8.13 (d, 1H); 8.78 (s, 1H). $^{13}$C (CDCl$_3$) δ (ppm): 27.19 (d, $^4J_{CF}$=4.5), 30.20 (d, $^3J_{CF}$=19.5), 35.15 (d, $^2J_{CF}$=27.0), 67.94, 84.17 (d, $^1J_{CF}$=163.3), 116.93, 123.75, 127.26, 127.84, 128.82, 129.23, 129.42, 133.77, 135.62, 138.21, 140.54, 151.08, 154.59. $^{19}$F(CDCl$_3$, CFCl$_3$ internal standard) δ (ppm): −218.59 (t of t, J=−27.6, −50.4).

Example 2

Synthesis of Pyridaben Analogs

Example 2A

Synthesis of Butyric acid 4-phenylbutyl ester

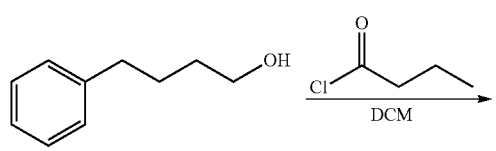

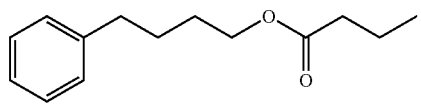

To 4-phenyl-1-butanol (7.0 g, 0.047 mol) was added anhydrous dichloromethane (20 mL). A solution of butyryl chloride (4.79 g, 0.045 mol) in anhydrous dichloromethane (20 mL) was added dropwise. The solution was stirred for 36 hours. At this point the reaction was concentrated under reduced pressure to give a crude oil. Column chromatography [silica gel; eluent hexanes-ethyl acetate (3:1)] provided the desired product (9.8 g, 94%) as a clear viscous liquid. $^1$H(CDCl$_3$) δ (ppm): 0.94 (t, 3H); 1.61-1.71 (m, 6H); 2.27 (t, 2H); 2.64 (t, 2H); 4.08 (t, 2H); 7.16-7.19 (m, 3H); 7.25-7.29 (m, 2H).

Example 2B

Synthesis of 4-(4-Hydroxybutyl)benzoic acid methyl ester

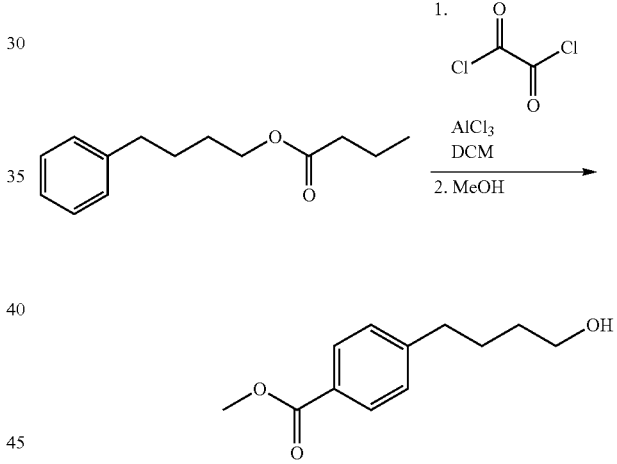

To aluminum chloride (6.7 g, 0.05 mol) in a dry 250 mL round bottom flask was added anhydrous dichloromethane (100 mL). The flask was cooled in a 0° C. ice bath. Oxalyl chloride (6.4 g, 0.05 mol) was added dropwise to the flask. The mixture was allowed to stir for 5 minutes. A solution of Example 2A (9.8 g, 0.044 mol) in anhydrous dichloromethane (50 mL) was then added dropwise. The mixture was allowed to stir for 4 hours at 0° C. The reaction mixture was poured into a separatory funnel containing ice and brine. The organic layer was washed with brine and dried over magnesium sulfate. Filtration and concentration under reduced pressure provided 9.1 g of yellow oil. 9.0 g of this oil was suspended in methanol and the pH adjusted to 2 and stirred for 48 hours. The reaction mixture was concentrated under reduced pressure. Column chromatography [silica gel; eluent hexanes-ethyl acetate (2.57:1)] provided the desired product (2.80 g, 31%) as a clear viscous liquid. $^1$H (CDCl$_3$) δ (ppm): 1.56-1.61 (m, 2H); 1.63-1.73 (m, 2H); 2.67 (t, 2H); 3.64 (t, 2H); 3.88 (s, 3H); 7.23 (d, 2H); 7.93 (d, 2H).

Example 2C

Synthesis of 4-[4-(tert-Butyldimethylsilanyloxy)butyl]benzoic acid methyl ester

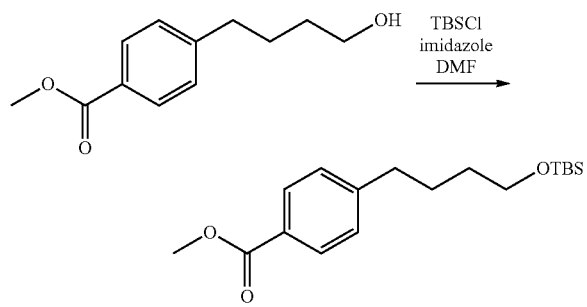

To Example 2B (1.0 g, 4.8 mmol) was added anhydrous dimethylformamide (10 mL), imidazole (0.5 g, 7.2 mmol) and tert-butyldimethylsilyl chloride (1.08 g, 7.3 mmol). The solution was stirred in a water bath for 2 hours. The reaction mixture was diluted with ethyl acetate, poured into a separatory funnel, washed with water (20 mL, 5×) then washed with a saturated sodium bicarbonate solution (20 mL, 2×). The organic layer was dried with magnesium sulfate, filtered, and concentrated under reduced pressure to give the desired product (1.17 g, 75%) which was used without further purification in the next step.

Example 2D

Synthesis of {4-[4-(tert-Butyldimethylsilanyloxy)butyl]phenyl}-methanol

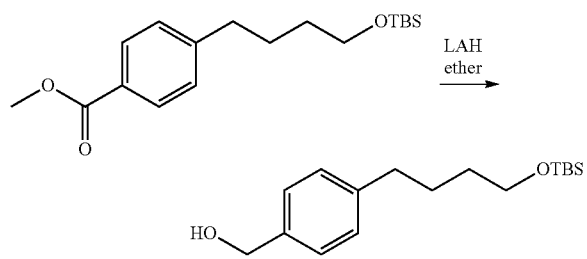

To Example 2C (1.17 g, 3.6 mmol) was added anhydrous diethyl ether (14 mL). The solution was cooled to 0° C. with an ice bath. Lithium aluminum hydride (0.28 g, 7.2 mmol) was added to the solution in portions. The mixture was stirred for 1 hour. To the reaction mixture was added distilled water (0.28 mL) and the mixture was stirred for 5 minutes. Next was added an aqueous 15% sodium hydroxide solution and the mixture was stirred for 5 minutes. Lastly distilled water (0.84 mL) was added and the mixture was stirred for 5 minutes. The white solid was removed by filtration. The filtrate was dried with magnesium sulfate, filtered, and concentrated to give 1.23 g of crude product. Column chromatography [silica gel; eluent hexanes-ethyl acetate (4:1)] provided the desired product (1.02 g, 96%) as a clear viscous liquid.

Example 2E

Synthesis of 2-tert-Butyl-5-{4-[4-(tert-butyldimethylsilanyloxy)butyl]benzyloxy}-4-chloro-2H-pyridazin-3-one

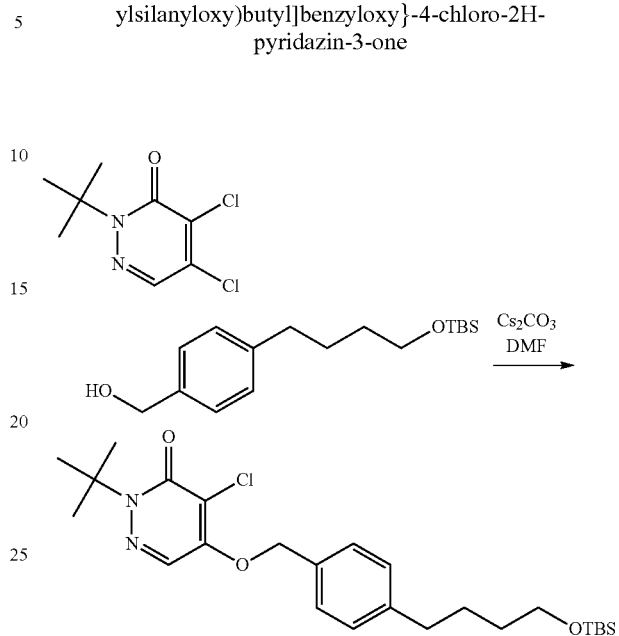

To a dry 25 mL round bottom flask, fitted with a reflux condenser, was added the product of Example 2D (0.41 g, 1.4 mmol), 2-tert-butyl-4,5-dichloro-2H-pyridazin-3-one (0.93 g, 4.2 mmol), cesium carbonate (1.37 g, 4.2 mmol), and anhydrous dimethylformamide (11 mL). The reaction flask was placed in a 68° C. oil bath and the reaction was stirred for 12 hours. The reaction flask was removed from the oil bath and allowed to cool. The mixture was diluted with ethyl acetate, transferred to a separatory funnel and washed with water (25 mL, 5×). The organic layer was dried with magnesium sulfate, filtered, and concentrated under reduced pressure to give 1.3 g of crude product. Column chromatography [silica gel; eluent hexanes-ethyl acetate (9:1)] provided the desired product (594 mg, 89%). $^1$H(CDCl$_3$) δ (ppm): 0.05 (s, 6H); 0.90 (s, 9H); 1.64 (s, 9H); 2.65 (t, 2H); 3.64 (t, 2H); 5.23 (s, 2H); 7.23 (d, 2H); 7.33 (d, 2H); 7.74 (s, 1H). $^{13}$C (CDCl$_3$) δ (ppm): 18.57, 26.19, 27.75, 28.09, 32.58, 35.61, 63.14, 66.57, 72.14, 118.46, 125.41, 127.44, 129.23, 132.38, 143.72, 154.02, 159.30.

Example 2F

Synthesis of 2-tert-Butyl-4-chloro-5-[4-(4-hydroxybutyl)-benzyloxy]-2H-pyridazin-3-one

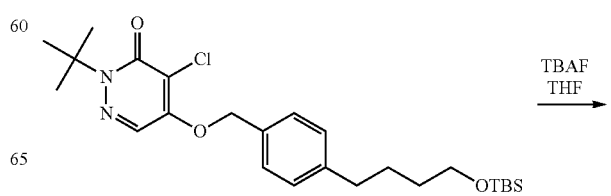

35

-continued

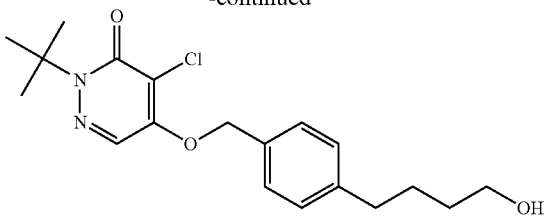

To the product of Example 2E (594 mg, 1.45 mmol) was added anhydrous tetrahydrofuran (3 mL) and a 1.0 M solution of tert-butylammonium fluoride in tetrahydrofuran (2.9 mL, 2.9 mmol). The solution was stirred for 1 hour then concentrated under reduced pressure. Column chromatography [silica gel; eluent pentane-ethyl acetate (1.8:1)] provided the desired product (410 mg, 77%). $^1$H (CDCl$_3$) δ (ppm): 1.61-1.64 (m, 11H); 1.67-1.74 (m, 2H); 2.68 (t, 2H); 3.68 (t, 2H); 5.23 (s, 2H); 7.23 (d, 2H); 7.33 (d, 2H); 7.74 (s, 1H). $^{13}$C (CDCl$_3$) δ (ppm): 27.43, 27.86, 32.56, 35.35, 62.74, 66.36, 71.88, 118.27, 125.18, 127.27, 128.99, 132.28, 143.17, 153.78, 159.07.

Example 2G

Synthesis of Toluene-4-sulfonic acid 4-[4-(1-tert-butyl-5-chloro-6-oxo-1,6-dihydro-pyridazin-4-yloxymethyl)-phenyl]-butyl ester

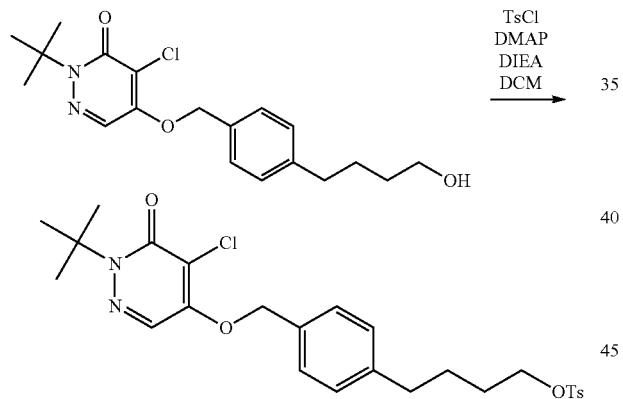

To a 5 mL round bottom flask was added the product of Example 2F (200 mg, 0.55 mmol), p-toluenesulfonyl chloride (125 mg, 0.66 mmol), 4-(dimethylamino)pyridine (80 mg, 0.66 mmol), diisopropylethylamine (85 mg, 0.66 mmol) and anhydrous dichloromethane (2 mL). The resulting solution was stirred for 2 hours. The reaction mixture was diluted with ethyl acetate, transferred to a separatory funnel and washed with a solution of aqueous 0.1 N hydrochloric acid and then washed with brine. The organic layer was dried with magnesium sulfate, filtered, and concentrated under reduced pressure to give 299 mg of crude product. Column chromatography [silica gel; eluent pentane-ethyl acetate (3:1)] provided the desired product (197 mg, 69%). $^1$H(CDCl$_3$) δ (ppm): 1.62-1.70 (m, 13H); 2.43 (s, 3H); 2.58 (t, 2H); 4.03 (t, 2H); 7.15 (d, 2H); 7.29-7.33 (m, 4H); 7.72 (s, 1H); 7.77 (d, 2H). $^{13}$C (CDCl$_3$) δ (ppm): 21.63, 26.98, 27.86, 28.34, 34.80, 66.37, 70.23, 71,81, 118.25, 125.12, 127.32, 127.87, 128.93, 129.82, 132.48, 133.15, 142.40, 144.72, 153.75, 159.05.

36

Example 2H

Synthesis of 2-tert-butyl-4-chloro-5-(4-(4-fluorobutyl)benzyl)oxy 3(2H) pyridazinone

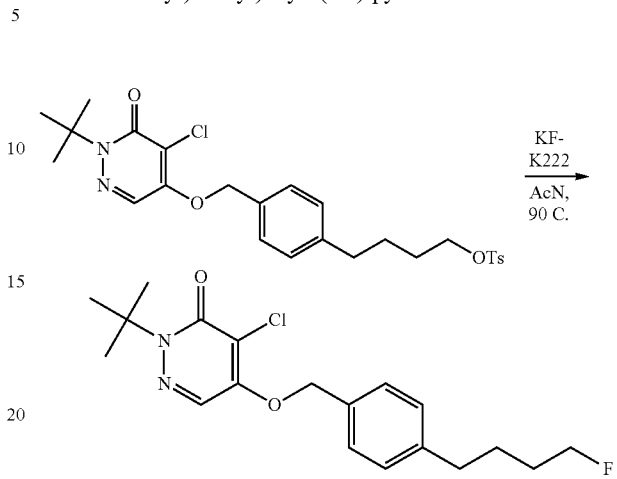

The product of Example 2G (57 mg, 0.10 mmol) was dissolved in 1 mL acetonitrile and to this was added a mixture of KF-K222 (1:1; 0.164 mmol) dissolved in 1 mL acetonitrile. The entire mixture was then immersed in an oil bath at 90° C. and heated at reflux for 15 minutes at which point the reaction was shown to be complete by TLC. The volatile components were removed in vacuo and the crude oil was purified by flash silica gel chromatography (hexanes-ethyl acetate (4:1)) to provide 28 mg of the desired product as a oil which solidified upon standing. $^1$H (CDCl$_3$) δ (ppm): 1.6 (s, 9H), 1.7 (m, 4H), 2.6 (t, 2H), 4.44 (d of t, 2H, J=47.4 & 6Hz), 5.2 (s, 2H), 7.2 (d, 2H, J=8.4 Hz), 7.3 (d, 2H, J=8.4 Hz), 7.71 (s, 1H). $^{13}$C (CDCl$_3$) δ (ppm): 26.8 ($^3J_{CF}$=4.65 Hz), 27.8, 29.8($^2J_{CF}$=19.8 Hz), 35.1, 66.3, 71.8, 83.8 ($^1J_{CF}$=163.8 Hz), 118.2, 125.1, 127.2, 128.9, 132.3, 142.8, 153, 159. $^{19}$F(CDCl$_3$, CFCl$_3$ as internal standard) δ (ppm): −218.6 (t of t, J=−27.6, −50.4).

Example 3

Synthesis of (±)-2-tert-butyl-4-chloro 5-(4-(1-fluoro-but-2-oxy)benzyl)oxy-3(2H)-pyridazinone

Example 3A

Synthesis of (±)-1-tert-butyldimethylsilyloxy-2-hydroxybutane

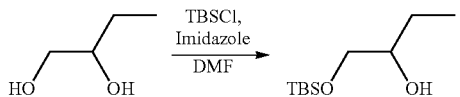

A 50 mL round bottom flask was charged with (±)-1,2-butanediol (1 g, 11.09 mmol) and to it was added dimethylformamide (8 mL) followed by tert-butyldimethylsilyl chloride (2.5 g, 16.64 mmol) and imidazole (1.88 g, 27.7 mmol). The reaction mixture was stirred for 10 hours after which it was diluted with dichloromethane and poured into a separatory funnel and washed with water (80 mL) and brine and dried over magnesium sulfate. After filtration and concentration the crude oil was purified by silica gel flash chromatography (hexanes:ethylacetate) to obtain 1 gm of pure desired product in 45% yield. $^1$H (CDCl$_3$) δ (ppm): 3.6 (m, 1H). 3.5 (m, 1H), 3.4 (m, 1H), 2.4 (s, 1H), 1.44 (m, 2H), 0.99 (t, 3H), 0.9 (s, 9H), 0.06 (s, 6H).

Example 3B

Synthesis of (±)-4-(1-tertbutyldimethylsilyloxy but-2-oxy)methylbenzoate

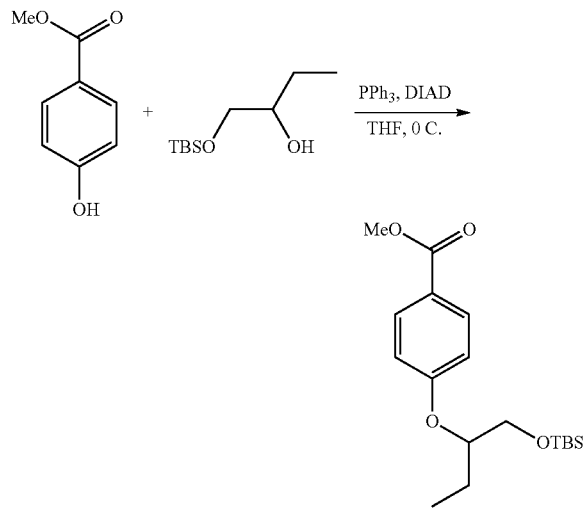

4-Hydroxymethylbenzoate (1.1 g, 7.34 mmol), the product of Example 3A (0.75 g, 3.67 mmol) and triphenylphosphine (1.972 g, 7.34 mmol) were added to a round bottom flask and 8 mL tetrahydrofuran was added. The flask was cooled in an ice bath to 0° C. after which diisopropylazodicarboxylate (1.485 g, 7.34 mmol) was added via syringe. The reaction mixture was stirred for 2 hours after which the reaction was deemed complete by thin layer chromatography. All the solvent was removed under reduced pressure and the crude oil directly subjected to purification by silica gel flash chromatography (hexanes : diethyl ether) to obtain 1.0 gm (83%) of the desired compound as a thick oil. $^1$H (CDCl$_3$) δ (ppm): 7.9 (d, 2H), 6.9 (d, 2H), 4.3 (p, 1H, J=5.4 Hz), 3.9 (s, 3H), 3.7 (2H), 1.78 (m, 1H), 1.7 (m, 1H), 0.9 (t, 3H, J=7.8 Hz), 0.89 (s, 9H), 0.05 (s, 3H), 0.01 (s, 3H). $^{13}$C (CDCl$_3$) δ (ppm): 166.8, 162.8, 131.5, 122.3, 115.2, 80, 64.5, 51.7, 25.8, 24.1, 18.2, 9.5, −5.3.

Example 3C

Synthesis of (±)-4-(1-tertbutyldimethylsilyloxy but-2-oxy)benzylalcohol

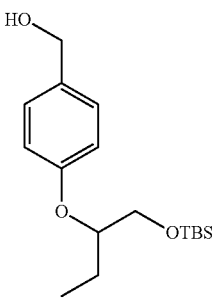

To a solution of the product of Example 3B (1 g, 2.95 mmol) in ether (15 mL) was added lithium aluminum hydride (0.336 g, 8.8 mmol) and the mixture was stirred under nitrogen for 1.5 hours. The reaction was complete as shown by TLC by this time and was quenched by addition of 0.336 mL water, 0.336 mL of 15% NaOH solution and 1.00 mL water in succession. The resulting mixture was stirred for an additional 20 minutes after which the white precipitate formed was filtered and washed with ether. The filtrate was then dried over magnesium sulfate. Filtration and removal of the solvent gave 0.50g (54%) of the desired product as a white solid. $^1$H (CDCl$_3$) δ (ppm): 7.2 (d, 2H), 6.9 (d, 2H), 4.3 (p, 1H), 3.77 (d of d, 1H), 3.66 (d of d, 1H), 1.77-1.72 (m, 1H), 1.68-1.61 (m, 1H), 1.5 (t, 1H, J=5.4 Hz), 0.9 (t, 3H, J=7.8 Hz), 0.89 (s, 9H), 0.04 (s, 3H), 0.01 (s, 3H). $^{13}$C (CDCl$_3$) δ (ppm): 158.5, 133, 128.4, 116.1, 80.1, 65, 64.5, 25.8, 24.1, 18.2, 9.5, −5.3.

Example 3D

Synthesis of (±)-2-tert-butyl 4-chloro 5-(4-(1-tertbutyldimethylsilyloxy but-2-oxy) benzyl)oxy 3(2H)-pyridazinone

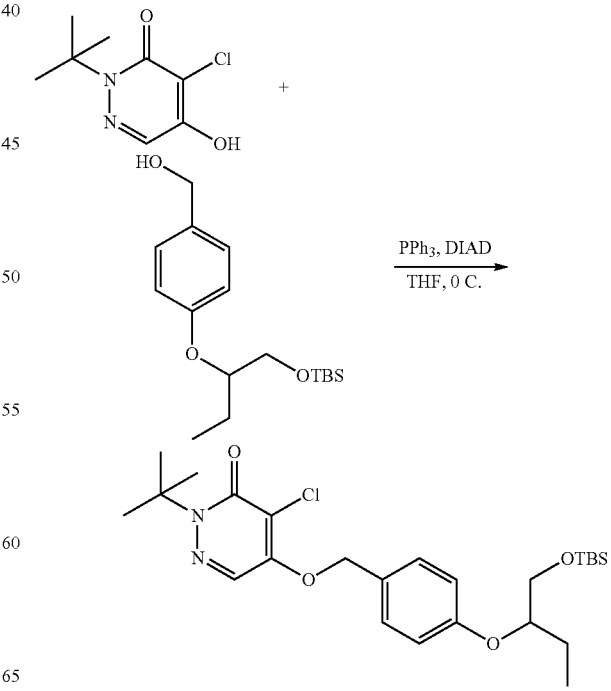

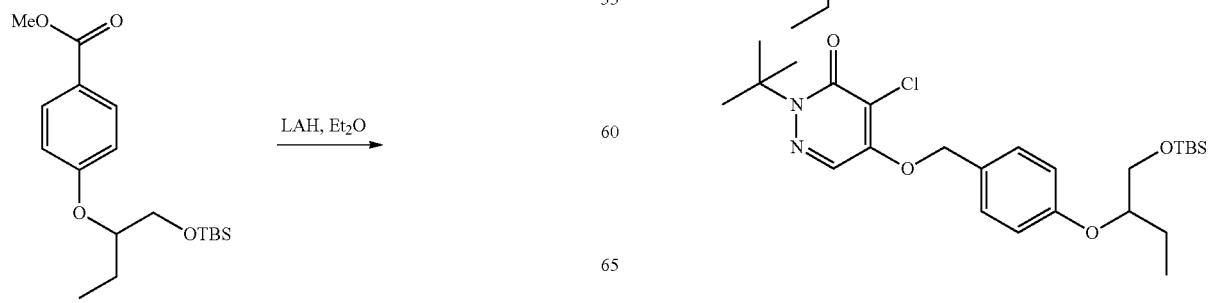

(±)-2-Tert-butyl-4-chloro-5-hydroxy-3(2H)-pyridazinone (0.48 g, 2.417 mmol) was charged to a 100 mL round bottom flask and tetrahydrofuran (40 mL) was added. After the solution turned clear, Example 3C (0.5 g, 1.611 mmol) and triphenylphosphine (0.633 g, 2.417 mmol) were added to the flask and the flask was cooled to 0° C. Diisopropyl azodicarboxylate (0.488 g, 2.417 mmol, 0.468 mL) was then added via a syringe and the reaction was stirred for two hours after which time it was shown to be complete by TLC. The contents of the flask were then concentrated in vacuo and the crude oil obtained was purified by flash chromatography using silica gel (hexanes:ethyl acetate) to obtain 0.33 g of the desired compound as an oil. $^1$H (CDCl$_3$) δ (ppm): 7.72 (s, 1H), 7.2 (d, 2H), 6.9 (d, 2H), 5.2 (s, 2H), 4.2 (p, 1H), 3.75 (d of d, 1H), 3.68 (d of d, 1H), 1.75 (m, 2H), 1.65 (m, 1H), 1.6 (s, 9H), 0.99 (t, 3H), 0.85 (s, 9H), 0.04 (s, 3H), 0.02 (s, 3H). $^{13}$C (CDCl$_3$) δ (ppm): 159.6, 159.3, 154, 129, 126.9, 125, 118.5, 116.5, 80.3, 72.1, 66.5, 64.8, 28.1, 26, 24.4, 18.4, 9.6, −5.3.

Example 3E

Synthesis of (±)-2-tert-butyl-4-chloro-5-(4-(1-hydroxy-but-2-oxy)benzyl)oxy-3(2H)-pyridazinone

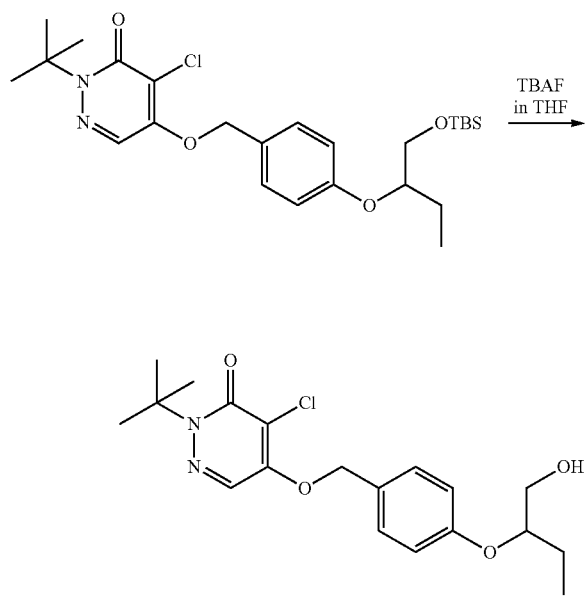

To the product of Example 3D (0.3 g, 0.6 mmol) in a 10 mL round bottom flask was added tetrahydrofuran (2 mL). Upon solution, tetrabutylammonium fluoride (1.8 mmol, 1.8 mL, 1M solution in THF) was added and the reaction mixture was stirred for 90 minutes. The contents were then concentrated under reduced pressure and the crude mixture purified by flash chromatography using silica gel (hexanes:ethyl acetate) to obtain 185 mg (80%) of pure desired product. $^1$H (CDCl$_3$) δ (ppm): 7.74 (s, 1H), 7.3 (d, 2H), 6.9 (d, 2H), 5.2 (s, 2H), 4.3 (m, 1H), 3.81-3.77 (two br s, 2H), 1.84 (br t, 1H), 1.77-1.69 (m, 2H), 1.64 (s, 9H), 0.98 (t, 3H); $^{13}$C (CDCl$_3$) δ (ppm): 159.2, 158.9, 153.9, 129.2, 127.5, 125.4, 116.6, 80.4, 71.9, 66.5, 64.2, 28, 23.5, 9.7.

Example 3F

Synthesis of (±)-2-tert-butyl 4-chloro 5-(4-(1-tosyloxy-but-2-oxy)benzyl)oxy 3(2H)-pyridazinone

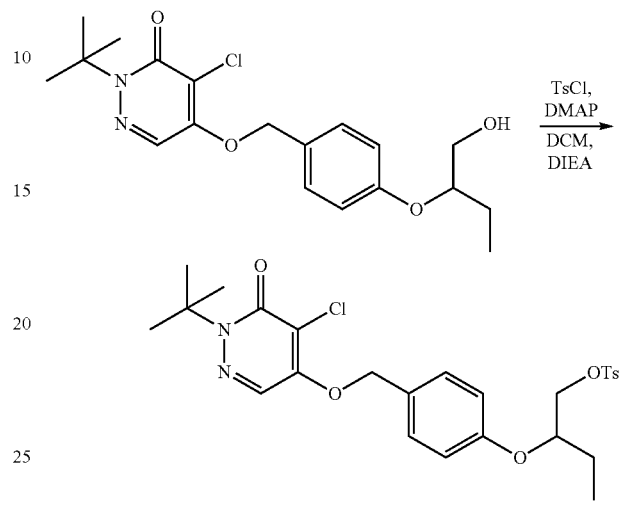

Into a 10 mL round bottom flask was added the product of Example 3E (0.05 g, 0.13 mmol) followed by dichloromethane (2 mL). Toluenesulfonyl chloride (0.075 g, 0.39 mmol), 4-N,N-dimethylaminopyridine (0.048 g, 0.39 mmol) and diisopropylethylamine (0.05 g, 0.39 mmol, 68.7 µl) were then added in succession to the reaction mixture and this was stirred for 35 minutes. Water was then added to the mixture and the solution poured into a separatory funnel and the layers separated. The organic layer was washed with water and brine and dried over magnesium sulfate. The crude oil obtained after filtration and concentration was purified by silica gel flash chromatography (hexanes:ethyl acetate) to obtain 54 mg (77%) of the desired compound as a thick colorless oil. $^1$H (CDCl$_3$) δ (ppm): 7.74 (3H, two singlets), 7.3 (m, 4H), 6.8 (d, 2H), 5.2 (s, 2H), 4.38 (p, 1H), 4.15 (m, 2H), 2.44 (s, 3H), 1.72 (m, 2H), 1.6 (s, 9H), 0.95 (t, 3H); $^{13}$C (CDCl$_3$) δ (ppm): 159.2, 158.5, 153.9, 145.1, 133, 130, 129, 128.1, 127.2, 125.4, 118.5, 116.5, 71.9, 70.2, 66.6, 28.1, 24.2, 21.8, 9.4.

Example 3G

Synthesis of (±)-2-tert-butyl-4-chloro 5-(4-(1-fluoro-but-2-oxy)benzyl)oxy-3(2H)-pyridazinone

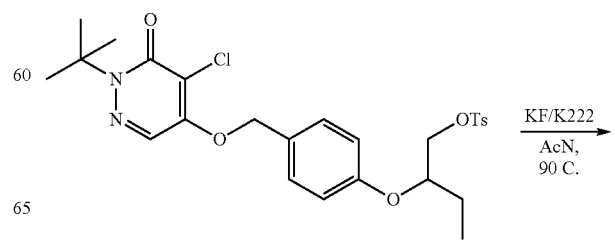

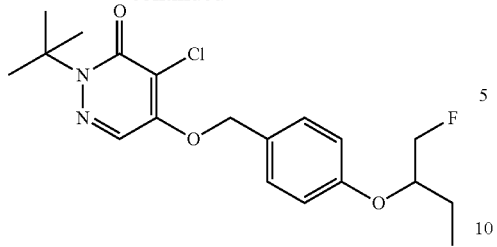

The product of Example 3F (28 mg, 52.4 μmol) was dissolved in 0.5 mL acetonitrile in a 5 mL flask and to this was added a solution of potassium fluoride (4.5 mg, 78.6 μmol) and Kryptofix 222 (29.6 mg, 78.6 μmol) in 0.5 mL acetonitrile. The above solution was then immersed in a oil bath preheated to 90° C. The reaction was allowed to stir for 90 minutes after which all the volatiles were removed under reduced pressure and the crude mixture purified by preparative thin layer chromatography to obtain 13 mg (65%) of pure desired compound. $^1$H (CDCl$_3$) δ (ppm): 7.72 (s, 1H), 7.3 (d, 2H), 6.9 (d, 2H), 5.23 (s, 2H), 4.57-4.59 (m, 2H), 4.4 (m, 4H), 1.74 (m, 2H), 1.6 (s, 9H), 1.0 (t, 3H). $^{13}$C (CDCl$_3$) δ (ppm): 159, 158.7, 153.7, 129, 127.5, 125.2, 118.3, 116.4, 83.85 (d, $^1J_{CF}$=172.2), 78, 71.1, 66.3, 27.8, 23.2, 9.48. $^{19}$F (CDCl$_3$, CFCl$_3$ as internal standard) δ (ppm): −228 (d of t, J=−19, −60 Hz).

Example 4

Synthesis of 2-tert-butyl-4-chloro-5-[4-(3-fluoropropoxy)benzyloxyl-2H-pyridazin-3-one Example 4A Synthesis of 4-(3-hydroxypropoxy)-benzoic acid methyl ester

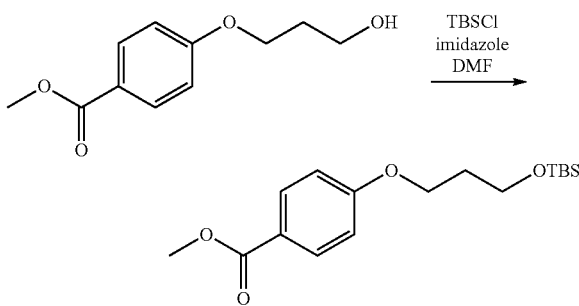

To a 250 mL flask was added 3-bromo-1-propanol (4.17 g, 0.03 mol), anhydrous dimethylformamide (40 mL), methyl-4-hydroxybenzoate (3.0 g, 0.02 mol) and potassium carbonate (4.15 g, 0.03 mol). The flask was placed in a 50° C. oil bath and stirred for 12 hours. After cooling the reaction was diluted with ethyl acetate, transferred to separatory funnel, washed with aqueous 0.1 N hydrochloric acid, water then brine. The organic layer was dried with magnesium sulfate, filtered, and concentrated under reduced pressure to give 5.14 g of crude oil. Column chromatography [silica gel; eluent hexanes-ethyl acetate (1.68:1)] provided the desired product (1.25 g, 30%) as a white powder. $^1$H (CDCl$_3$) δ (ppm): 2.04-2.08 (m, 2H); 3.86-3.88 (m, 5H); 4.17 (t, 2H); 6.91 (d, 2H); 7.98 (d, 2H); $^{13}$C (CDCl$_3$) δ (ppm): 31.89, 51.81, 59.88, 65.50, 114.06, 122.67, 131.57, 162.60, 166.84.

Example 4B

Synthesis of 4-[3-(tert-Butyldimethylsilanyloxy)propoxy]benzoic acid methyl ester

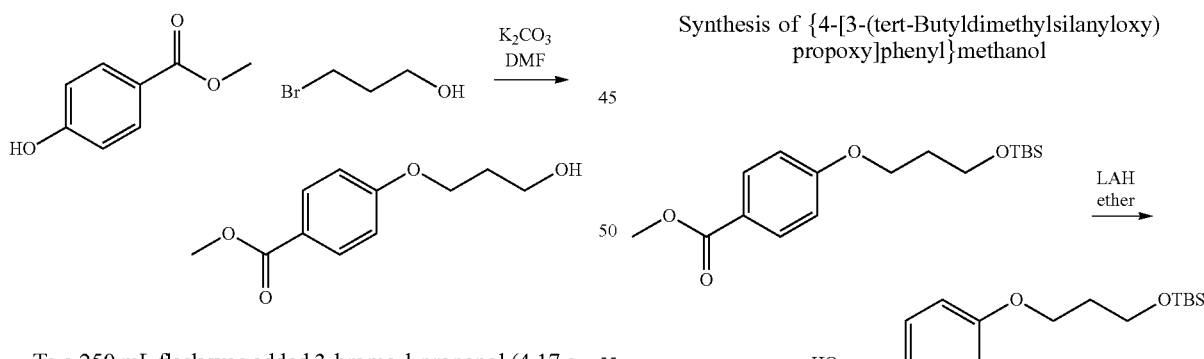

To a 50 mL flask was added Example 4A (300 mg, 1.4 mmol), anhydrous dimethylformamide (4 mL), tert-butyldimethylsilyl chloride (317 mg, 2.1 mmol), and imidazole (146 mg, 2.1 mmol). The resulting solution was stirred for 2 hours. At this point the reaction was diluted with ethyl acetate and transferred to a separatory funnel. The organic phase was washed with aqueous 0.1 N hydrochloric acid (2×), water(2×), then brine. The organic layer was then dried over magnesium sulfate, filtered, and concentrated. Column chromatography [silica gel; eluent hexanes-ethyl acetate (9.5:1)] provided the desired product (413 mg, 91%). $^1$H (CDCl$_3$) δ (ppm): 0.03 (s, 6H); 0.87 (s, 9H); 1.97-2.01 (m, 2H); 3.79 (t, 2H); 3.87 (s, 3H); 4.11 (t, 2H); 6.90 (d, 2H); 7.97 (d, 2H); $^{13}$C (CDCl$_3$) δ (ppm): 18.30, 25.89, 32.3, 51.78, 59.27, 64.67, 114.08, 122.43, 131.56, 162.90, 166.90.

Example 4C

Synthesis of {4-[3-(tert-Butyldimethylsilanyloxy)propoxy]phenyl}methanol

Example 4B (396 mg, 1.22 mmol) was added to a dry 50 mL flask along with anhydrous diethyl ether (10 mL). The flask was lowered into an ice bath. Lithium aluminum hydride (93 mg, 2.44 mmol) was added in portions to the reaction flask. The mixture was allowed to stir in the bath for 2 hours. The reaction was quenched with water (0.093 mL), aqueous 15% sodium hydroxide (0.093 mL) then water (0.279 mL). The white solid was filtered off and the filtrate was dried over magnesium sulfate, filtered, and concentrated to give the desired product (291 mg, 80%). $^1$H(CDCl$_3$) δ

(ppm): 0.04 (s, 6H); 0.88 (s, 9H); 1.95-1.99 (m, 2H); 3.79 (t, 2H); 4.05 (t, 2H); 4.60 (s, 2H); 6.88-6.89 (m, 2H); 7.25-7.27 (m, 2H); (CDCl$_3$) δ (ppm): 18.30, 25.91, 32.41, 59.50, 64.57, 65.10, 114.59, 128.60, 132.97, 158.75.

Example 4D

Synthesis of 2-tert-butyl-4-chloro-5-{4-[3-(tert-butyldimethylsilanyloxy)propoxy]benzyloxy}-2H-pyridazin-3-one

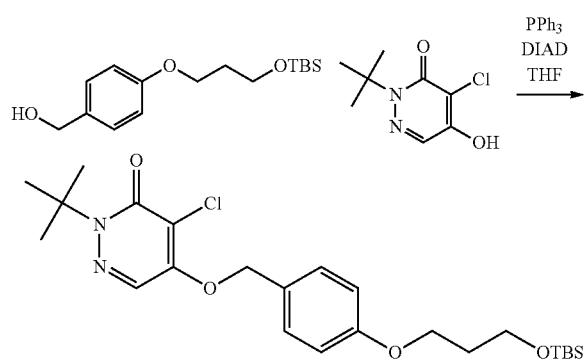

To a dry 25 mL flask was added Example 4C (211 mg, 0.71 mmol) and anhydrous tetrahydrofuran (3 mL). The flask was cooled in an ice bath. To the flask was added triphenylphosphine (187 mg, 0.71 mmol) and 2-tert-butyl-4-chloro-5-hydroxy-2H-pyridazin-3-one (142 mg, 0.71 mmol). Lastly, diisopropyl azodicarboxylate (144 mg, 0.71 mmol) was added. The reaction mixture was allowed to stir in the ice bath for 1 hour. At this point the mixture was diluted with diethyl ether and transferred to a separatory funnel. The organic solution was washed with water and then brine, dried over magnesium sulfate, filtered, and concentrated under reduced pressure. Column chromatography [silica gel; eluent hexanes-ethyl acetate (9:1)] provided the desired product (106 mg, 31%). $^1$H (CDCl$_3$) δ (ppm): 0.03 (s, 6H); 0.87 (s, 9H); 1.62 (s, 9H); 1.95-1.99 (m, 2H); 3.79 (t, 2H); 4.06 (t, 2H); 5.23 (s, 2H); 6.91-6.92 (m, 2H); 7.30-7.31 (m, 2H); 7.72 (s, 1H); $^{13}$C (CDCl$_3$) δ (ppm): 18.29, 25.90, 27.87, 32.34, 59.41, 64.63, 66.30, 71.89, 114.90, 118.34, 125.34, 126.68, 128.92, 153.79, 159.07, 159.55.

Example 4E

Synthesis of 2-tert-butyl-4-chloro-5-[4-(3-hydroxypropoxy)-benzyloxy]-2H-pyridazin-3-one

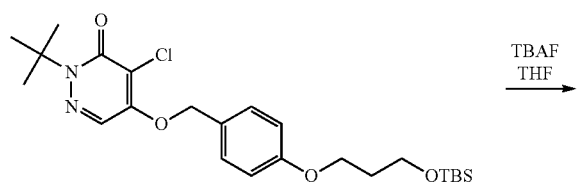

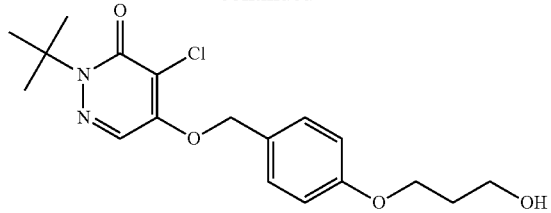

To a dry 10 mL flask was added Example 4D (100 mg, 0.21 mmol) along with anhydrous tetrahydrofuran (2 mL). To the flask was added a solution of 1.0 M tetrabutylammonium fluoride in tetrahydrofuran (0.42 mL, 0.42 mmol). The solution was stirred for 2 hours. At this point the reaction was concentrated under reduced pressure. Preparatory thin layer chromatography [silica gel; eluent hexanes-ethyl acetate (1:1)] provided the desired product (57.8 mg, 76%). $^1$H(CDCl$_3$) δ (ppm): 1.62 (s, 9H); 2.02-2.06 (m, 2H); 3.86 (t, 2H); 4.13 (t, 2H); 5.30 (s, 2H); 6.92-6.93 (m, 2H); 7.31-7.32 (m, 2H); 7.71 (s, 1H); $^{13}$C (CDCl$_3$) δ (ppm): 27.87, 31.97, 60.24, 65.67, 66.34, 71.81, 114.91, 118.37, 125.31, 127.06, 128.98, 153.76, 159.07, 159.27.

Example 4F

Synthesis of toluene-4-sulfonic acid 3-[4-(1-tert-butyl-5-chloro-6-oxo-1,6-dihydro-pyridazin-4-yloxymethyl)phenoxy]propyl ester

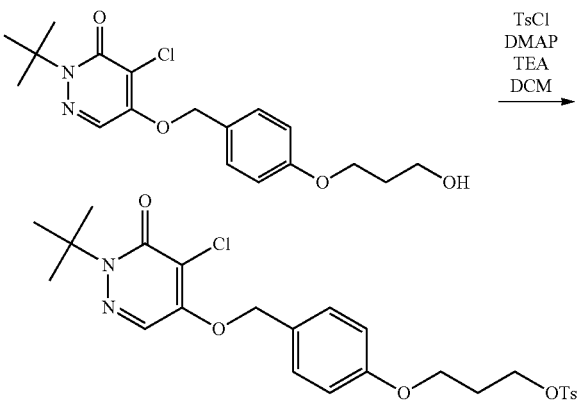

To a dry 5 mL flask was added Example 4E (40 mg, 0.11 mmol), 4-methyl-benzenesulfonyl chloride (31 mg, 0.16 mmol), 4-(dimethylamino)pyridine (20 mg, 0.16 mmol), diisopropylethylamine (16.6 mg, 0.16 mmol) and anhydrous dichloromethane (0.6 mL). The resulting solution was stirred for 1 hour. The reaction mixture was concentrated under reduced pressure. Preparatory thin layer chromatography [silica gel; eluent pentane-ethyl acetate (3:2)] provided the desired product (18.6 mg, 33%). $^1$H (CDCl$_3$) δ (ppm): 1.62 (s, 9H); 2.09-2.13 (m, 2H); 2.37 (s, 3H); 3.95 (t, 2H); 4.23 (t, 2H); 5.22 (s, 2H); 6.78 (d, 2H); 7.23 (d, 2H); 7.29 (d, 2H); 7.73-7.75 (m, 3H). $^{13}$C (CDCl$_3$) δ (ppm): 21.60, 27.85, 28.81, 63.15, 66.35, 66.87, 71.75, 114.76, 118.27, 125.18, 127.11, 127.83, 128.94, 129.80, 132.79, 144.80, 163.72, 158.90, 159.03.

Example 4G

Synthesis of 2-tert-butyl-4-chloro-5-[4-(3-fluoro-propoxy)benzyloxy]-2H-pyridazin-3-one

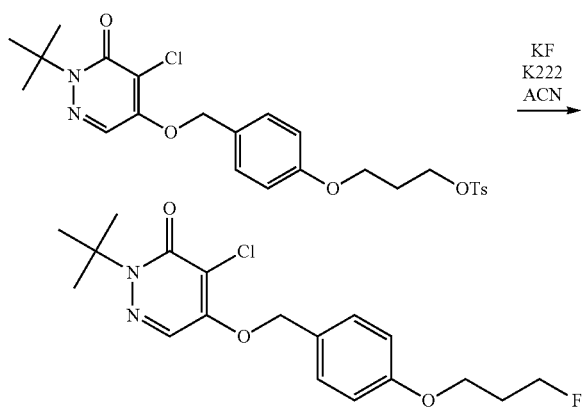

To a scintillation vial containing a suspension of Example 4F (4.5 mg, 8.64×10⁻³ mmol) in anhydrous acetonitrile (0.25 mL) was added a solution of potassium fluoride (1.6 mg, 4.07×10⁻² mmol) and kryptofix (15.0 mg, 4.07×10⁻² mmol) in anhydrous acetonitrile (0.25 mL). The vial was capped and lowered into a 90° C. oil bath. The reaction was allowed to stir for 40 minutes. The reaction was cooled and concentrated under reduced pressure. Preparatory thin layer chromatography [silica gel; eluent pentane-ethyl acetate (3:2)] provided the desired product (0.8 mg, 25%). $^1$H(CDCl$_3$) δ (ppm): 1.62 (s, 9H); 2.14-2.20 (m, 2H); 4.09-4.11 (m, 2H); 4.60 (t, 1H); 4.68 (t, 1H); 5.24 (s, 2H); 6.92 (d, 2H); 7.32 (d, 2H); 7.72 (s, 1H); $^{19}$F(CDCl$_3$, CFCl$_3$ as internal standard) δ (ppm): −222.66 (t of t, J=28.2, −50.4).

Example 5

Synthesis of 2-tert-butyl-4-chloro-5-[4-(2-fluoro-ethoxymethyl)-benzyloyl-2H-pyridazin-3-one

Example 5A

Synthesis of 4-(2-hydroxyethoxymethyl)benzoic acid methyl ester

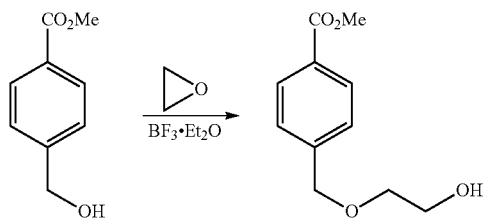

To a two-neck round bottom flask, which was equipped with a Dewar condenser, a solution of 4-hydroxymethylbenzoic acid methyl ester (2.50 g, 0.015 mol) in anhydrous dichloromethane (30 mL) was cooled to −10° C. in a salt/ice bath. Ethylene oxide (1.10 mL) was added to the cooled stirring solution dropwise followed by the addition of boron trifluoride etherate (0.51 ml). The reaction mixture was stirred for 45 minutes and then warmed to room temperature for 30 minutes to boil off any excess of ethylene oxide in the reaction mixture. The reaction mixture was then diluted with brine. The aqueous layer was extracted with dichloromethane (3 times). All of the organic layers were combined, dried over Na$_2$SO$_4$, filtered, and concentrated to provide an oil. The crude material was purified using silica gel chromatography (4:1 pentane:ethyl acetate) to provide the desired product (537 mg, 2.56 mmol) in 17% yield. $^1$H (CDCl$_3$ 8.36☐, 600 MHz): δ (2H, d, J=8.4 Hz), 7.41 (2H, d, J=8.5 Hz), 4.62 (3H, s), 3.92 (2H, s), 3.78 (m, 2H), 3.63 (2H, m); $^{13}$C (CDCl$_3$ 167.1, 143.5, 130.0, 129.8, 127.5, 72.9, 72.0, ☐, 150 MHz): δ 62.1, 52.3.

Example 5B

Synthesis of 4-[2-(tert-butyldimethylsilanyloxy)ethoxymethyl]benzoic acid methyl ester

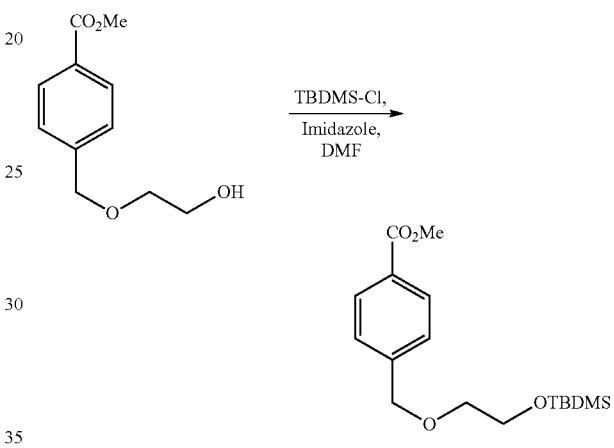

To a solution of the product of Example 5A (544.5 mg, 2.59 mmol) in anhydrous DMF (26 mL) was added imidazole (264 mg, 3.89 mmol) and TBDMS-Cl (586 mg, 3.89 mmol). The reaction mixture stirred at room temperature overnight and was quenched with water. The aqueous layer was extracted with ethyl acetate (3×). All combined organic layers were dried over Na$_2$SO$_4$, filtered, and concentrated. The crude material was purified using silica gel chromatography (4:1 pentane:ethyl acetate) to provide the desired product (677.5 mg, 2.19 mmol) in 84% yield. $^1$H (CDCl$_3$ 8.01☐, 600 MHz): δ (2H, d, J=8.3 Hz), 7.42 (2H, d, J=8.4 Hz), 4.63 (2H, s), 3.91 (2H, s), 3.82 (2H, t, J=5.0), 3.58 (2H, t, J=5.1 Hz), 0.91 (9H, s), 0.07 (6H, s); $^{13}$C (CDCl$_3$ 166.5, 143.5, 129.2, 128.8, 126.5, 72.1, 71.6, ☐, 150 MHz): δ 62.3, 51.5, 25.4, 17.9, −5.8.

Example 5C

Synthesis of {4-[2-(tert-butyldimethylsilanyloxy)ethoxymethyl]phenyl}methanol

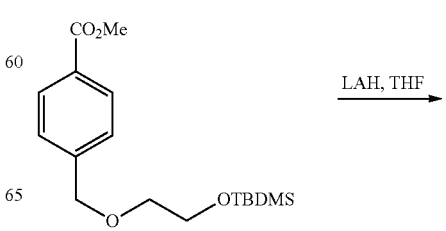

-continued

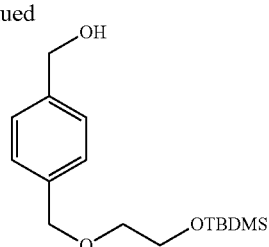

To a solution of the product of Example 5B (670 mg, 2.18 mmol) dissolved in anhydrous THF (22 mL) was added a solution of LAH (1.0 M solution in THF, 2.18 mL, 2.18 mmol) dropwise. After completion of addition the reaction mixture was stirred at room temperature for 3 hours. The reaction mixture was diluted with water. The aqueous layer was extracted with ethyl acetate (3×). All combined organic layers were dried over $Na_2SO_4$, filtered, and concentrated to provide an oil (587 mg, 1.98 mmol), which was used in the next step without any further purification (91% yield). $^1$H (CDCl$_3$ 7.34 (4H, s), 4.68 (2H, s), 4.57 (2H, s), 3.80☐, 600 MHz): δ (2H, t, J=5.2 Hz), 3.56 (2H, t, J=5.3 Hz), 1.69 (1H, br s), 0.90 (9H, s), 0.07 (6H, s); $^{13}$C (CDCl$_3$ 140.4, 138.3, 128.0, 127.2, 73.2, 71.9, 65.4, ☐, 150 MHz): δ 63.0, 26.2, 18.6, −5.0. ☐☐

Example 5D

Synthesis of 2-tert-butyl-5-{4-[2-(tert-butyldimethylsilanyloxy)ethoxymethyl]benzyloxy}-4-chloro-2H-pyridazin-3-one

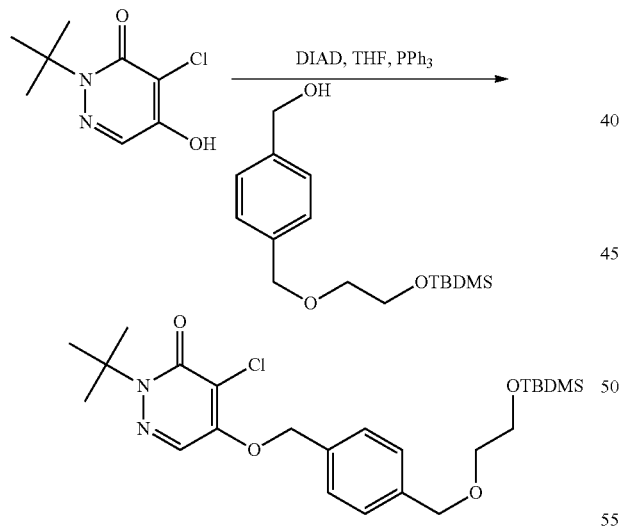

To solution of the product of Example 5C (437 mg, 1.48 mmol) and 2-tert-butyl-4-chloro-5-hydroxy-2H-pyridazin-3-one (250 mg, 1.23 mmol) dissolved in anhydrous THF (12 mL) was added solid PPh$_3$ (485 mg, 1.85 mmol) and diisopropyl azodicarboxylate (DIAD, 0.358 mL, 1.85 mmol). After completion of addition the reaction mixture continued to stir at room temperature. After 20 hours, the reaction mixture was diluted with water. The aqueous layer was separated and extracted with ethyl acetate (3×). All combined organic layers were dried over $Na_2SO_4$, filtered, and concentrated to provide an oil. The crude material was purified using silica gel chromatography (4:1 pentane: ethyl acetate) to provide the desired product 528 mg, 1.10 mmol) in 89% yield. $^1$H (CDCl$_3$ 7.70 (1H, s), 7.38 (4H, m), 5.30 (2H, s), 4.58☐, 600 MHz): δ (2H, s), 3.80 (2H, t, J=5.4 Hz), 3.57 (2H, t, J=5.4 Hz), 1.63 (9H, br s), 0.90 (9H, s), 0.07 (6H, s); $^{13}$C (CDCl$_3$159.0, 153.7, 138.8, 134.4, 128.3, 127.3, ☐, 150 MHz): δ 125.1, 118.5, 72.8, 71.7, 71.6, 66.4, 61.9, 29.7, 27.9, 25.6, −5.1; HRMS calcd for $C_{24}H_{37}ClN_2O_4Si$: 481.228389, found 481.2282.

Example 5E

Synthesis of 2-tert-butyl-4-chloro-5-[4-(2-hydroxyethoxymethyl)benzyloxy]-2H-pyridazin-3-one

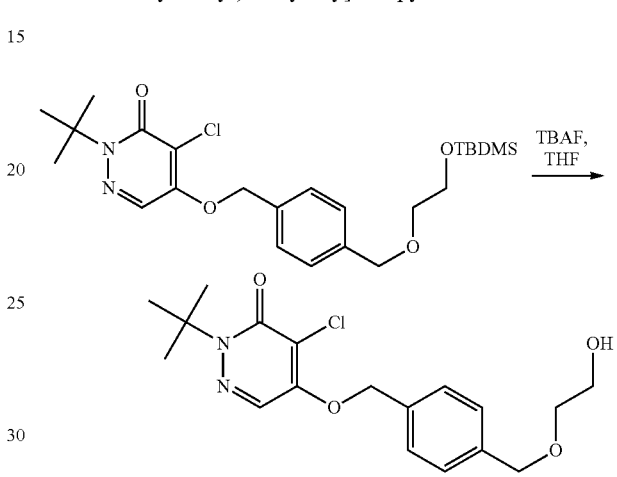

To a solution of the product of Example 5D (528 mg, 1.09 mmol) dissolved in anhydrous THF (11 mL) was added a solution of TBAF (1.0 M solution in THF, 1.65 mL, 1.65 mmol) dropwise. After completion of addition the reaction was stirred at room temperature for 1 hour and then quenched with water. The aqueous layer was separated and extracted with ethyl acetate (3×). All combined organic layers were dried over $Na_2SO_4$, filtered, and concentrated to provide an oil. The crude material was purified using silica gel chromatography (4:1 hexanes: ethyl acetate) to provide the desired product (311 mg, 0.850 mmol) in 78% yield. $^1$H (CDCl$_3$, 600 MHz): δ 7.70 (1H, s), 7.38 (4H, m), 5.30 (2H, s), 4.56 (2H, s), 3.76 (2H, t, J=4.9 Hz), 3.60 (2H, t, J=4.8 Hz), 2.00 (1H, br s), 1.61 (9H, br s); $^{13}$C (CDCl$_3$159.0, 153.6,☐, 150 MHz): δ 138.8, 134.4, 128.2, 127.2, 125.1, 118.3, 72.8, 71.6, 71.6, 66.4, 61.9, 27.8; HRMS calcd for $C_{18}H_{23}ClN_2O_4$: 367.141911, found 367.1419.

Example 5F

Synthesis of toluene-4-sulfonic acid 2-[4-(1-tert-butyl-5-chloro-6-oxo-1,6-dihydro-pyridazin-4-yloxymethyl)-benzyloxy]-ethyl ester

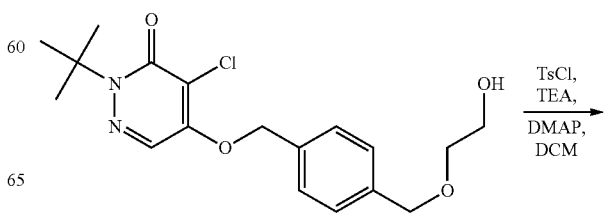

-continued

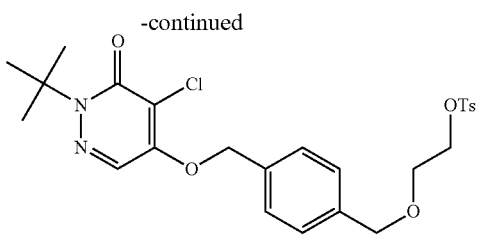

To a solution of the product of Example 5E (200 mg, 0.546 mmol) dissolved in anhydrous dichloromethane (5.50 mL) was added TsCl (125 mg, 0.656 mmol), DMAP (100 mg, 0.819 mmol) and triethylamine (0.091 mL, 0.656 mmol). The reaction mixture continued stirring at room temperature. After 22 hours the reaction mixture was diluted with water. The aqueous layer was separated and extracted with ethyl acetate (3×). All combined organic layers were dried over $Na_2SO_4$, filtered, and concentrated to provide an oil. The crude material was purified using silica gel chromatography (3:2 pentane:ethyl acetate) to provide the desired product (232 mg, 0.447 mmol) in 82% yield. $^1$H (CDCl$_3$ 7.79☐, 600 MHz): δ (2H, d, J=8.3 Hz), 7.71 (1H, s), 7.38 (2H, d, J=8.2 Hz), 7.32 (4H, m), 5.30 (2H, s), 4.50 (2H, s), 4.21 (2H, m), 3.69 (2H, m), 2.43 (3H, s), 1.63 (9H, br s); $^{13}$C (CDCl$_3$ 159.0, 153.7, 144.8, 138.8, ☐, 150 MHz): δ 134.4, 133.1, 129.8, 128.1, 128.0, 127.2, 125.1, 118.4, 72.8, 71.7, 69.2, 67.8, 66.4, 27.9, 21.6; HRMS calcd for $C_{25}H_{29}ClN_2O_6$: 521.150762, found 521.1503.

Example 5G

Synthesis of 2-tert-butyl-4-chloro-5-[4-(2-fluoro-ethoxymethyl)-benzyloy]-2H-pyridazin-3-one

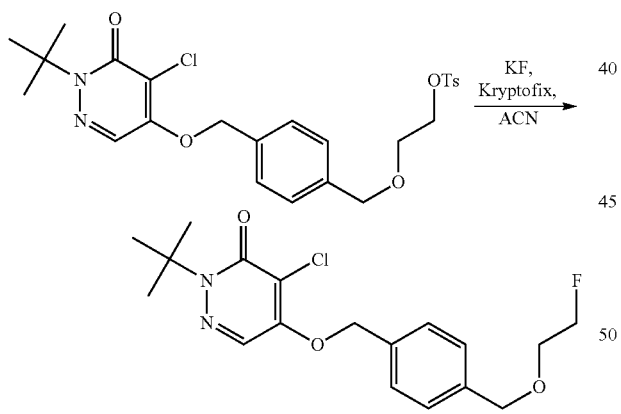

To a solution of the product of Example 5F (50 mg, 0.096 mmol) in anhydrous acetonitrile (1.0 mL) was added KF (11.2 mg, 0.192 mmol) and Kryptofix (72.4 mg, 0.192 mmol). After completion of addition the reaction mixture was heated to 90° C. After 10 minutes, the reaction mixture was cooled down to room temperature and diluted with water. The aqueous layer was separated and extracted with ethyl acetate (3×). All combined organic layers were dried over $Na_2SO_4$, filtered, and concentrated to provide an oil. The crude material was purified using silica gel chromatography (4:1 pentane: ethyl acetate) to provide the desired product (28 mg, 0.076 mmol) in 79% yield. $^1$H (DMSO-d$_6$☐, 600 MHz): δ 8.22 (1H, s), 7.45 (2H, d, J=8.20 Hz), 7.39 (2H, d, J=8.24 Hz), 5.42 (2H, s), 4.60 (1H, m), 4.54 (2H, s), 4.52 (1H, m), 3.71 (1H, m), 3.66 (1H, m), 1.57 (9H, s); $^{13}$157.8, 153.8, 138.6, ☐C (DMSO-d6, 150 MHz): δ 134.6, 127.8, 127.7, 126.2, 115.6, 83.5 (82.4), 71.6, 71.2, 69.1 (69.0), 65.3, 27.4; $^{19}$F (DMSO-d$_6$-221.74 (1F, m). ☐, 564 MHz): δ HRMS calcd for $C_{18}H_{22}ClFN_2O_3$: 369.137575, found 369.1377.

Example 6

Synthesis of 2-tert-butyl-4-chloro-5-[4-(2-fluoro-propoxy)benzyloyl-2H-pyridazin-3-one Example 6A Synthesis of 1-(4-hydroxymethylphenoxy)propan-2-one

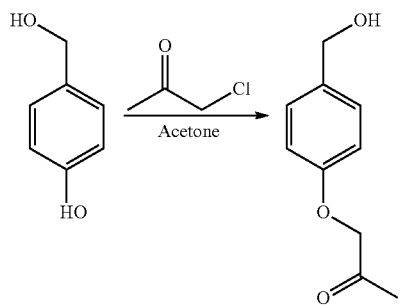

To a stirred solution of 4-hydroxybenzyl alcohol (1.0 g, 8.06 mmol) in acetone (80 mL) was added potassium carbonate (1.34 g, 9.68 mmol) and chloroacetone (0.771 mL, 9.68 mmol). After completion of addition the reaction mixture was heated to reflux. After 20 hours the reaction mixture was cooled down to room temperature and the solvent was removed. Water and ethyl acetate were added to the crude material. The aqueous layer was separated and extracted with ethyl acetate (3×, 100 mL). All combined organic layers were dried over $Na_2SO_4$, filtered, and concentrated to provide an oil. The crude material was purified using silica gel chromatography (gradient from 4:1 to 1:1 pentane:ethyl acetate) to provide the desired product (0.981 g, 5.45 mmol) in 98% yield. $^1$H (CDCl$_3$, 600 MHz): δ 7.30 (2H, d, J=8.7 Hz), 6.87 (2H, d, J=8.7 Hz), 4.63 (2H, d, J=5.7 Hz), 4.54 (2H, s), 2.27 (3H, s), 1.66 (1H, t, J=5.8 Hz); $^{13}$C (CDCl$_3$, 150 MHz): δ 205.7, 157.3, 134.3, 128.8, 114.6, 73.1, 64.8, 26.6.

Example 6B

Synthesis of 1-(4-hydroxymethyl-phenoxy)-propan-2-ol:

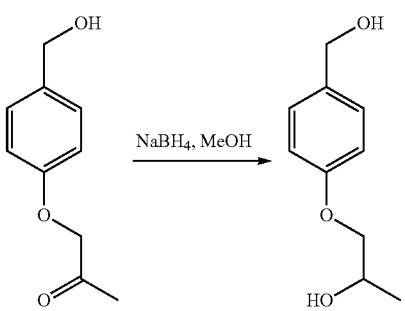

To a solution of 1-(4-hydroxymethylphenoxy)-propan-2-one (1.26 g, 6.99 mmol) dissolved in methanol (60 mL) was added solid NaBH₄ (0.32 g, 8.39 mmol). After completion of addition the reaction mixture was stirred at room temperature overnight. The reaction mixture was diluted with water, and the aqueous layer was extracted with ethyl acetate (3×). All combined organic layers were dried over Na₂SO₄, filtered, and concentrated to provide an oil (1.24 g, 6.81 mmol), which was used in the next step without any further purification (98% yield). ¹H (CDCl₃ 7.29☐, 600 MHz): δ (2H, d, J=8.4 Hz), 6.90 (2H, d, J=8.5 Hz), 4.62 (2H, s), 4.21 (1H, m), 3.94 (1H, dd, J=9.2, 3.1 Hz), 3.82 (1H, m), 1.29 (3H, d, J=6.4 Hz).

Example 6C

Synthesis of 2-tert-butyl-4-chloro-5-[4-(2-hydroxy-propoxy)benzyloxy]-2H-pyridazin-3-one

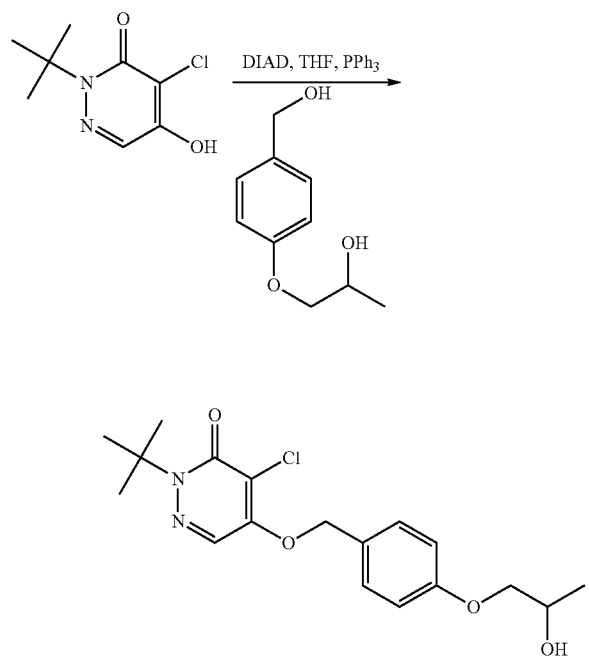

To solution of the product of Example 6B (269 mg, 1.48 mmol) and 2-tert-butyl-4-chloro-5-hydroxy-2H-pyridazin-3-one (250 mg, 1.23 mmol) dissolved in anhydrous THF (18.5 mL) was added solid PPh₃ (485 mg, 1.85 mmol) and DIAD (0.358 mL, 1.85 mmol). After completion of addition the reaction mixture continued to stir at room temperature. After 20 hours, the reaction mixture was diluted with water. The aqueous layer was separated and extracted with ethyl acetate (3×). All combined organic layers were dried over Na₂SO₄, filtered, and concentrated to provide an oil. The crude material was purified using silica gel chromatography (1:1 pentane:ethyl acetate) to provide the desired product (234 mg, 0.634 mmol) in 51% yield. ¹H (CDCl₃ 7.71 (1H, s), 7.33 (2H, d, ☐, 600 MHz): δ J=8.7 Hz), 6.94 (2H, d, J=8.7 Hz), 5.24 (2H, s), 4.19 (1H, m), 3.95 (1H, dd, J=9.2, 3.1 Hz), 3.81 (1H, dd, J=9.2, 7.7 Hz), 1.62 (9H, s) 1.29 (3H, d, J=6.4 Hz).

Example 6D

Synthesis of toluene-4-sulfonic acid 2-[4-(1-tert-butyl-5-chloro-6-oxo-1,6-dihydro-pyridazin-4-yloxymethyl)-phenoxy]-1-methyl-ethyl ester

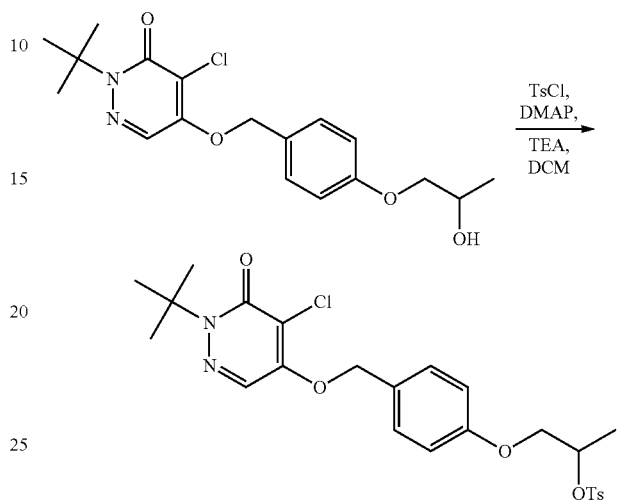

To a solution of the product of Example 6C (200 mg, 0.546 mmol) dissolved in anhydrous dichloromethane (6.0 mL) was added TsCl (125 mg, 0.656 mmol), DMAP (100 mg, 0.819 mmol) and triethylamine (0.0914 mL, 0.656 mmol). The reaction mixture continued stirring at room temperature. After 22 hours the reaction mixture was diluted with water. The aqueous layer was separated and extracted with ethyl acetate (3×). All combined organic layers were dried over Na₂SO₄, filtered, and concentrated to provide an oil. The crude material was purified using silica gel chromatography (70:30 pentane:ethyl acetate) to provide the desired product (166 mg, 0.319 mmol) in 58% yield. ¹H (CDCl₃ 7.80 (2H, d, ☐, 600 MHz): δ J=8.3 Hz), 7.72 (1H, s), 7.32 (2H, d, J=7.9 Hz), 7.29 (2H, d, J=8.7 Hz), 6.74 (2H, d, J=8.7 Hz), 5.22 (2H, s), 4.19 (1H, m), 4.02 (1H, dd, J=10.4, 6.0 Hz), 3.93 (1H, dd, J=10.4, 4.5 Hz), 2.44 (3H, s), 1.63 (9H, s) 1.42 (3H, d, J=6.5 Hz); ¹³C (CDCl₃ 158.9,☐, 150 MHz): δ 158.3, 153.6, 144.6, 133.8, 129.6, 128.8, 127.8, 127.4, 125.1, 118.0, 114.7, 76.8, 71.5, 69.7, 66.2, 27.7, 21.5, 17.6.; HRMS calcd for C₂₅H₂₉ClN₂O₆S: 521.150762, found 521.1505.

Example 6E

Synthesis of 2-tert-butyl-4-chloro-5-[4-(2-fluoro-propoxy)benzyloy]-2H-pyridazin-3-one

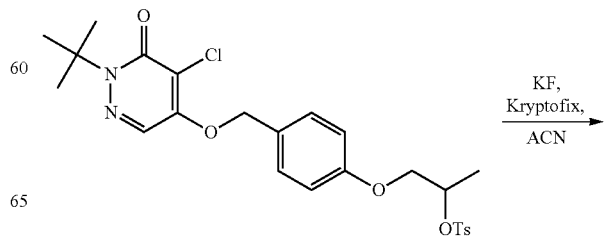

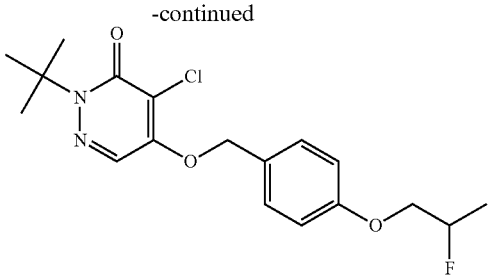

To a solution of the product of Example 6E (50 mg, 0.096 mmol) in anhydrous acetonitrile (1.0 mL) was added KF (11.2 mg, 0.192 mmol) and Kryptofix (72.4 mg, 0.192 mmol). After completion of addition the reaction mixture was heated to 90° C. After 40 minutes, the reaction mixture was cooled down to room temperature and diluted with water. The aqueous layer was separated and extracted with ethyl acetate (3×). All combined organic layers were dried over $Na_2SO_4$, filtered, and concentrated to provide an oil. The crude material was purified using a preparative silica gel thin layer chromatography plate (4:1 pentane:ethyl acetate) to isolate the desired product (12.5 mg, 0.034 mmol) in 41% yield (based on recovered starting material), in addition to unreacted starting material (5.8 mg, 0.011 mmol). $^1H$ ($CDCl_3\square$, 600 MHz): δ 7.73 (1H, s) 7.34 (2H, d, J=8.6 Hz), 6.95 (2H, d, J=8.6 Hz), 5.25 (2H, s), 5.06-4.96 (1H, m), 4.06 (2H, m), 1.63 (9H, s) 1.47 (3H, dd, J=6.4, 23.6 Hz); $^{13}C$ (DMSO-$d_6$, 158.4, 157.8, 153.9, 129.8, 127.6, 126.2, 115.5, 114.6, 89.0$\square$ 150 MHz): δ (88.0), 71.2, 70.4 (70.3), 65.3, 27.4, 16.9 (16.8); $^{19}F$ (DMSO-$d_6$, −178.20 (1F, m);$\square$564 MHz): δ HRMS calcd for $C_{18}H_{22}ClFN_2O_3$: 369.137575, found 369.1370.

Example 7

Synthesis of 2-tert-butyl-4-chloro-5-[4-(3-fluorobutyl)benzyloxy]-2H-pyridazin-3-one Example 7A Synthesis of 4-(3-oxobutyl)benzoic acid methyl ester

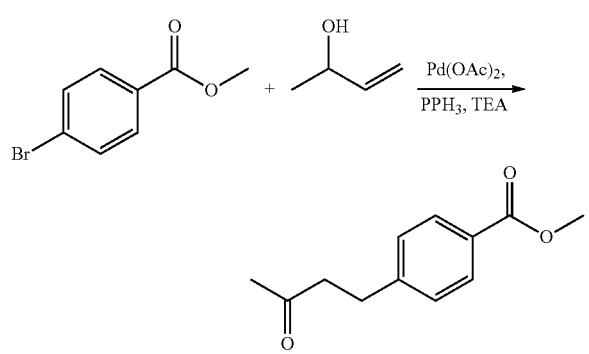

To a solution of methyl-4-bromobenzoate (1.0 g, 4.65 mmol) in triethylamine (13 mL) was added 3-buten-2-ol (1 mL, 11.63 mmol), palladium (II) acetate (0.104 g, 0.465 mmol), and then triphenylphosphine (0.244 g, 0.93 mmol). The reaction was stirred in a 75° C. oil bath overnight under nitrogen atmosphere. Monitoring by TLC (3:1 hexane:ethyl acetate) showed the product and aryl bromide. The reaction was cooled to room temperature and then concentrated. Water was then added followed by extraction with ethyl acetate. The organic layer was washed with water and brine, dried over $Na_2SO_4$, filtered and concentrated. The crude product was purified by flash column chromatography (5:1 to 3:1 hexane:ethyl acetate) to obtain the product (250 mg, 26% yield). $^1H$ NMR (600 MHz, $CDCl_3$): δ 7.95 (d, 2H, J=8.4 Hz), 7.25 (d, 2H, J=8.4 Hz), 3.90 (s, 3H), 2.95 (t, 2H, J=7.45 Hz), 2.77 (t, 2H, J=7.68 Hz), 2.14 (s, 3H).

Example 7B

Synthesis of 2-tert-butyl-4-chloro-5-[4-(3-hydroxybutyl)benzyloxy]-2H-pyridazin-3-one

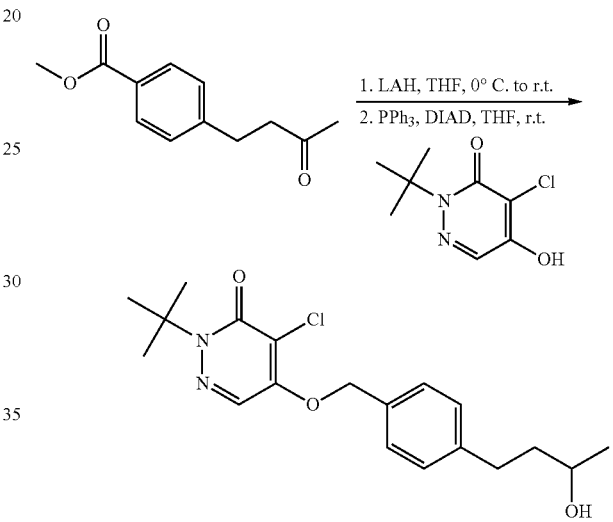

To a solution of the product of Example 7A (505 mg, 2.447 mmol) in THF (19 mL) at 0° C. was added a 1M solution (in THF) of lithium aluminum hydride (12.2 mL, 12.237 mmol) dropwise. After completion of addition the ice bath was removed and the reaction was stirred at room temperature for 1 hour under nitrogen atmosphere. Then, in succession, was added water (183 μL), 15% NaOH solution (183 μL), and water (548 μL). The reaction stirred for an additional 15 minutes before it was filtered and washed with THF. The filtrate was then concentrated under reduced pressure to obtain 4-(4-hydroxymethyl-phenyl)butan-2-ol as a brown oil (314 mg, 71% yield). Then to a solution of 2-tert-butyl-4-chloro-5-hydroxy-2H-pyridazin-3-one (234 mg, 1.155 mmol) in THF (45 mL) was added 4-(4-hydroxymethylphenyl)butan-2-ol (312 mg, 1.732 mmol), triphenylphosphine (454 mg, 1.732 mmol), and then diisopropyl azodicarboxylate (DIAD, 335 μL, 1.732 mmol). The reaction was stirred at room temperature overnight under nitrogen atmosphere. Thin layer chromatography (100% ethyl acetate) indicated consumption of the pyridazinone starting material and the reaction was concentrated. The crude material was purified by flash column chromatography (4:1 hexane:ethyl acetate to 100% ethyl acetate) to obtain a clear oil (200 mg, 48% yield). $^1H$ NMR (600 MHz, $CDCl_3$): δ 7.73 (s, 1H), 7.32 (d, 2H, J=8.0), 7.24 (d, 2H, J=8.0), 5.30 (s, 1H), 5.27 (s, 2H), 3.83 (m, 1H), 2.80-2.76 (m, 1H), 2.71-2.66 (m, 1H), 1.63 (s, 9H), 1.23 (d, 3H, J=6.2); $^{13}C$ (CDCl₃ 159.3, 153.9, 143.2, 132.5, 129.2, 127.6, 125.4, ☐, 150 MHz): δ HRMS calcd for C☐118.5, 73.4, 67.6, 66.6, 40.9, 32.0, 28.1, 23.9.₁₉H₂₅ClN₂O₃: 365.162647, found 365.1624.

Example 7C

Synthesis of toluene-4-sulfonic acid 3-[4-(1-tert-butyl-5-chloro-6-oxo-1,6-dihydro-pyridazin-4-yloxymethyl)-phenyl]-1-methylpropyl ester

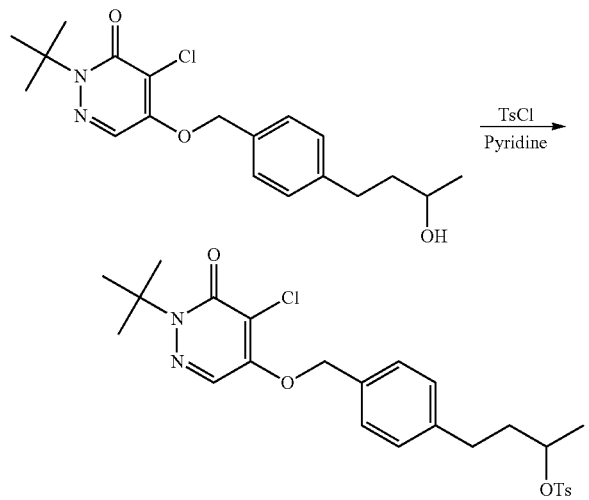

To a solution of the product of Example 7B (200 mg, 0.548 mmol) in pyridine (10 mL) was added p-toluenesulfonyl chloride (209 mg, 1.096 mmol). The reaction was stirred at room temperature overnight under nitrogen atmosphere. Monitoring by LC-MS showed a 1:1 mixture of starting material and product. The reaction was diluted with ethyl acetate and washed with 5% CuSO₄ until a light blue aqueous solution was maintained. The organic layer was then dried over Na₂SO₄, filtered, and concentrated. The crude material was purified by flash column chromatography (3:1 hexane:ethyl acetate to 100% ethyl acetate) to recover the starting material (90 mg) and the product as a clear oil (74 mg, 47% yield based on recovered starting material). ¹H NMR (600 MHz, CDCl₃): 7.80 (d, 2H, J=8.3 Hz), 7.72 (s, 1H), 7.33 (d, 2H, J=8.0 Hz), 7.30 (d, 2H, J=8.1 Hz), 7.13 (d, 2H, J=8.1 Hz), 5.27 (s, 2H), 4.66 (m, 1H), 2.65 (m, 1H), 2.54 (m, 1H), 2.45 (s, 3H), 1.94 (m, 1H), 1.81 (m, 1H), 1.63 (s, 9H), 1.26 (s, 3H).

Example 7D

Synthesis of 2-tert-butyl-4-chloro-5-[4-(3-fluorobutyl)benzyloxy]-2H-pyridazin-3-one

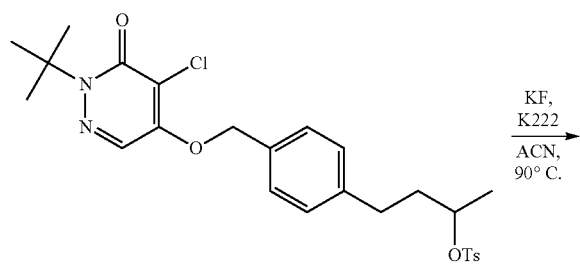

-continued

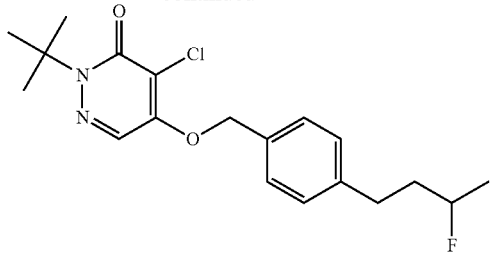

To a solution of the product of Example 7C (18.2 mg, 0.035 mmol) in acetonitrile (400 µL) was added potassium fluoride (4.1 mg, 0.070 mmol) and K222 (26.4 mg, 0.070 mmol). The reaction was stirred at 90° C. for 20 minutes under nitrogen atmosphere, monitoring by LC-MS. The reaction was then cooled to room temperature and concentrated under reduced pressure. The crude material was purified by preparative thin layer chromatography (4:1 hexane:ethyl acetate as eluant) to obtain the product as an oil (5 mg, 39% yield). ¹H NMR (600 MHz, CDCl₃): δ 7.70 (s, 1H), 7.34 (d, 2H, J=7.9 Hz), 7.24 (d, 2H, J=8.0 Hz), 5.28 (s, 2H), 4.71-4.60 (m, 2H), 2.84-2.80 (m, 1H), 2.73-2.69 (m, 1H), 2.02-1.93 (m, 1H), 1.87-1.77 (m, 1H), 1.63 (s, 9H), 1.35 (dd, 3H, J=6.2 and 23.9 Hz); ¹³C (CDCl₃159.1, 153.8, ☐, 150 MHz): δ 142.4, 132.5, 129.0, 127.4, 125.2, 118.3, 90.4 (89.3), 71.9, 66.3, 38.5 (38.4), 31.1 (31.0), 27.9, 21.1 (21.0);¹⁹F (CDCl₃— 174.7☐, 564 MHz): δ (1F, m); HRMS calcd for C₁₉H₂₃ClFN₂O₂: 367.158310, found 367.1582.

Example 8

Synthesis of toluene-4-sulfonic acid 2-[4-(1-tert-butyl-5-chloro-6-oxo-1,6-dihydro-pyridazin-4-yloxymethyl)-benzyloxy]ethyl ester hexadeuterate

Example 8A

Synthesis of 4-[2-hydroxyethoxymethyl]benzoic acid methyl ester tetradeuterate

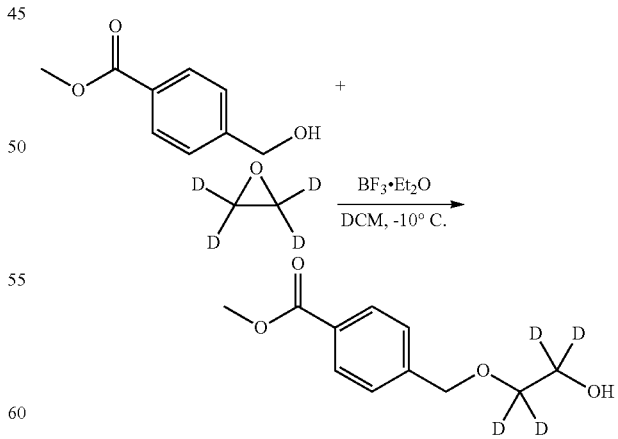

To a flame-dried 2-neck flask was added a solution of methyl-4-(hydroxymethyl)benzoate (2.5 g, 15 mmol) in dichloromethane (30 mL). The reaction was purged with nitrogen and brought to −5° C. A dewar condenser (also flame-dried) containing a dry ice/acetone bath (−78° C.) was affixed to the flask and ethylene oxide-tetradeuterate was added (~55 drops). Then BF₃Et₂O (510 µL, 0.0041 mmol) was added dropwise and the reaction stirred at −5° C. for 35 minutes under nitrogen atmosphere. Monitoring by TLC (100% ethyl acetate) showed complete consumption of the starting material. The reaction was warmed to room temperature and vented to remove any excess ethylene oxide gas. The reaction was then diluted with brine and extracted with dichloromethane (2 times). The combined organics were dried over Na₂SO₄, filtered, and concentrated under reduced pressure to obtain a crude oil. Purification by flash column chromatography (4:1 pentane:ethyl acetate) provided the product as a clear oil (520 mg, 16% yield). ¹H NMR (600 MHz, CDCl₃) δ 8.02 (d, 2H, J=8.2 Hz), 7.41 (d, 2H, J=8.1 Hz), 4.62 (s, 2H), 3.92 (s, 3H); ¹³C NMR (150 MHz, CDCl₃167.1, 143.5, 130.8, ▢) δ 129.9, 127.5, 72.8, 52.4.

Example 8B

Synthesis of 4-[2-(tert-butyldimethylsilanyloxy) ethoxymethyl]benzoic acid methyl ester tetradeuterate

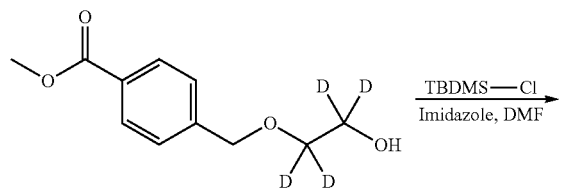

To a solution of the product of Example 8A (500 mg, 2.334 mmol) in DMF (23 mL) was added tert-butyldimethylsilyl chloride (528 mg, 3.501 mmol) and imidazole (238 mg, 3.501). The reaction was stirred at room temperature for 5 hours under nitrogen atmosphere, monitoring by TLC (3:1 pentane:ethyl acetate). Another 0.5 eq. portion of tert-butyldimethylsilyl chloride (176 mg) and imidazole (79 mg) were added and the resultant mixture stirred at room temperature overnight. The majority of the starting material was consumed in 16 hours, as indicated by thin layer chromatography. The reaction was diluted with water and extracted with ethyl acetate (2 times). The combined organic layers were dried over Na₂SO₄, filtered, and concentrated under reduced pressure to obtain a crude oil which was purified by passage through thick pad of silica gel (3:1 pentane:ethyl acetate) to obtain the product as a clear oil (602 mg). ¹H NMR (600 MHz, CDCl₃): 8.00 (d, 2H, J=8.3 Hz), 7.40 (d, 2H, J=8.5 Hz), 4.62 (s, 2H), 3.90 (s, 3H), 0.90 (s, 9H), 0.06 (s, 6H).

Example 8C

Synthesis of {4-[2-(tert-butyldimethylsilanyloxy) ethoxymethyl]phenyl}methanol hexadeuterate

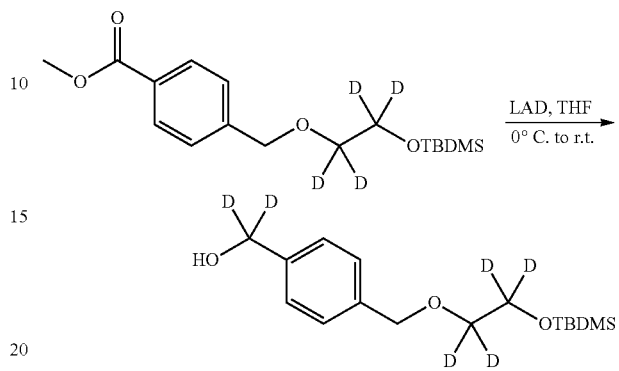

To a solution of the product of Example 8B (610 mg, 1.857 mmol) in THF (19 mL) at 0° C. was added a 1M solution (in THF) of lithium aluminum deuteride (1.9 mL, 1.857 mmol) dropwise. After completion of addition the ice bath was removed and the reaction was stirred at room temperature for 3.5 hours under nitrogen atmosphere, monitoring by TLC (3:1 pentane:ethyl acetate). The reaction was then diluted with water and extracted with ethyl acetate (2 times). The combined organics were dried over Na₂SO₄, filtered, and concentrated under reduced pressure to obtain a clear oil (482 mg, 86% yield). The material was taken to the next step without further purification. ¹H NMR (600 MHz, CDCl₃): 7.33 (s, 4H), 4.56 (s, 2H), 0.89 (s, 9H), 0.06 (s, 6H).

Example 8D

Synthesis of 2-tert-butyl-4-chloro-5-{4-[2-(tert-butyldimethylsilanyloxy)ethoxymethyl]benzyloxy}-2H-pyridazin-3-one hexadeuterate

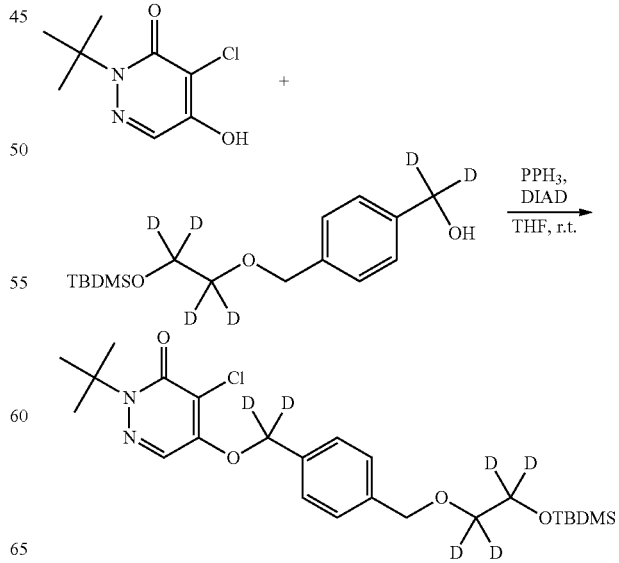

To a solution of 2-tert-butyl-4-chloro-5-hydroxy-2H-pyridazin-3-one (212 mg, 1.047 mmol) in THF (15 mL) was added the product of Example 8C (475 mg, 1.570 mmol), triphenylphosphine (412 mg, 1.570 mmol), and then diisopropyl azodicarboxylate (DIAD, 304 µL, 1.570 mmol). The reaction was stirred at room temperature for 2 hours under nitrogen atmosphere. Thin layer chromatography (1:1 hexane:ethyl acetate) indicated consumption of the pyridazinone starting material and the reaction was concentrated in vacuo. The crude material was purified by flash column chromatography (90:10 pentane:ethyl acetate) to obtain a clear oil (336 mg, 66% yield). $^1$H NMR (600 MHz, CDCl$_3$): 7.70 (s, 1H), 7.39 (m, 4H), 4.58 (s, 2H), 1.63 (s, 9H), 0.90 (s, 9H), 0.07 (s, 6H); HRMS calcd for $C_{24}H_{31}D_6ClN_2O_4Si$: 509.24738, found 509.2480.

Example 8E

Synthesis of 2-tert-butyl-4-chloro-5-[4-(2-hydroxyethoxymethyl)benzyloxy]-2H-pyridazin-3-one hexadeuterate

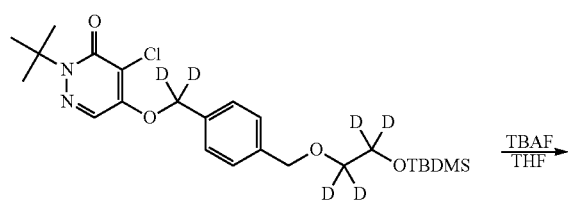

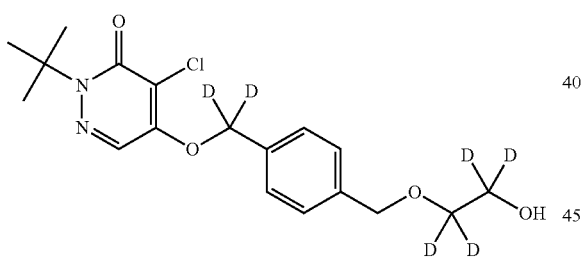

To a solution of the product of Example 8D (330 mg, 0.677 mmol) in THF (7 mL) was added a 1M solution (in THF) of tetrabutylammonium fluoride (1 mL, 1.016 mmol) dropwise. The reaction was stirred at room temperature for 2 hours under nitrogen atmosphere, monitoring by TLC (1:1 hexane:ethyl acetate). The reaction was then concentrated under reduced pressure and passed through a thick pad of silica (100% ethyl acetate) to obtain the product as an oil containing a minor percentage of the corresponding silanol. The material was taken to the next step without further purification. $^1$H NMR (600 MHz, CDCl$_3$): 7.72 (s, 1H), 7.41 (s, 4H), 4.59 (s, 2H), 1.64 (s, 9H); $^{13}$C NMR (150 MHz, rt, CDCl$_3$):159.2, 153.9, 139.5, 134.5, 128.5, 127.5, 125.3, 118.6, 73.0, 66.6, 28.1; HRMS calcd for $C_{25}H_{23}D_6ClN_2O_6S$: 549.169754, found 549.1705.

Example 8F

Synthesis of toluene-4-sulfonic acid 2-[4-(1-tert-butyl-5-chloro-6-oxo-1,6-dihydro-pyridazin-4-yloxymethyl)-benzyloxy]ethyl ester hexadeuterate

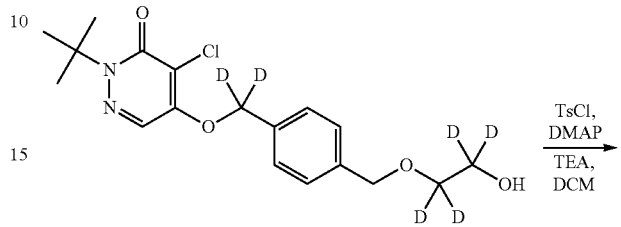

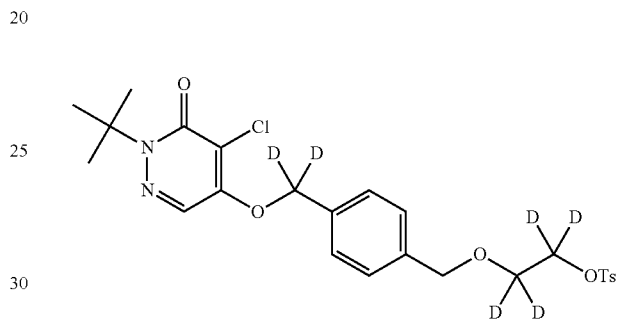

To a solution of the product of Example 8E (250 mg, 0.670 mmol) in dichloromethane (7 mL) was added p-toluenesulfonyl chloride (153 mg, 0.805 mmol), N,N-dimethylaminopyridine (DMAP, 98 mg, 0.805 mmol), and triethylamine (140 µL, 1.005 mmol). The reaction was stirred at room temperature overnight under nitrogen atmosphere. Thin layer chromatography (1:1 hexane:ethyl acetate) indicated almost complete consumption of the alcohol. The reaction was concentrated under reduced pressure and the crude material was purified by flash chromatography (2:1 hexane:ethyl acetate to 1:1 hexane:ethyl acetate to 100% ethyl acetate) to recover the starting material (9 mg) and the product (261 mg, 77% yield based on recovered starting material) as a clear oil. $^1$H NMR (600 MHz, CDCl$_3$): 7.76 (d, 2H, J=8.3 Hz), 7.73 (s, 1H), 7.36 (d, 2H, J=8.1 Hz), 7.29 (m, 4H), 4.47 (s, 2H), 2.40 (s, 3H), 1.61 (s, 9H); $^{13}$C NMR (150 MHz, rt, CDCl$_3$): 159.0, 153.8, 145.0, 138.5, 134.4, 133.1, 129.9, 128.1, 128.0, 127.3, 125.2, 118.1, 72.7, 71.0, 37.0, 63.4, 28.0, 21.7.

Example 8G

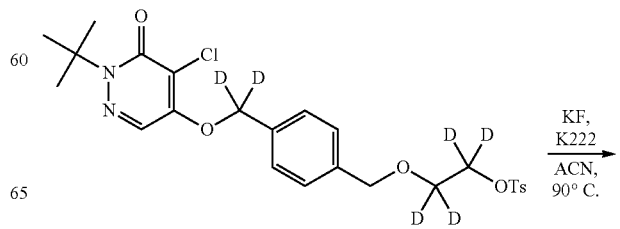

-continued

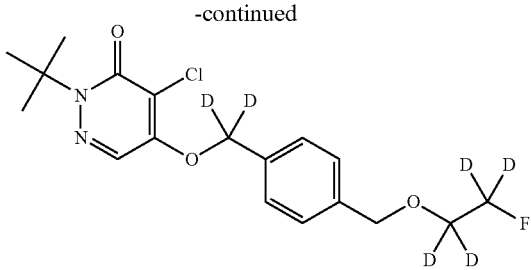

To a solution of the product of Example 8F (14 mg, 0.027 mmol) in acetonitrile (300 μL) was added potassium fluoride (3.1 mg, 0.053 mmol) and K222 (20 mg, 0.053 mmol). The reaction was stirred at 90° C. for 10 minutes under nitrogen atmosphere, monitoring by TLC (1:1 hexane:ethyl acetate). The reaction was then cooled to room temperature and concentrated under reduced pressure. The crude material was purified by preparative TLC (2:1 hexane:ethyl acetate) to obtain the product as an oil (6.2 mg, 62% yield). $^1$H NMR (600 MHz, CDCl$_3$): 7.70 (s, 1H), 7.40 (s, 4H), 4.61 (s, 2H), 1.63 (s, 9H); $^{13}$C NMR (150 MHz, rt, CDCl$_3$): 158.5, 153.1, 138.2, 133.8, 127.7, 126.8, 124.6, 117.8, 72.4, 65.9, 27.3; $^{19}$F NMR (564 MHz, CDCl$_3$): −225.2 (m, 1F).

Example 9

General Radiosynthetic and Purification Procedures for Preparation of Fenazaquin and Pyridaben Complexes Radiolabeled with the Fluorine-18 Radionuclide The Fluorine-18 ($^{18}$F) used in these Examples was produced via the proton bombardment of enriched Oxygen-18 ($^{18}$O) as H$_2$$^{18}$O with approximately 10 MeV protons by PETnet (Woburn, Mass.). The expression for this nuclear reaction is: O$^{18}$(p, γ)$^{18}$F.

For all of the radiosynthetic reactions, a similar procedure was used. All glassware was silanized to preclude adhesion of the material to the vessel walls and to optimize transfers. A dedicated, specific HPLC unit was used for purification for all compounds. A dedicated specific HPLC unit was used for radioanalytical analyses of final product.

The $^{18}$F typically was received from the supplier deposited on a processed column ($^{18}$F column) encased in lead shielding. The $^{18}$F column contained the sodium salt coordinated to either alumina or a quaternary ammonium salt housed in a glass column. The column ends are connected to Tygon™ tubing with male and female Luer™ lock fittings. The $^{18}$F was removed from the column using the following method.

1. A solution of 15 mg of potassium carbonate (K$_2$CO$_3$) in 1 mL of distilled/deionized water (H$_2$O) and a solution of 90 mg of 4,7,13,16,21,24-hexaoxa-1,10-diazabicyclo[8.8.8]hexacosane (Kryptofix™; K222) dissolved in 4 mL of anhydrous acetonitrile (CH$_3$CN) were combined and gently stirred, ensuring the layers did not separate, forming the column eluting solution (CES).
2. A one mL aliquot of the CES was extracted from the vial described in step three using a 3 mL syringe and the syringe was attached to the male Luer™ lock of the Tygon™ tubing connected to the $^{18}$F column.
3. A narrow gauge needle was attached to the female Luer™ lock of the other Tygon™ tubing connected to the $^{18}$F column, and the needle was inserted through the rubber septum fitted to a 15 mL 24/40 Pyrex™ pear-shaped glass flask.
4. The 15 mL pear shaped flask was vented with a needle and the flask was flushed with dry nitrogen. The flushing needle was connected to a vacuum line and the flow adjusted such that CES was slowly drawn through the $^{18}$F column into the 15 mL pear-shaped flask.
5. The vacuum and N$_2$ gas flow were adjusted such that the contents of the flask were reduced to dryness. Anhydrous CH$_3$CN (1 mL) was added via syringe to the flask, using vacuum to drive the transfer. The vacuum and N$_2$ gas flow were balanced to remove the acetonitrile. This procedure was repeated twice, after which point the vacuum was removed.
6. The contents of the flask were removed via syringe and the radioactivity was quantified. The $^{18}$F solution was used directly in radiolabeling syntheses.

The next steps describe the radiolabeling of the fenazaquin and pyridaben analogs with $^{18}$F. As noted above, these steps were repeated for each of the compounds. The following reaction scheme, while specifically illustrating the synthesis of a pyridaben analog, depicts a representative synthesis for all of the $^{18}$F-fenazaquin and pyridaben analogs:

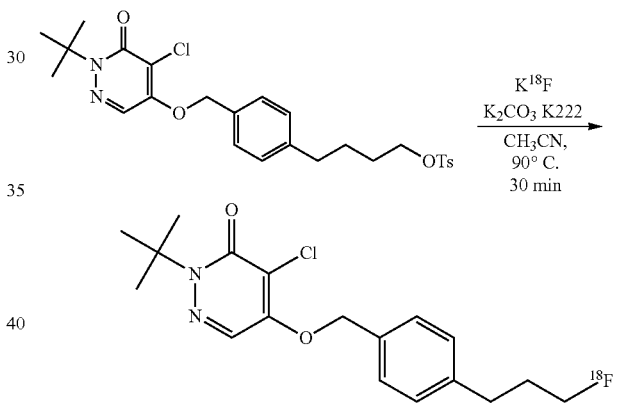

7. The toluenesulfonate ester precursor to the desired fenazaquin or pyridaben analog (2.5 mg) was dissolved in CH$_3$CN (0.5 mL) in a conical silanized 5 mL Wheaton™ glass vial with a magnetic stirring bar. The vial was immersed in a oil bath heated at 90° C. The solution of the $^{18}$F described above was added to the reaction vial the resultant mixture was heated at 90° C. for 30 minutes.
8. The contents were transferred to a 50 mL silanized round bottom flask containing distilled/deionized water (25 mL), and the contents of the flask are removed via syringe, and deposited on a Waters™ Oasis HLB (hydrophilic-lipophilic balance) column, allowing unreacted fluoride and undesired salts to pass through with the eluate.
9. The organic components were eluted from the column into a conical 5 mL vial using dichloromethane, (3 mL, CH$_2$Cl$_2$). The eluant was purified via preparative HPLC (Phenomenex LUNA C-18 column 250×10 mm, 5 u particle, 100 A pore, gradient elution 90/10 H$_2$O/CH$_3$CN—CH$_3$CN). The appropriate fractions were concentrated and analyzed for radiochemical yield and radiochemical purity (analytical HPLC). The solution was concentrated to dryness in vacuo, and dissolved in the appropriate volume of 10% ethanolic saline for injection and/or biological studies.

Example 10

Synthesis of 2-tert-butyl-4-chloro-5-(4-(4-[$^{18}$F]-fluorobutyl)benzyl)-thio-3(2H)-pyridazinone

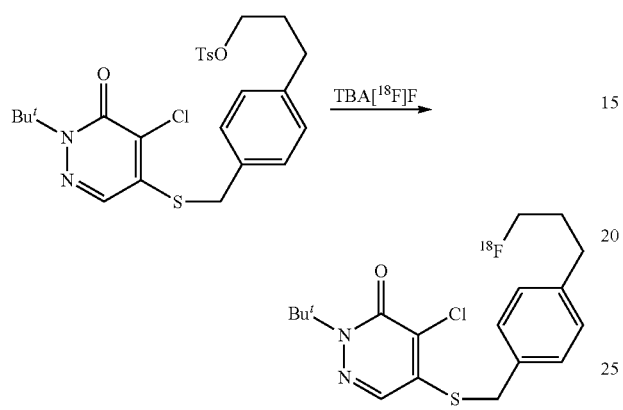

Aqueous $^{18}$F (16 mCi, 0.1 ml) was added to a vacutainer containing 50 of tetrabutylammonium hydroxide (40% wt sol. in water). The mixture was concentrated under nitrogen in an oil bath. Acetonitrile (250 µl) was added and the mixture was concentrated under nitrogen. 100 µl of THF was then added to the mixture followed by 5 mg of 2-tert-butyl-4-chloro-5-(4-(4-toluenesulfonyloxy-butyl)benzyl)thio-3 (2H)-pyridazinone. The mixture was then heated in an oil bath at 70° C. for 30 minutes. The resulting mixture was then diluted with water, and applied to a C18 Sep-Pak, eluting with acetonitrile to obtain the title compound.

Example 11

Synthesis of 2-tert-butyl-4-chloro-5-(2-[$^{18}$F]-fluoro-1-(4-tert-butylphenyl)-1-ethyl)oxy-3(2H)-pyridazinone Example 11A Synthesis of (4-tert-butylphenyl) ethane 1,2 diol

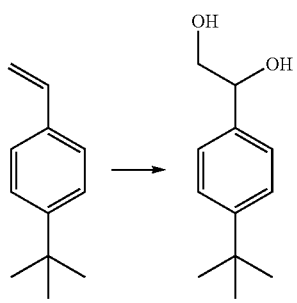

To a 100 ml round bottom flask is added 20 ml tert butanol, 20 ml of water and 5.6 g of AD-mix-β. The solution is stirred and cooled to 0 C. tert-butyl styrene (0.64 g, 4 mmol) is added to the mixture and the resulting solution is stirred overnight at 0 C. Solid sodium sulfite (6 g) is added and the mixture stirred for an additional 30 minutes. The solution is then extracted in ethyl acetate, washed with water and dried. The crude is then purified by flash chromatography (silica gel; ethyl acetate/hexanes) to afford the product.

Example 11B

Synthesis of 1-tert-butyldimethylsilyloxy-2-hydroxy-2-(4-tertbutylphenyl) ethane (4-tert-butylphenyl) ethane 1,2 diol (0.5 g, 2.57 mmol) is dissolved in DMF in a

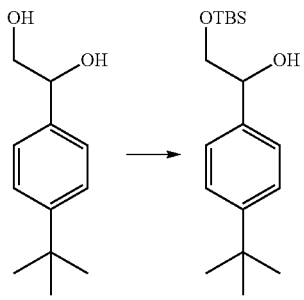 [SMILES: CC(C)(C)c1ccc(C(O)CO)cc1 ; CC(C)(C)c1ccc(C(O)CO[Si](C)(C)C(C)(C)C)cc1]

25 ml round bottom flask and to this were added imidazole (0.210 g, 3.09 mmol) and tert-butyldimethylsilyl chloride (0.46 g, 3.09 mmol). The mixture is stirred for 6 hours after which it is extracted in dichloromethane and the organic layer washed with water and dried. Purification by flash chromatography (silica gel; ethyl acetate/hexanes) affords the above mentioned product.

Example 11C

Synthesis of 2-tert-butyl-4-chloro-5-(2-tert-butyldimethylsilyloxy-1-(4-tert-butylphenyl)-1-ethyl) oxy-3(2H)-pyridazinone

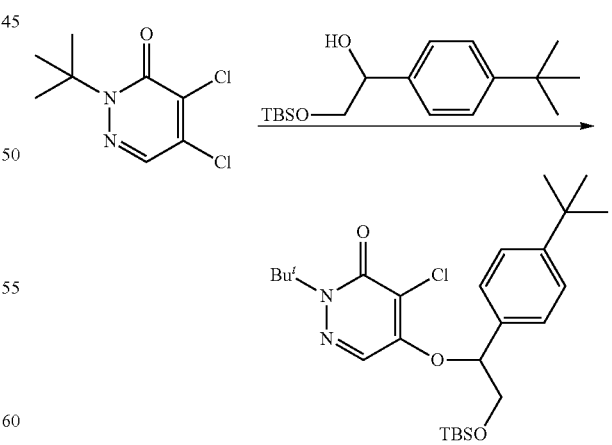

To a solution of 2-tert-butyl-4,5-dichloro-3(2H)-pyridazinone (0.5 g, 2.27 mmol) in DMF (10 ml) were added anhydrous cesium carbonate (0.74 g, 2.27 mmol) and 1-tert-butyldimethylsilyloxy 2-hydroxy 2-(4-tertbutylphenyl) ethane (0.7 g, 2.27 mmol). The mixture is stirred for 2 hours at 70° C. and then cooled to room temperature and ethyl acetate is added to it. The solution is then washed with water, dried and concentrated and the residue subjected to purification by flash chromatography (silica gel; ethyl acetate/hexanes) to give the above compound.

Example 11D

Synthesis of 2-tert-butyl-4-chloro-5-(2-hydroxy-1-(4-tert-butylphenyl)-1-ethyl)oxy-3(2H)-pyridazinone

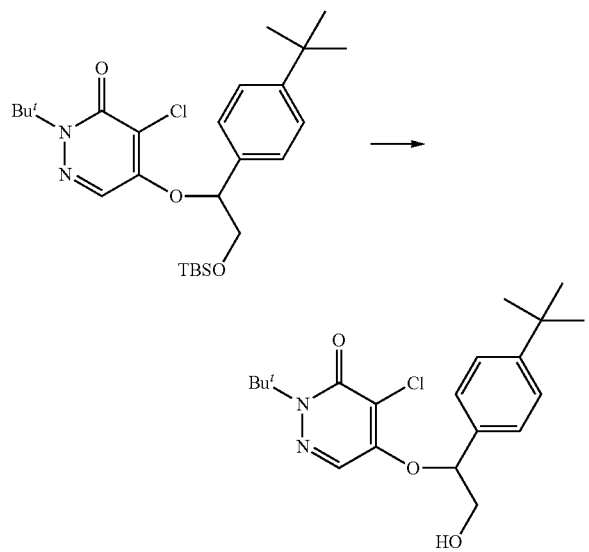

A 25 ml round bottom flask is charged 2-tert-butyl-4-chloro-5-(2-tert-butyldimethylsilyloxy-1-(4-tert-butylphenyl)-1-ethyl)oxy-3(2H)-pyridazinone (0.5 g, 1.01 mmol) and to it is added 5 ml of 1% concd. HCl in ethanol. The solution is stirred for one hour after which it is poured in water and extracted with ethyl acetate. The ethyl acetate is removed using the rotary evaporator and subjected to flash chromatography using silica gel and ethyl acetate/hexanes mixture as the eluting medium.

Example 11E

Synthesis of 2-tert-butyl-4-chloro-5-(2-p-toluenesulfonyloxy-1-(4-tert-butylphenyl)-1-ethyl)oxy-3(2H)-pyridazinone

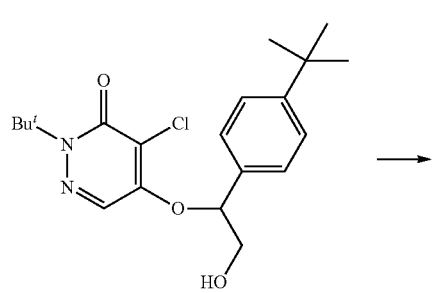

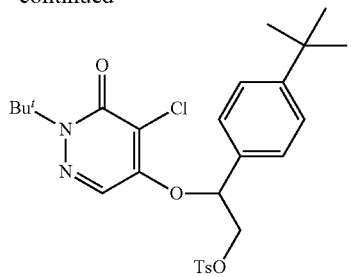

To a 15 ml round bottom flask charged with 2-tert-butyl-4-chloro-5-(2-hydroxy-1-(4-tert-butylphenyl)-1-ethyl)oxy-3(2H)-pyridazinone (0.25 g, 0.66 mmol) is added pyridine. Toluenesulfonyl chloride (0.15 g, 0.79 mmol) is then added to it and the mixture stirred for 4 hours. The reaction mixture is diluted with ethyl acetate, washed with 5% copper sulfate solution and then with water and dried. After removing the solvent on the rotary evaporator the crude is purified by flash chromatography using ethyl acetate-hexanes as the eluting mixture.

Example 11F

Synthesis of 2-tert-butyl-4-chloro-5-(2-fluoro-1-(4-tert-butylphenyl)-1-ethyl)oxy-3(2H)-pyridazinone

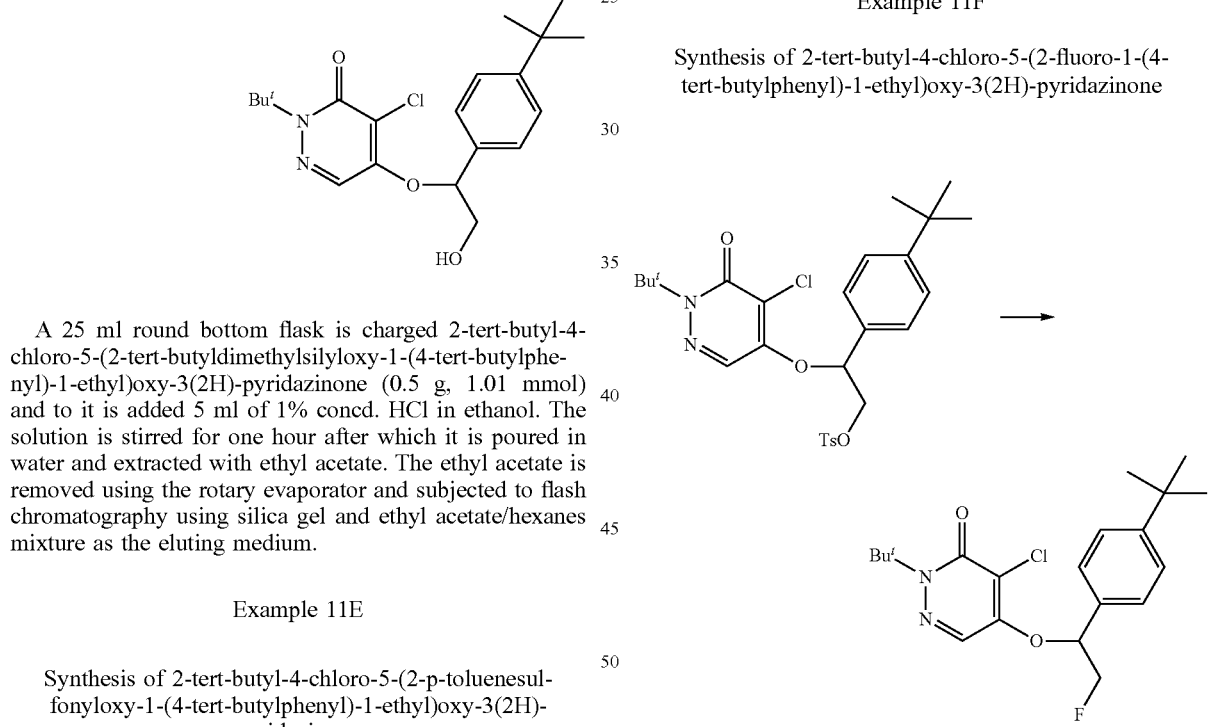

To a 15 ml round bottom flask charged with 2-tert-butyl-4-chloro-5-(2-p-toluenesulfonyloxy-1-(4-tert-butylphenyl)-1-ethyl)oxy-3(2H)-pyridazinone (0.2 g, 0.375 mmol) is added 3.75 ml of tetrabutylammonium fluoride solution (1M in THF, 3.75 mmol). The mixture is first stirred at room temperature for 15 minutes after which it is heated for 15 minutes at 100° C. The solution is then cooled to room temperature and to it is added dichloromethane followed by water. The layers were separated and the organic layer is washed with water and then dried. The organic layer is then concentrated and subjected to purification using silica gel flash chromatography (ethyl acetate/hexanes) to obtain the above compound.

Example 11G

Synthesis of 2-tert-butyl-4-chloro-5-(2-[$^{18}$F]-fluoro-1-(4-tert-butylphenyl)-1-ethyl)oxy-3(2H)-pyridazinone

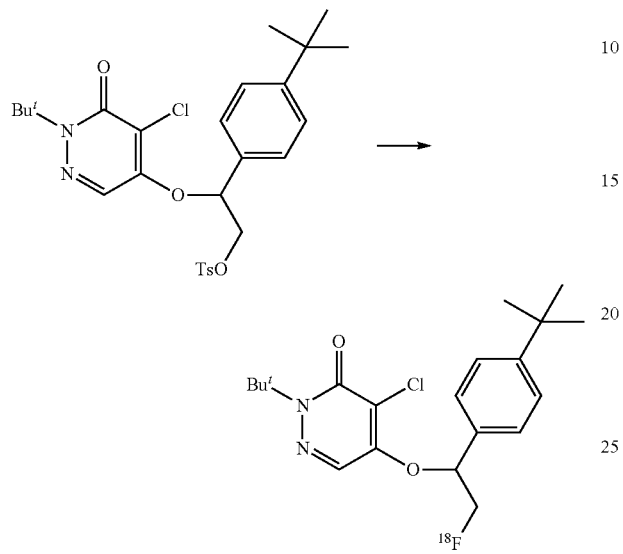

Aqueous $^{18}$F (16 mCi, 0.1 ml) is added to a vacutainer containing 5 μl of tetrabutylammonium hydroxide (40% wt sol. in water). The mixture is concentrated under nitrogen in an oil bath and 250 μl of acetonitrile is added and this too is concentrated under nitrogen. 100 μl of THF is then added to it followed by 5 mg of 2-tert-butyl-4-chloro-5-(2-p-toluenesulfonyloxy-1-(4-tert-butylphenyl)-1-ethyl)oxy-3(2H)-pyridazinone. The mixture is then heated in an oil bath at 70° C. for 30 minutes. This is then diluted with water, applied to a C18 Sep-Pak and eluted with acetonitrile to get the above mentioned compound.

Example 12

Synthesis of Fenazaquin Analogs

Example 12A

Synthesis of 4-Chloro quinazoline

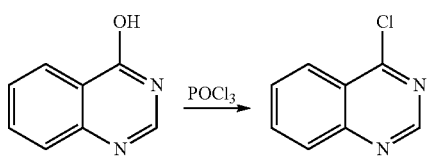

4-Quinazolone (5 g, 34.2 mmol), phosphorus pentachloride (10.26 g, 47.9 mmol) and phosphorus oxychloride (40 ml) were refluxed for two hours at 115-118 C. The phosphorus oxychloride was removed in vacuo and the residue was extracted in ether. The entire mixture was then poured into a vessel containing crushed ice and again extracted with ether. The ether layer was then washed with sodium bicarbonate and dried. The ether was then removed under reduced pressure and the crude material was recrystallized from hexanes to afford the product.

Example 12B

Synthesis of 4-(4-Methylphenyl) butanol

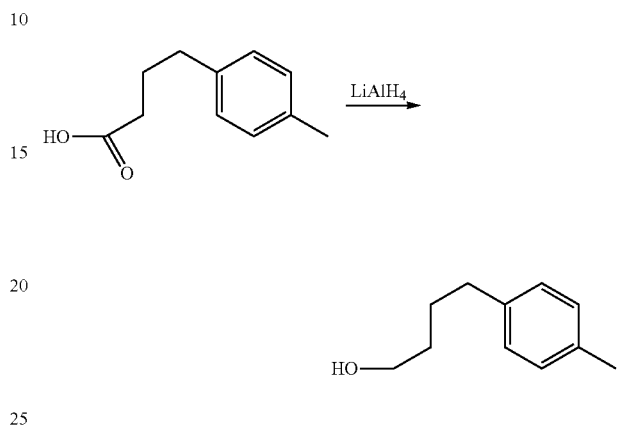

To lithium aluminum hydride (427 mg, 11.2 mmol) suspended in dry ether (5 ml) at 0° C. is added 1 g of 4-(4-methylphenyl) butanoic acid (5.614 mmol) dissolved in dry ether (10ml) over a period of 30 minutes. The reaction mixture is then allowed to warm to room temperature and stirred for 4 hours. Water (0.43 ml), NaOH (15% solution, 0.43 g) and water (1.29 ml) were then added successively and the resulting solution is stirred for 30 minutes. The resulting precipitate is filtered and washed with ether and dried. The filtrate is then concentrated and purified by flash chromatography using ethyl acetate-hexanes as the eluting medium.

Example 12C

Synthesis of 4-(4-methylphenyl)butyl tert-butyldimetylsilyl ether

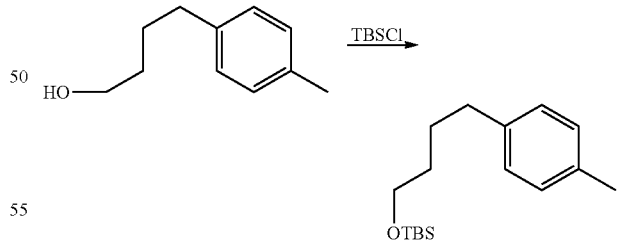

4-(4-Methylphenyl) butanol (0.5 g, 3.04 mmol) is dissolved in 5 ml DMF and to it is added imidazole (310 mg, 4.56 mmol) and tert-butyldimethylsilyl chloride (685 mg, 4.56 mmol). The reaction is stirred for 4 hrs after which it is extracted in ethyl acetate and washed with water to remove all DMF. The organic layer is then dried and concentrated. The crude mixture is then purified by flash chromatography using a mixture of ethyl acetate-hexanes as the eluting medium to afford the above mentioned product.

Example 12D

Synthesis of 4-(4-bromomethylphenyl) butyl tert-butyldimethylsilyl ether

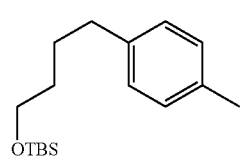

To a 50 ml round bottom flask is charged 4-(4-methylphenyl)butyl tert-butyldimetylsilyl ether (0.25 g, 0.89 mmol), N-bromosuccinimide (0.158 g, 0.89 mmol), benzoyl peroxide (2.17 mg, 0.0089 mmol) and 10 ml carbon tetrachloride. This mixture is refluxed overnight after which it is cooled and filtered. The filtrate is concentrated and the resulting crude residue purified by flash chromatography in ethyl acetate-hexanes to afford the product.

Example 12E

Synthesis of 4-(4-tert-butyldimethylsilyloxybutyl) phenylacetic acid 4-(4-bromomethylphenyl)butyl tert-butyldimethylsilyl ether (0.2 g, 0.561 mmol) in dry ether is added dropwise to Mg turnings (13.77 mg, 0.561 mmol). A few crystals of iodine are then added to initiate the reaction and the mixture is refluxed overnight under nitrogen atmosphere. The solution is then cooled and $CO_2$ gas is bubbled into it for 10

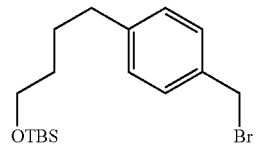

minutes. Stirring is continued for a further 2 hours after which water is added to the reaction mixture. The mixture is then extracted with ethyl acetate, washed and dried. After removing the organic solvent under reduced pressure the crude is purified by flash chromatography (silica gel; ethyl acetate/hexanes) to yield the desired product.

Example 12F

Synthesis of 2-hydroxyethyl-4-(4-tert-butyldimethylsilyloxybutyl) benzene

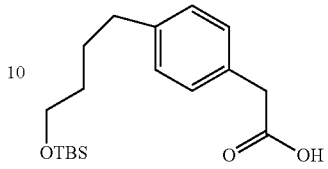

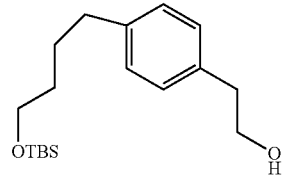

4-(4-tert-butyldimethylsilyloxybutyl)phenylacetic acid (0.25 g, 0.775 mmol) dissolved in dry ether is added dropwise to a suspension of lithium aluminum hydride in ether (44.2 mg, 1.16 mmol). The reaction mixture is stirred for 5 hours after which water (45 μl), NaOH(15% solution, 45 μl) and water (135 μl) are successively added and the reaction mixture is stirred for a further 30 minutes. The resulting precipitate is filtered and washed with ether. The ether filtrate is then washed with water and dried. After concentrating the ether, the product obtained is purified by flash chromatography (silica gel; ethyl acetate/hexanes).

Example 12G

Synthesis of 4-(2-(4-(4-tert-butyldimethylsilyloxybutyl) phenyl) ethoxy) quinazoline 2-hydroxyethyl-4-(4-tert-butyldimethylsilyloxybutyl) benzene (0.3 g, 0.97

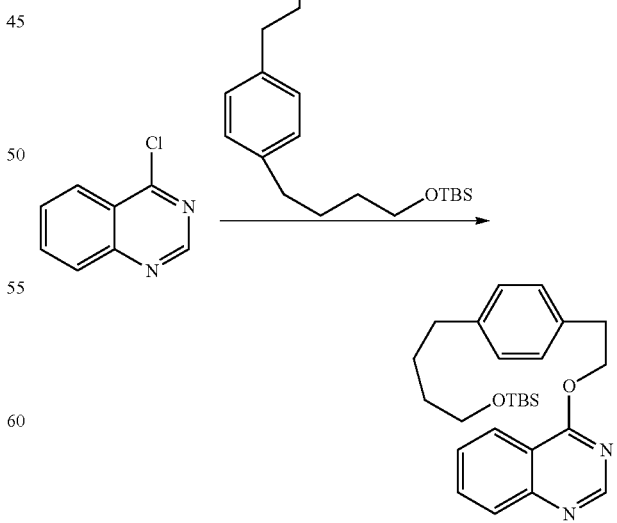

mmol) is dissolved in dry tetrahydrofuran and to it is added sodium hydride (24 mg, 1 mmol). The resulting solution is stirred at room temperature for 30 minutes after which 4-chloroquinazoline (0.164 g, 1 mmol) is added to the above solution. The solution is then stirred for 6 hours after which water is added to the mixture. The solution is then extracted in dichloromethane. The organic layer is washed, dried and then concentrated to yield the crude product which is purified by flash chromatography (silica gel; ethyl acetate/hexanes) to give the product.

Example 12H

Synthesis of 4-(2-(4-(4-hydroxybutyl)phenyl) ethoxy) quinazoline

To 4-(2-(4-(4-tert-butyldimethylsilyloxybutyl) phenyl) ethoxy) quinazoline (0.4 g, 0.916

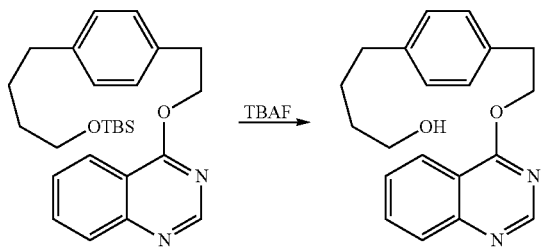

mmol) is added tetrabutylammonium fluoride solution (1M TBAF in THF, 4.58 ml, 4.58 mmol). The solution is stirred for 2 hours after which water is added to the reaction and this is extracted in ethyl acetate. The organic layer is then washed with water, dried and concentrated. The residue obtained is purified by flash chromatography (silica gel; ethyl acetate/hexanes).

Example 12I

Synthesis of 4-(2-(4-(4-p-toluenesulfonyloxybutyl) phenyl) ethoxy) quinazoline:

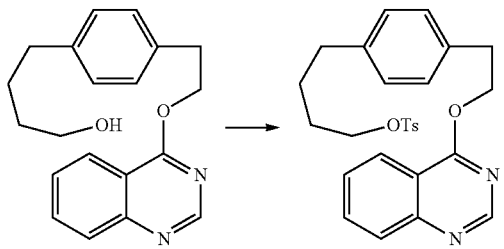 [SMILES: OCCCCc1ccc(CCOc2ncnc3ccccc23)cc1 ; Cc1ccc(S(=O)(=O)OCCCCc2ccc(CCOc3ncnc4ccccc34)cc2)cc1]

A 15 ml round bottom flask charged with 4-(2-(4-(4-hydroxybutyl)phenyl) ethoxy) quinazoline (0.25 g, 0.77 mmol) is dissolved in pyridine (5 ml). p-Toluenesulfonyl chloride (0.15 g, 0.79 mmol) is then added to it and the mixture stirred for 4 hours. The reaction mixture is diluted with ethyl acetate, washed with 5% copper sulfate solution and then with water and dried. After removing the solvent on the rotary evaporator the crude is purified by flash chromatography using silica gel (ethyl acetate/hexanes)to give the product.

Example 12J

Synthesis of 4-(2-(4-(4-fluorobutyl)phenyl) ethoxy) quinazoline

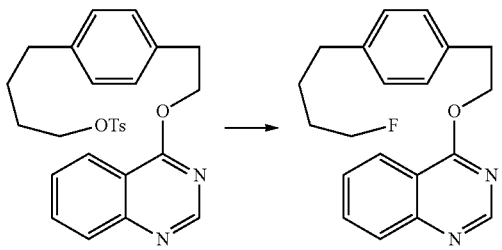 [SMILES: Cc1ccc(S(=O)(=O)OCCCCc2ccc(CCOc3ncnc4ccccc34)cc2)cc1 ; FCCCCc1ccc(CCOc2ncnc3ccccc23)cc1]

4-(2-(4-(4-p-toluenesulfonyloxybutyl)phenyl) ethoxy) quinazoline (0.3 g, 0.63 mmol) is added to a solution of potassium fluoride/kryptofix 222 in 5 ml THF (1:1 ratio, 3.15 mmol each). After stirring at room temperature for 15 minutes the solution is then refluxed for 20 minutes. It is then cooled and water is added to it. The solution is then extracted in dichloromethane and washed with water and dried. The crude product is purified by silica gel flash chromatography (ethyl acetate/hexanes) to afford the product.

Example 12K

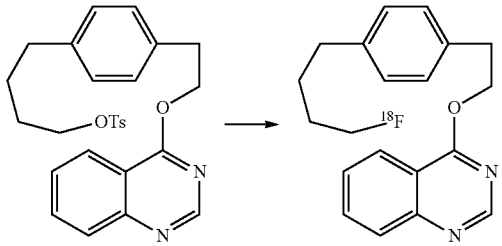 [SMILES: Cc1ccc(S(=O)(=O)OCCCCc2ccc(CCOc3ncnc4ccccc34)cc2)cc1 ; [18F]CCCCc1ccc(CCOc2ncnc3ccccc23)cc1]

Synthesis of 4-(2-(4-(4-[$^{18}$F]-fluorobutyl)phenyl) ethoxy) quinazoline

To a 5 ml reaction vial containing 100 mCi of $^{18}$F in 300 mg of $^{18}$O water is added a 1 ml solution consisting of 10 mg of Kryptofix, 1 mg potassium carbonate, 0.005 ml water and 0.95 ml acetonitrile. The vial is heated to remove all the solvents and dry acetonitrile (1 ml) is added to the vial. This is also removed by evaporation. 4-(2-(4-(4-p-toluenesulfonyloxybutyl)phenyl) ethoxy) quinazoline (5 mg) in acetonitrile is then added to it. The vial is sealed and heated for 30 minutes at 100° C. The mixture is diluted with dichloromethane and passed through a Sep-Pak and eluted with tetrahydrofuran. The solvent is evaporated to get the above mentioned compound.

Example 13

Figure 1B:
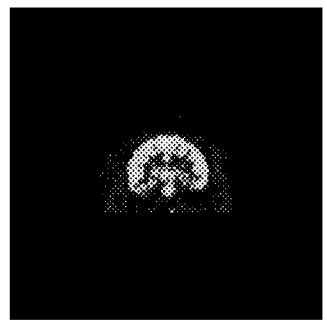
FIG. 1B shows representative images of the coronal plane of a nonhuman primate brain, with 2-tert-butyl-4-chloro-5-[4-(2-[$^{18}$F]fluoro-ethoxymethyl)-benzyloy]-2H-pyridazin-3-one in a normal NHP, where the whiter portions indicate localization of the contrast agent.
Figure 1C:
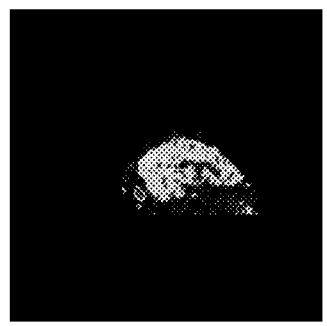
FIG. 1C shows representative images of the saggittal plane of a nonhuman primate brain, with 2-tert-butyl-4-chloro-5-[4-(2-[$^{18}$F]fluoro-ethoxymethyl)-benzyloy]-2H-pyridazin-3-one in a normal NHP, where the whiter portions indicate localization of the contrast agent.

Imaging with 2-tert-butyl-4-chloro-5-[4-(2-[$^{18}$F] fluoro-ethoxymethyl)-benzyloy]-2H-pyridazin-3-one in Normal Animals Imaging was performed with a microPET camera (Focus220, MICROPET) in anesthetized rats, rabbits and nonhuman primates (NHP) following the intravenous administration of 1, 2 and 3 mCi of $^{18}$F labeled 2-tert-butyl-4-chloro-5-[4-(2-fluoro-ethoxymethyl)-benzyloy]-2H-pyridazin-3-one, also referred to herein as Agent 2. After count acquisition, images were constructed and manually re-orientated as a series of tomographic views. FIG. 1 shows representative images of the (a) transverse, (b) coronal, and (c) saggittal planes of a brain, with 2-tert-butyl-4-chloro-5-[4-(2-[[$^{18}$F]fluoro-ethoxymethyl)-benzyloy]-2H-pyridazin-3-one in a normal NHP . These images were acquired 30 minutes post injection (mpi) of 5.1 mCi of 2-tert-butyl-4-chloro-5-[4-(2-[$^{18}$F]fluoro-ethoxymethyl)-benzyloy]-2H-pyridazin-3-one and were decay corrected. Intravenous injection of 2-tert-butyl-4-chloro-5-[4-(2-[$^{18}$F]fluoro-ethoxymethyl)-benzyloy]-2H-pyridazin-3-one did not induce changes in heart rate and ECG waveforms and all animals survived the image acquisition period with no adverse effects. It is apparent by the uptake and resolution of the images that Agent 2 is efficiently transported into the brain, providing useful images for the assessment of mitochondrial density function and brain perfusion.

Example 14

Imaging with Various Contrast Agents in Nonhuman Primates

Figure 2A:
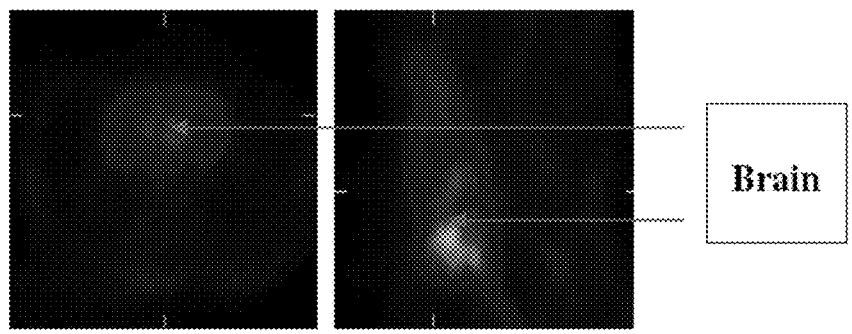
FIG. 2A shows representative images of the transverse (left image) and sagittal (right image) sections of a rat brain imaged using 2-tert-Butyl-4-chloro-5-[4-(2-($^{18}$F)fluoroethoxymethyl)-benzyloxy]-2H-pyridazin-3-one (Agent 2), where the whiter portions indicate localization of the contrast agent.
Figure 2B:
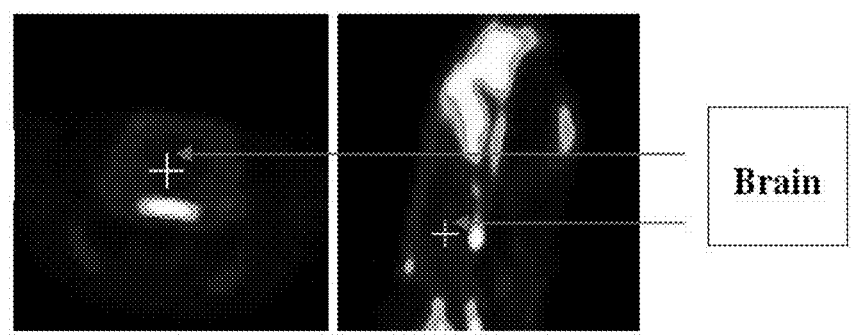
FIG. 2B shows representative images of the transverse (left image) and sagittal (right image) sections of a rat brain imaged using 2-tert-Butyl-4-chloro-5-[4-(3-($^{18}$F)fluoropropoxy)-benzyloxy]-2H-pyridazin-3-one (Agent 3), where the whiter portions indicate localization of the contrast agent.

In this example, imaging studies were performed using the three contrast agents listed in Table 1 below.

shows representative images of the transverse (left image) and sagittal (right image) sections of a rat brain imaged using Agent 2, while FIG. 2B shows representative images of the transverse (left image) and sagittal sections (right image) of a rat brain imaged using Agent 3. The results suggest that, unlike Agent 3, Agent 2 is capable of passing the blood brain barrier and accumulating in the brain.

Figure 3A:
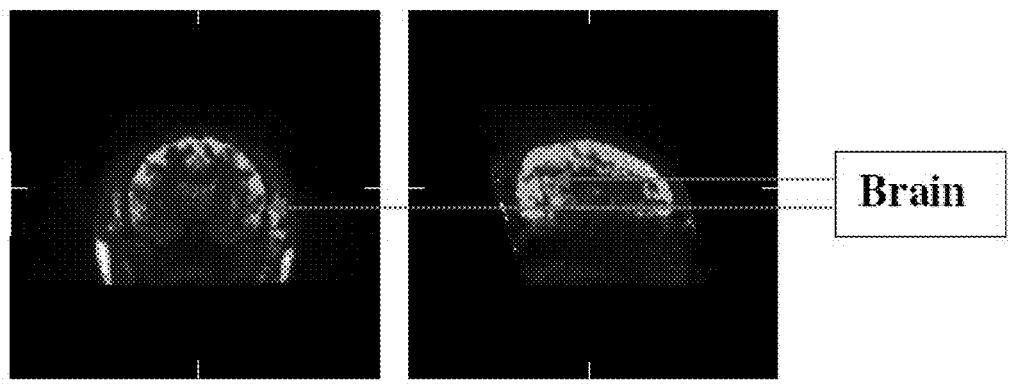
FIG. 3A shows representative tomographic images of the transverse (left image) and sagittal (right image) sections of a NHP brain imaged using Agent 2, where the whiter portions indicate localization of the contrast agent.
Figure 3B:
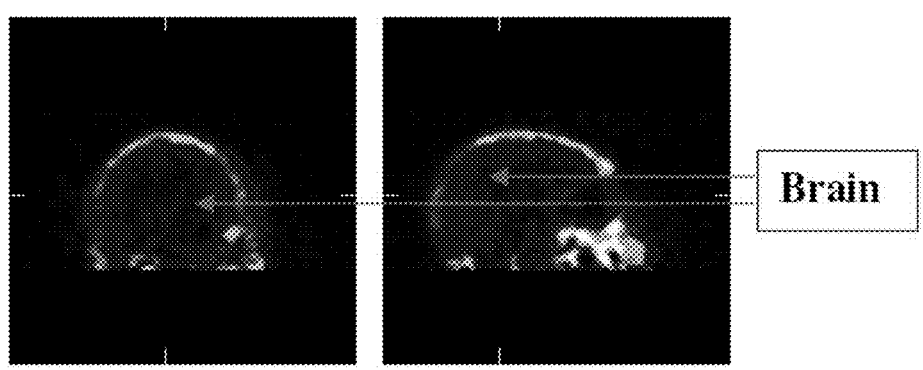
FIG. 3B shows representative tomographic images of the transverse (left image) and sagittal sections (right image) of a NHP brain imaged using 2-tert-butyl-4-chloro-5-[4-(4-[$^{18}$F]fluoro-butyl)-benzyloxy]-2H-pyridazin-3-one (Agent 1), where the whiter portions indicate localization of the contrast agent.

Similarly, in nonhuman primates (NHP), about 3 mCi of Agent 1 or Agent 2 was injected intravenously and the brain of NHP was imaged in a microPET. FIG. 3A shows representative tomographic images of the transverse (left image) and sagittal (right image) sections of a NHP brain imaged using Agent 2, while FIG. 3B shows representative tomographic images of the transverse (left image) and sagittal sections (right image) of a NHP brain imaged using Agent 1. The NHP brain was not visible when imaged with Agent 1. However, the NHP brain was visible when imaged with Agent 2, indicating that Agent 2 is capable of passing through blood brain barrier and accumulating in the brain.

The structure-activity relationship (SAR) study described in this example indicate that the presence and/or position of a heteroatom (e.g., oxygen atom) in the side chain of the contrast agent can affect its ability to diffuse through blood brain barrier. While omission of a heteroatom in the side chain of Agent 1 increased the lipophilicity of Agent 1 (Log

TABLE 1

Contrast Agents utilized in imaging study.

| Agent | Chemical Name | Chemical Structure |
|---|---|---|
| 1 | 2-tert-butyl-4-chloro-5-[4-(4-[$^{18}$F]Fluoro-butyl)-benzyloxy]-2H-pyridazin-3-one | 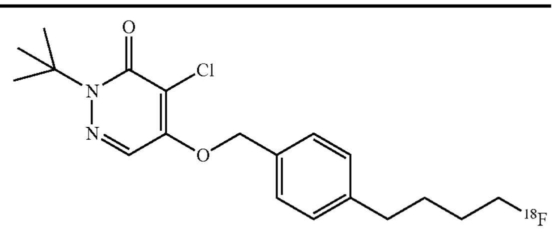 |
| 2 | 2-tert-Butyl-4-chloro-5-[4-(2-($^{18}$F)fluoroethoxymethyl)-benzyloxy]-2H-pyridazin-3-one | 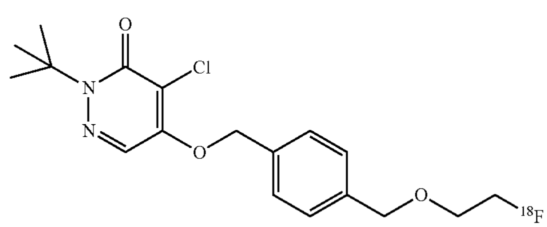 [SMILES: CC(C)(C)n1ncc(OCc2ccc(COCC[18F])cc2)c(Cl)c1=O] |
| 3 | 2-tert-Butyl-4-chloro-5-[4-(3-($^{18}$F)fluoropropoxy)-benzyloxy]-2H-pyridazin-3-one | 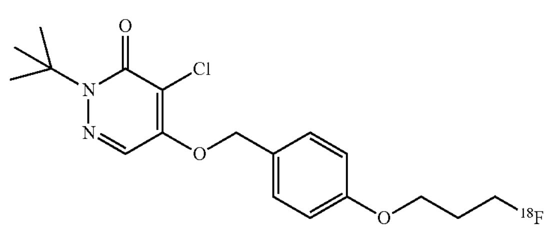 [SMILES: CC(C)(C)n1ncc(OCc2ccc(OCCC[18F])cc2)c(Cl)c1=O] |

After anesthesia, about 1 mCi of Agent 2 or Agent 3 was injected into a rat intravenously and the rat brain was imaged in a microPET scanner. Following the image acquisition, the images were reconstructed into tomographic views. FIG. 2A P value: 4.84 vs. 2.73 of Agent 2 calculated with ACD/ChemSketch v.11.02 software, Advanced Chemistry Development, Inc., Toronto ON), it exhibited decreased penetration into the brain, relative to Agent 2.

Example 15

Imaging with Agent 2 in Mouse Models of Tumor

Figure 4:
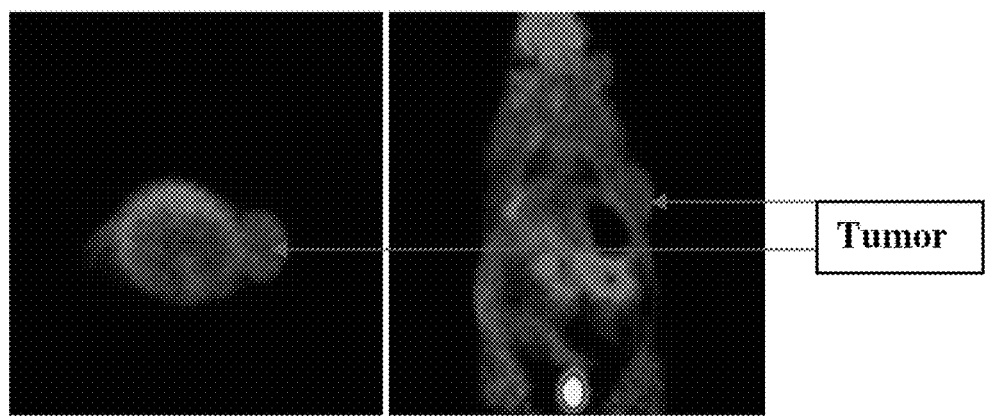
FIG. 4 shows representative transverse (left image) and coronal (right image) images of a c-neu ONCO mouse imaged with Agent 2, where the whiter portions indicate localization of the contrast agent.

Imaging studies using several mouse tumor models, including c-neu ONCO mice, nu/nu mice with OVCAR tumor, and nu/nu mice with HT1080 tumor, were conducted using contrast agents described herein. After administering anesthesia to the mouse, about 500 µCi of Agent 2 (from Table 1) were injected intravenously and the tumor was imaged in a microPET scanner. After imaging acquisition, images were reconstructed into tomographic views. FIG. 4 shows representative transverse (left image) and coronal (right image) images of a c-neu ONCO mouse, where the tumor was visible when imaged with Agent 2. In addition, tumor uptake of Agent 2 was measured in the mouse models after imaging. The uptake was detectable in a range from 1-4% injected dose per gram tissue.

It will be evident to one skilled in the art that the present invention is not limited to the foregoing illustrative examples, and that it can be embodied in other specific forms without departing from the essential attributes thereof. It is therefore desired that the examples be considered in all respects as illustrative and not restrictive, reference being made to the appended claims, rather than to the foregoing examples, and all changes which come within the meaning and range of equivalency of the claims are therefore intended to be embraced therein.

What is claimed is:

1. A method of imaging cancer in a subject, comprising:
administering to a subject with cancer a contrast agent which comprises an imaging moiety and a compound bound to the imaging moiety, scanning the patient using diagnostic imaging to produce an image of at least a portion of the cancer, wherein the contrast agent has a structure as in Formula (II),

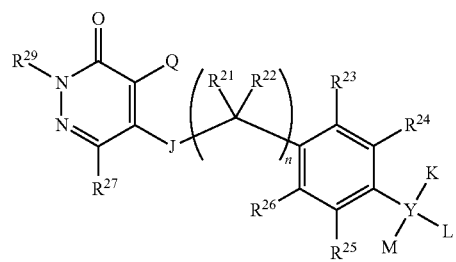

(II)

wherein:
J is selected from $N(R^{27})$ S, O, $C(=O)$, $C(=O)O$, $NHCH_2CH_2O$, a bond, or $C(=O)N(R^{27})$;
K and L, when present, are independently selected from hydrogen, alkoxyalkyl, alkyloxy, aryl, alkyl, heteroaryl, and an imaging moiety, each of which is optionally substituted;
M is selected from hydrogen, alkoxyalkyl, alkyloxy, aryl, alkyl, heteroaryl, and an imaging moiety, each of which is optionally substituted, or
L and M, together with the atom to which they are attached, form a ring, optionally substituted;
Q is halo or haloalkyl;
n is 0, 1, 2, or 3;
$R^{21}$, $R^{22}$, $R^{23}$, $R^{24}$, $R^{25}$, $R^{26}$, and $R^{27}$ are independently selected from hydrogen, alkyl, optionally substituted, and an imaging moiety;
$R^{29}$ is alkyl, optionally substituted; and
Y is selected from a bond, carbon, and oxygen; provided that when Y is a bond, K and L are absent and M is selected from aryl and heteroaryl, each of which is optionally substituted; and
provided that when Y is oxygen, K and L are absent and M is selected from hydrogen, alkoxyalkyl, aryl, alkyl, and heteroaryl, each of which is optionally substituted,
wherein at least one imaging moiety is present in Formula (II) and is $^{18}F$.

2. The method as in claim 1, wherein the image is used in the diagnosis of a subject.

3. The method as in claim 2, wherein the diagnosis is a diagnosis of a cancer.

4. The method as in claim 1, wherein the image is used to determine the stage of a cancer.

5. The method as in claim 1, further comprising selecting a treatment of a cancer in the subject based at least in part on the image of at least a portion of the cancer.

6. The method as in claim 1, further comprising evaluating a treatment of a cancer in the subject based at least in part on the image of at least a portion of the cancer.

7. The method as in claim 1, wherein the cancer is a primary tumor or neoplasia.

8. The method as in claim 1, wherein the cancer is a metastatic growth.

9. The method as in claim 1, wherein J is O and $R^{29}$ is $C_1$-$C_6$ alkyl.

10. The method as in claim 1, wherein $R^{29}$ is tert-butyl.

11. The method as in claim 1, wherein M is alkoxyalkyl, optionally substituted with an imaging moiety.

12. The method as in claim 1, wherein the contrast agent is selected from the following group:

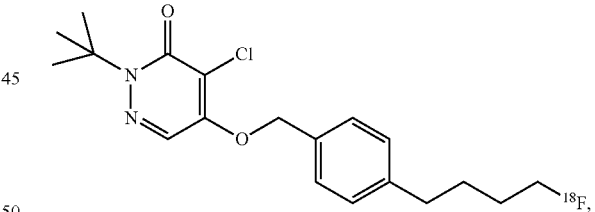

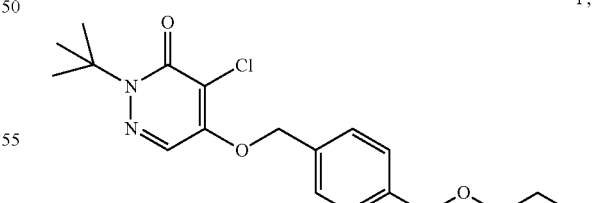

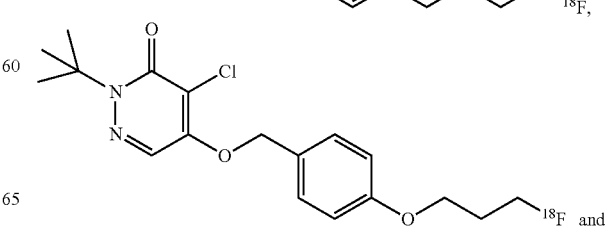

-continued

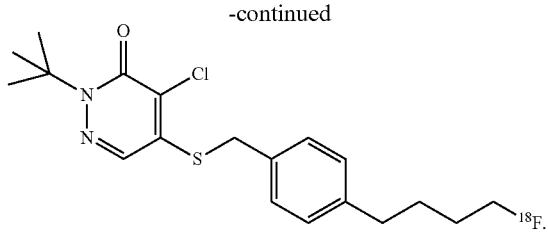

13. The method as in claim 1, wherein the contrast agent is:

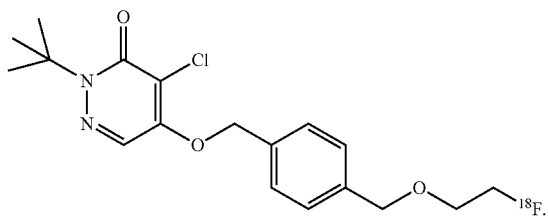

14. The method as in claim 2, wherein the contrast agent is:

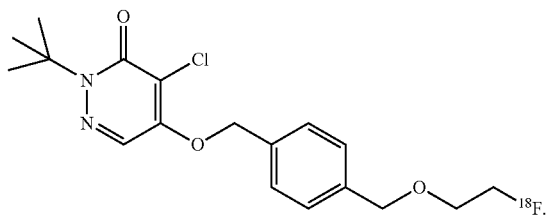

15. The method as in claim 3, wherein the contrast agent is:

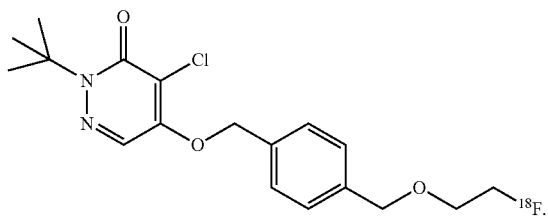

16. The method as in claim 4, wherein the contrast agent is:

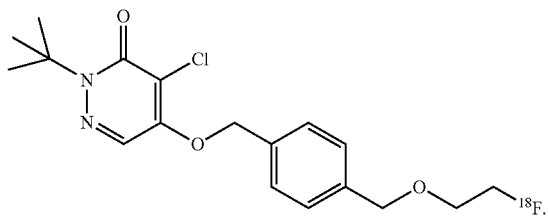

17. The method as in claim 5, wherein the contrast agent is:

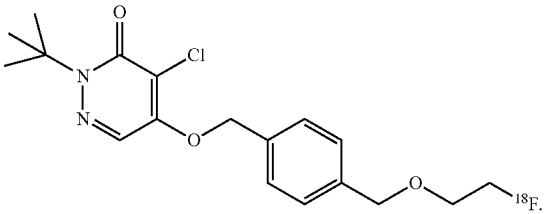

18. The method as in claim 6, wherein the contrast agent is:

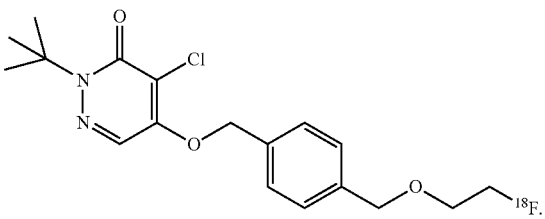

19. The method as in claim 7, wherein the contrast agent is:

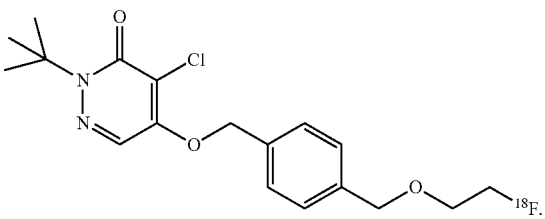

20. The method as in claim 8, wherein the contrast agent is:

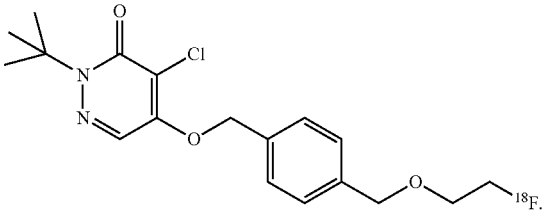

* * * * *